US008628509B2

(12) United States Patent
Kropczynski, Jr. et al.

(10) Patent No.: US 8,628,509 B2
(45) Date of Patent: Jan. 14, 2014

(54) ENTERAL CONNECTORS AND SYSTEMS

(75) Inventors: John J. Kropczynski, Jr., Dublin, OH (US); James Perry, Gahanna, OH (US); Meghan Walter, Columbus, OH (US); Dennis Kopilec, Louisville, KY (US); Allan Cameron, Natick, MA (US); Christine Ciccone, Marshfield, MA (US); Thomas Parent, Cambridge, MA (US); Brian Stonecipher, Ashland, MA (US); Philip C. Walker, Concord, MA (US); James Wilson, Norwood, MA (US)

(73) Assignee: Abbott Laboratories, Abbott Park, IL (US)

( * ) Notice: Subject to any disclaimer, the term of this patent is extended or adjusted under 35 U.S.C. 154(b) by 238 days.

(21) Appl. No.: 12/775,136

(22) Filed: May 6, 2010

(65) Prior Publication Data

US 2011/0118676 A1    May 19, 2011

Related U.S. Application Data

(60) Provisional application No. 61/176,964, filed on May 11, 2009, provisional application No. 61/246,200, filed on Sep. 28, 2009, provisional application No. 61/295,883, filed on Jan. 18, 2010.

(51) Int. Cl.
*A61M 5/32* (2006.01)
(52) U.S. Cl.
USPC ........................................................ 604/414
(58) Field of Classification Search
USPC .......................... 604/244, 262, 414, 415, 910
See application file for complete search history.

(56) References Cited

U.S. PATENT DOCUMENTS

| 1,889,557 A | 11/1932 | Lange |
| 2,072,853 A | 3/1937 | Baxter |
| 2,894,510 A | 7/1959 | Bellamy |

(Continued)

FOREIGN PATENT DOCUMENTS

| EP | 1205212 A2 | 5/2002 |
| WO | WO93/20772 | 10/1993 |

(Continued)

OTHER PUBLICATIONS

Written Opinion of the International Searching Authority for PCT/US12010/034358 dated Sep. 13, 2010.

(Continued)

*Primary Examiner* — Nicholas Lucchesi
*Assistant Examiner* — Diva K Chander
(74) *Attorney, Agent, or Firm* — Calfee, Halter & Griswold LLP

(57) ABSTRACT

An enteral connector assembly and system (700) communicates fluid between a bag B' or a bottle B" and an enteral feeding set. The system (700) includes an end cap (705) that communicates enteral fluid across a barrier (715) having a specially configured barrier keyway (720) formed with a barrier port (725). The barrier (715) establishes an interstice (165) that when combined with the spike barrier (715) prevents introduction of and fluid communication with legal intravenous spikes (LS) and other incompatible connectors, while enabling connection to and fluid communication with compatible components such as an interconnect (740) having multiple tines (745) that include specially shaped tips (750) that extend across the interstice (165) to pierce a seal, septum, and/or sealing membrane and form a fluid pathway.

20 Claims, 48 Drawing Sheets

(56) References Cited

U.S. PATENT DOCUMENTS

| | | | |
|---|---|---|---|
| 3,030,955 A | 4/1962 | Gossett | |
| 3,670,728 A | 6/1972 | Dabney | |
| 3,813,009 A | 5/1974 | Lenz | |
| 3,852,385 A | 12/1974 | Huggins | |
| 3,857,909 A | 12/1974 | Huggins | |
| 4,022,258 A * | 5/1977 | Steidley | 141/330 |
| 4,361,147 A | 11/1982 | Aslanian et al. | |
| 4,405,312 A | 9/1983 | Gross et al. | |
| 4,432,759 A | 2/1984 | Gross et al. | |
| 4,458,811 A | 7/1984 | Wilkinson | |
| 4,493,348 A | 1/1985 | Lemmons | |
| 4,523,691 A | 6/1985 | Larkin et al. | |
| 4,547,900 A | 10/1985 | Larkin et al. | |
| 4,548,606 A | 10/1985 | Larkin | |
| 4,576,602 A | 3/1986 | Levin et al. | |
| D284,221 S | 6/1986 | Kerkut | |
| 4,722,727 A * | 2/1988 | Ogden et al. | 604/30 |
| 4,723,956 A | 2/1988 | Schnell et al. | |
| 4,786,279 A | 11/1988 | Wilkinson et al. | |
| D302,305 S | 7/1989 | Fuller | |
| D306,759 S | 3/1990 | D'Alo | |
| D307,795 S | 5/1990 | Frantz | |
| 4,934,545 A | 6/1990 | Pezzoli et al. | |
| 4,951,845 A * | 8/1990 | Pezzoli et al. | 215/250 |
| 5,047,021 A | 9/1991 | Utterberg | |
| 5,059,173 A | 10/1991 | Sacco | |
| 5,102,408 A | 4/1992 | Hamacher | |
| 5,125,522 A | 6/1992 | Pezzoli et al. | |
| 5,289,858 A | 3/1994 | Grabenkort | |
| 5,334,179 A | 8/1994 | Poli et al. | |
| 5,334,180 A * | 8/1994 | Adolf et al. | 604/411 |
| 5,364,384 A | 11/1994 | Grabenkort et al. | |
| D354,129 S | 1/1995 | Salvadori | |
| 5,391,150 A | 2/1995 | Richmond | |
| D356,150 S | 3/1995 | Duggan et al. | |
| 5,395,365 A * | 3/1995 | Weiler et al. | 604/415 |
| 5,405,333 A | 4/1995 | Richmond | |
| D359,684 S | 6/1995 | Duggan et al. | |
| D367,325 S | 2/1996 | Duggan et al. | |
| 5,514,123 A | 5/1996 | Adolf et al. | |
| 5,520,666 A | 5/1996 | Choudhury et al. | |
| 5,540,674 A | 7/1996 | Karas et al. | |
| 5,549,566 A | 8/1996 | Elias et al. | |
| 5,658,260 A | 8/1997 | Desecki et al. | |
| 5,681,294 A | 10/1997 | Osborne et al. | |
| 5,682,662 A | 11/1997 | Coules et al. | |
| 5,682,874 A | 11/1997 | Grabenkort et al. | |
| 5,685,866 A | 11/1997 | Lopez | |
| 5,695,466 A | 12/1997 | Lopez | |
| 5,738,651 A | 4/1998 | Walton et al. | |
| 5,755,563 A | 5/1998 | Clegg et al. | |
| 5,772,255 A | 6/1998 | Osborne et al. | |
| 5,807,333 A | 9/1998 | Osborne et al. | |
| 5,848,994 A | 12/1998 | Richmond | |
| 5,891,129 A | 4/1999 | Daubert et al. | |
| 5,897,526 A | 4/1999 | Vaillancourt | |
| 5,910,135 A | 6/1999 | Hadzic et al. | |
| 5,924,584 A | 7/1999 | Hellstrom et al. | |
| 5,954,104 A | 9/1999 | Daubert et al. | |
| 5,964,785 A | 10/1999 | Desecki et al. | |
| 6,012,596 A | 1/2000 | Oglesbee et al. | |
| 6,024,234 A | 2/2000 | Rink et al. | |
| 6,139,534 A | 10/2000 | Neidospial et al. | |
| 6,179,821 B1 | 1/2001 | Capary et al. | |
| 6,183,465 B1 | 2/2001 | Meier et al. | |
| 6,223,940 B1 | 5/2001 | Quinn | |
| 6,558,365 B2 | 5/2003 | Zinger et al. | |
| 6,610,041 B2 * | 8/2003 | Verlee et al. | 604/415 |
| 6,685,692 B2 | 2/2004 | Fathallah | |
| 6,726,672 B1 | 4/2004 | Hanly et al. | |
| 6,875,204 B1 | 4/2005 | Hopkins et al. | |
| 7,025,389 B2 * | 4/2006 | Cuschieri et al. | 285/243 |
| 7,074,216 B2 * | 7/2006 | Fowles et al. | 604/413 |
| 7,080,672 B2 | 7/2006 | Fournie et al. | |
| 7,083,058 B2 | 8/2006 | Perry et al. | |
| 7,354,426 B2 | 4/2008 | Young | |
| 7,544,191 B2 * | 6/2009 | Peluso et al. | 604/414 |
| 2004/0002684 A1 | 1/2004 | Lopez | |
| 2004/0015121 A1 | 1/2004 | Ryan et al. | |
| 2004/0073189 A1 | 4/2004 | Wyatt et al. | |
| 2004/0153047 A1 | 8/2004 | Blank et al. | |
| 2007/0060898 A1 * | 3/2007 | Shaughnessy et al. | 604/284 |
| 2007/0079894 A1 | 4/2007 | Kraus et al. | |
| 2007/0093775 A1 | 4/2007 | Daly | |
| 2007/0112323 A1 | 5/2007 | Daly | |
| 2008/0004574 A1 | 1/2008 | Dyar et al. | |
| 2008/0015539 A1 | 1/2008 | Pieroni et al. | |

FOREIGN PATENT DOCUMENTS

| | | |
|---|---|---|
| WO | WO02/09636 A1 | 2/2002 |
| WO | WO2004/017852 A1 | 3/2004 |
| WO | WO2008/049568 A1 | 5/2008 |

OTHER PUBLICATIONS

International Search Report for PCT/US/2010/034358 dated Sep. 13, 2010.

International Preliminary Report on Patentability for PCT/US/2010/034358 dated Jul. 8, 2011.

English Translation of Office Action from Israeli Application 215,998—dated Feb. 17, 2013, reported by Israeli associate on Apr. 29, 2013.

Office Action (including English translation) from CN Application No. 201080031308.2 dated Mar. 5, 2013, reported by Chinese associate on Apr. 27, 2013.

Written Opinion prepared by Danish Patent Office on behalf of IPOS for Singapore Application No. 201108159-3, mailed Jan. 14, 2013.

Office Action from Columbian Patent Application No. 11-154.060 reported by Colombian associate Jun. 5, 2013.

Exam Report from Australian Patent Application No. 2010247839 mailed Aug. 30, 2013.

Substantive Examination Report from Philippines Patent Application No. 1/2011/502320 mailed Sep. 4, 2013.

* cited by examiner

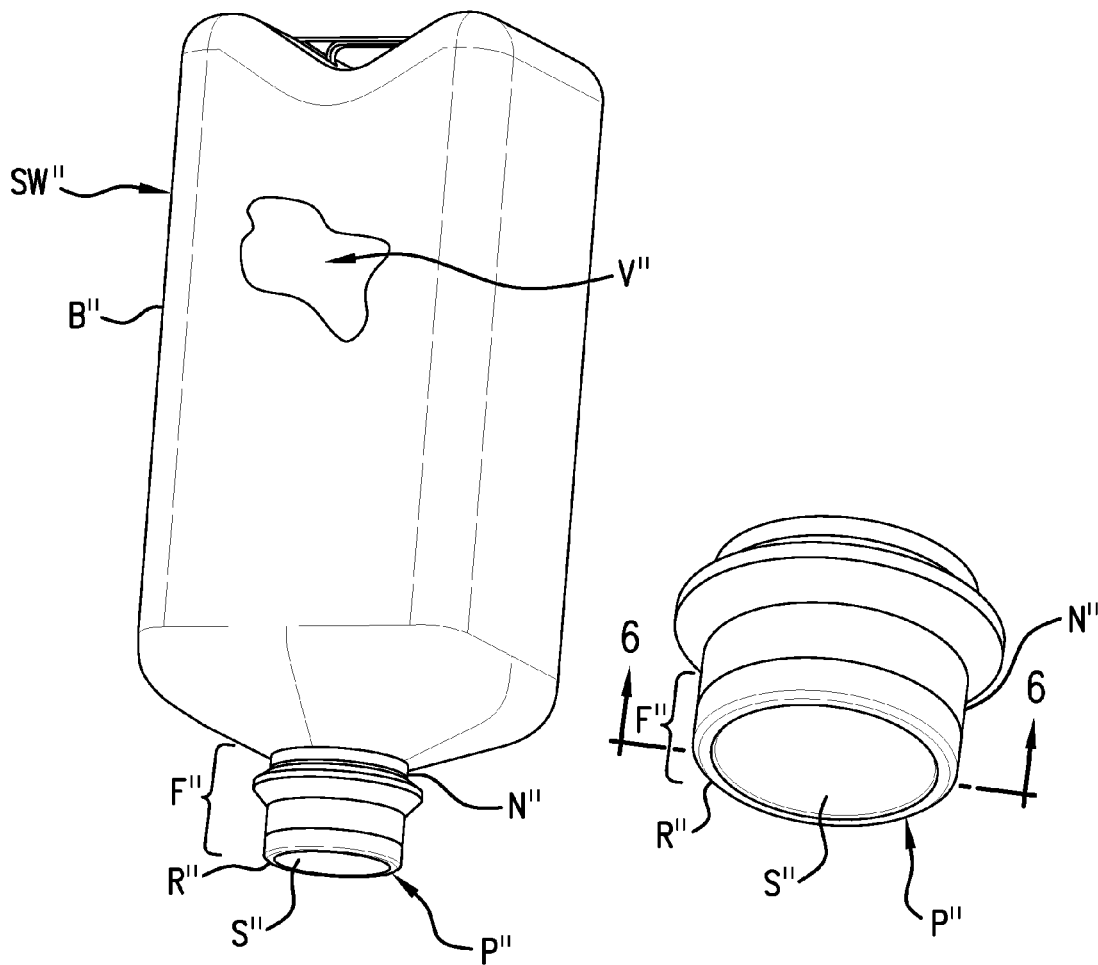
FIG.4
(Prior Art)
FIG.5
(Prior Art)
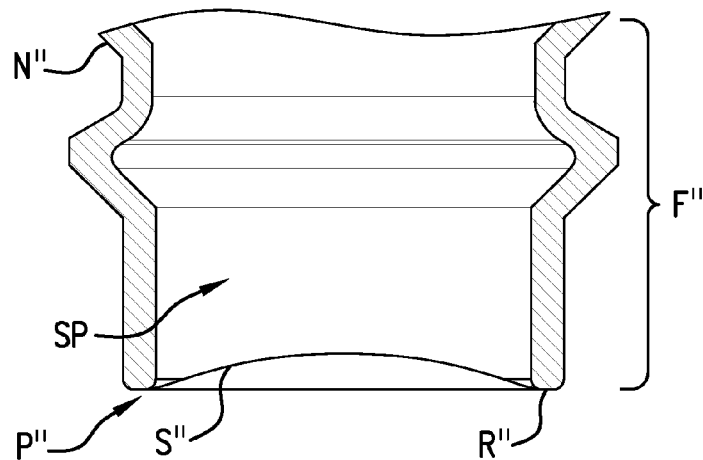
FIG.6
(Prior Art)

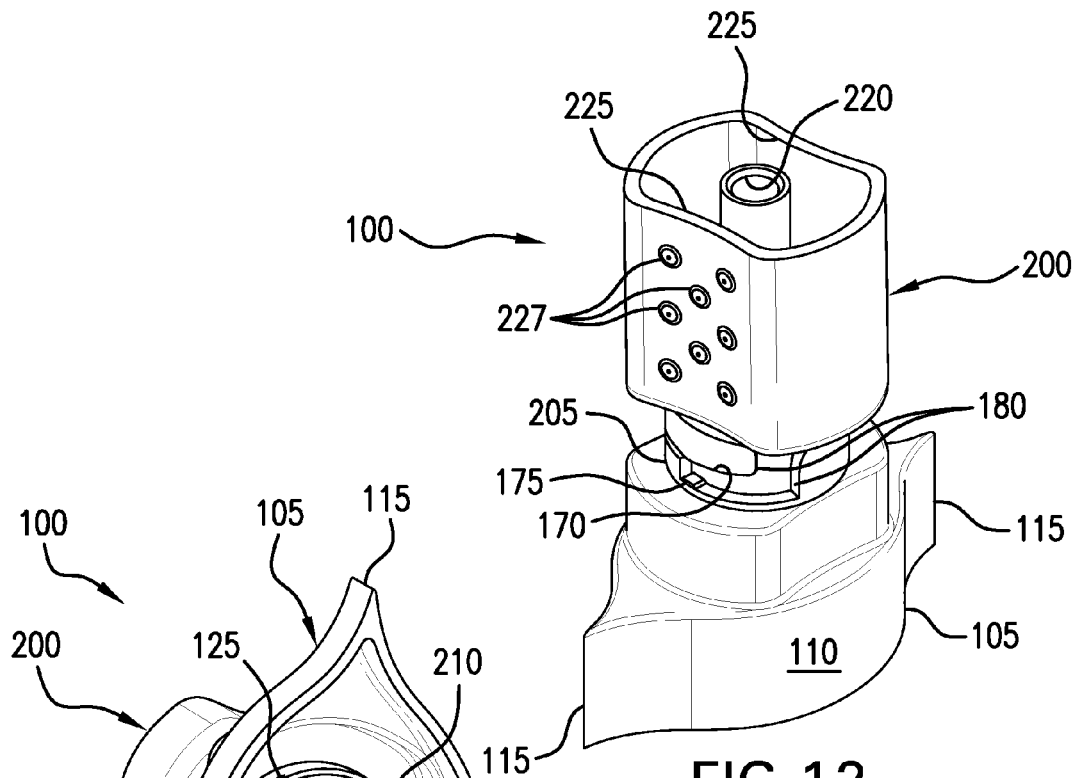
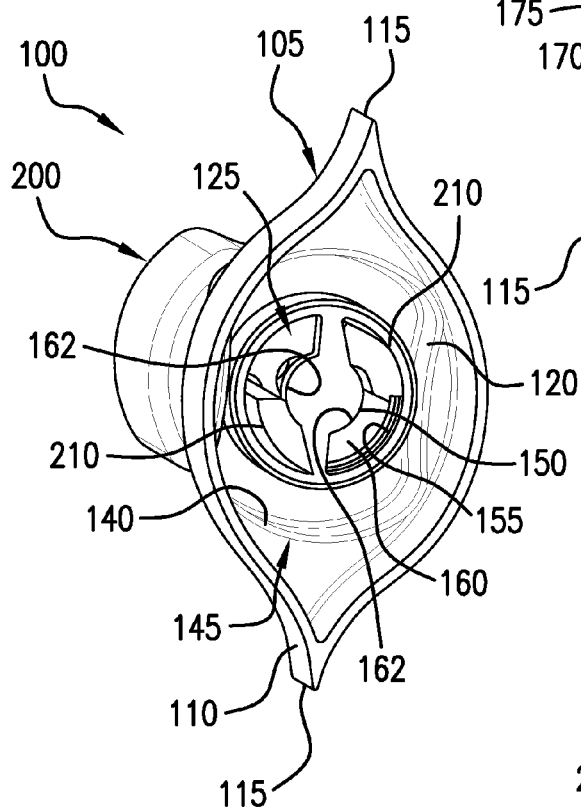
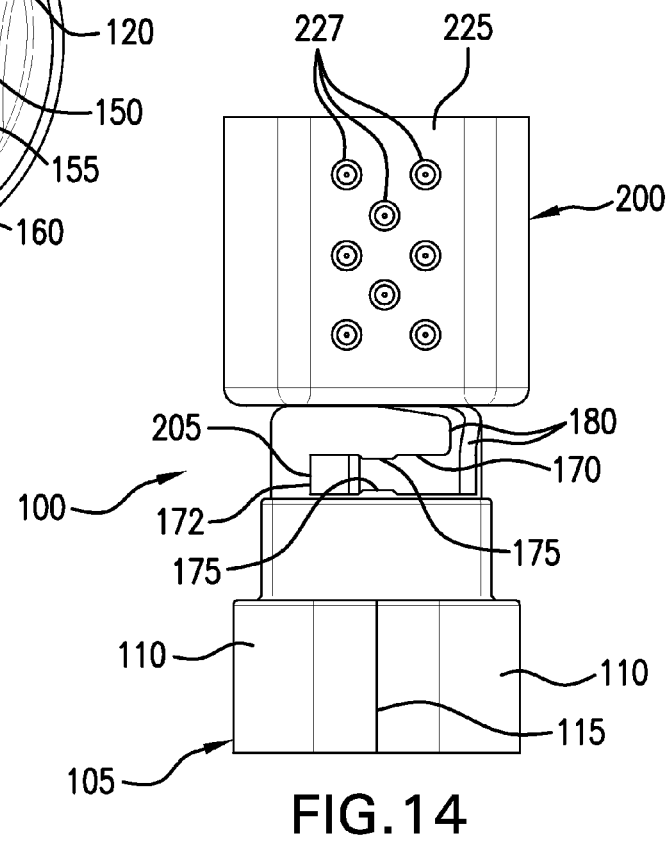
FIG. 12
FIG. 13
FIG. 14

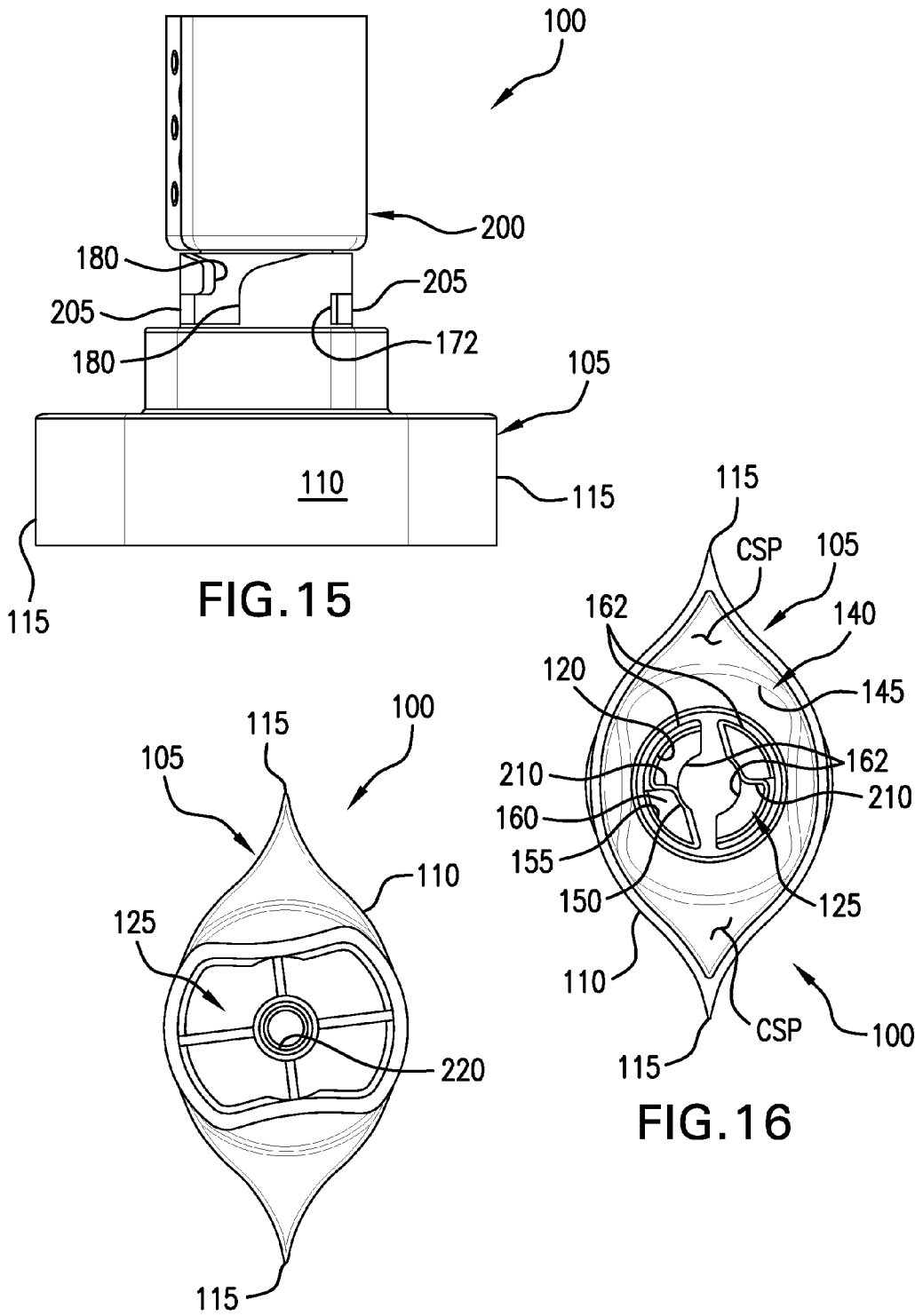

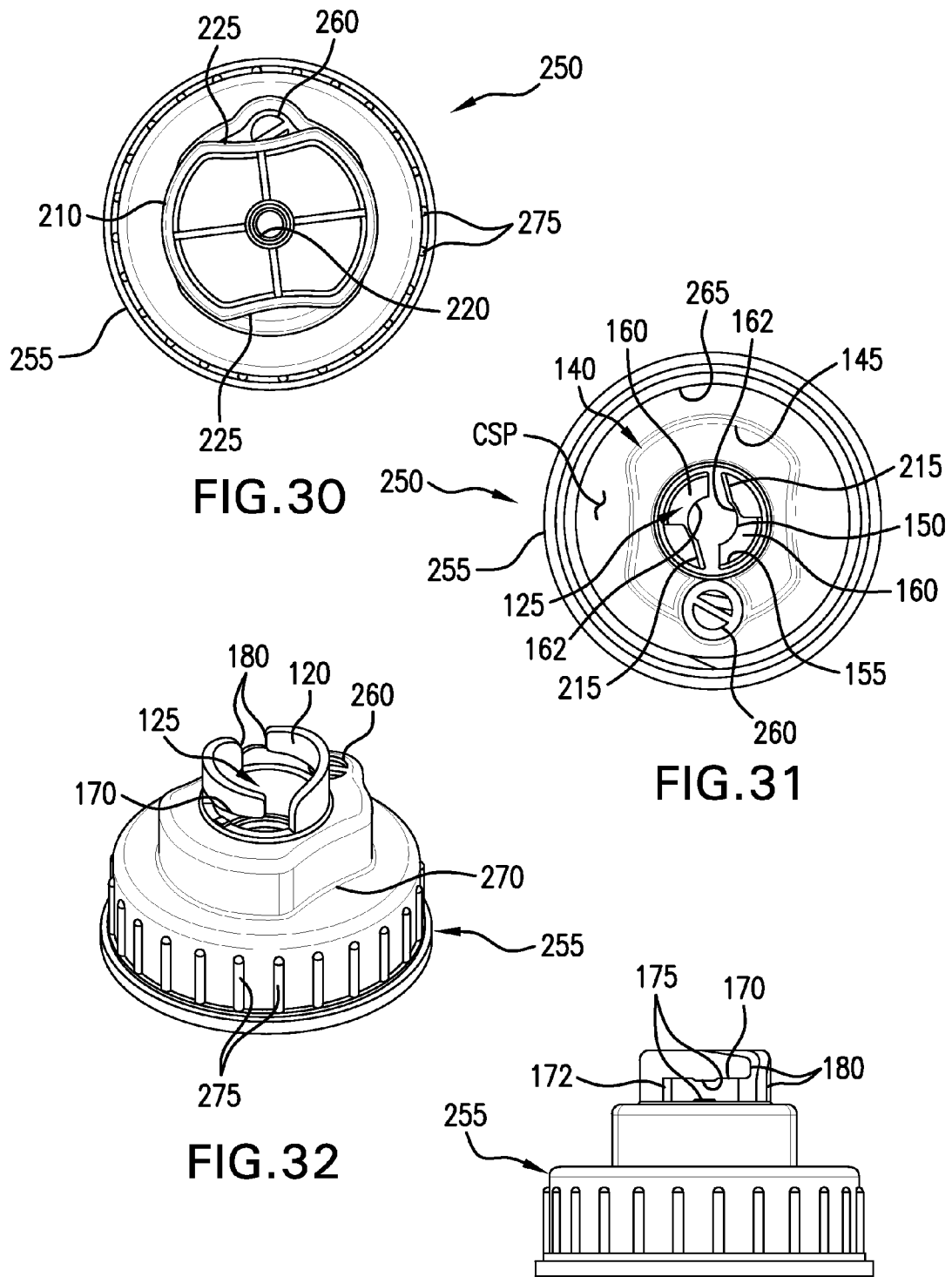

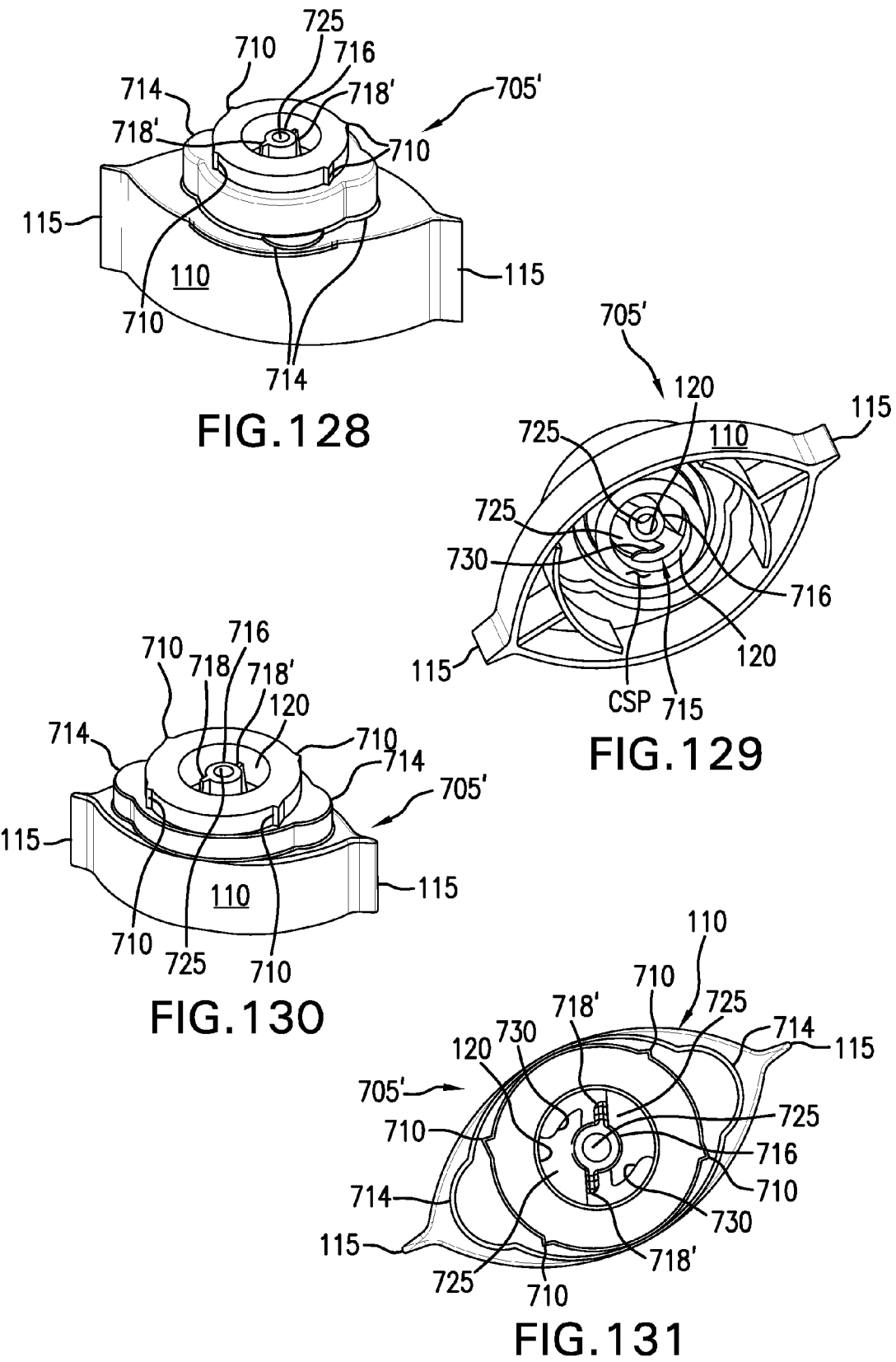

ENTERAL CONNECTORS AND SYSTEMS

This application claims the benefit of U.S. Provisional Application No. 61/176,964, filed May 11, 2009, and U.S. Provisional Application No. 61/246,200, filed Sep. 28, 2009, and U.S. Provisional Application 61/295,883, filed Jan. 18, 2010.

BACKGROUND OF THE INVENTION

1. Field of the Invention

This invention relates to the field of enteral and medical fluid product delivery connectors and related systems.

2. Description of Related Art

Fluid delivery, flowable product, and substantially liquid product delivery systems for enteral applications in the nutritional, nutraceutical, and medical fields are available in many variations. Such delivery systems most often include a fluid source, receptacle, rigid or flexible bottle, soft pouch, collapsible bag, or other type of container configured to contain an enterally administered flowable substance such as a liquid or fluid.

Such containers are either (1) filled with a fluid and sealed at a factory before delivery to a user, or (2) is delivered ready for filling by the user and/or fluid recipient. When delivered ready for filling, the containers may be empty, and may also include a concentrate, precipitate, or a fluid that can be mixed and/or hydrated with another liquid, fluid, and/or flowable or powdered substance or product by the user and fluid recipient.

For purposes of describing the instant invention, but not for purposes of limitation, all such containers will be referred to herein generically as bottles and/or collapsible bags. All such flowable substances, products, liquids, fluids, and other contents to be enterally administered will be generally referred to as liquids and/or fluids for purposes of illustration without limitation.

Those skilled in the relevant arts have conventionally categorized such enteral fluid delivery systems and containers into two general groups. The factory filled and sealed containers are usually described to be closed systems, which means they are delivered to users and recipients in a sealed state. The fluid delivery systems and containers that are delivered ready for filling by users and recipients are usually described as open systems. delivered to users and recipients in a sealed state. The fluid delivery systems and containers that are delivered ready for filling by users and recipients are usually described as open systems.

These delivery systems also typically include liquid administration and/or fluid delivery sets that typically incorporate a length of tubing that has a plurality of connectors. At a minimum, the connectors often include a connector adapted to connect to and establish fluid communication with the fluid container, and tubing extending to a fluid recipient and/or one or more other connectors for communicating the fluid to the recipient.

Such enterally adapted liquid product or fluid delivery systems are substantially different from what are known to those skilled in the relevant arts as intravenous (IV) fluid delivery systems. Most often, the primary difference is that the enteral systems are capable of delivering higher density and/or more viscous fluids to the recipient than is possible with IV systems.

To accomplish the delivery of such more dense and viscous fluids, enteral fluid delivery systems usually include fluid pathways formed from tubing, connectors, and fitments that have larger internal diameters. Such connectors and tubing are typically made from various polymeric materials suitable for the contemplated enteral liquid and fluid products. The larger diameter fluid pathways also enable communication of enteral fluids more rapidly to the recipient than is possible or indicated for IV fluid delivery systems. IV fluids are typically administered over substantially longer spans of time than is usually desired for the delivery of enteral liquids, and can often be accommodated with smaller fluid pathways. Administration of enteral products may use such smaller fluid pathways, but are more often intended for delivery in indwelling applications to communicate more viscous and dense fluids more rapidly, which is facilitated by the larger diameter pathways.

Referring to the various figures and illustrations, and especially now to FIG. 1, an elevation view is shown of a prior art, prefilled, closed-system collapsible fluid pouch or bag B, which is also referred to by those in the field of art as a ready-to-hang (RTH) pouch or bag B. In alternative arrangements, the bag may also be used in an open system that is delivered empty and fillable by a user or fluid recipient.

The bag B includes a sidewall or walls SW that defines an interior volume V. Although in these various figures, the interior volume reference symbol V points to a surface of the bag B, it is assumed for illustration purposes without limitation that the substantially collapsible bag is made from a substantially transparent polymeric material such that the reference symbol adequately designates the interior volume of the bag B.

The bag B extends to a neck N having a finish F terminated with a rim R that defines a fluid communication port P about a proximal end of the bag B. The finish F may incorporate threads TH, and/or other types of attachment system. In a closed-system configuration, a sealed septum, sealing membrane, or seal (not shown) may be carried from the rim R after the bag B has been filled aseptically, and before retort processing as may be preferred.

Before use, the seal or membrane will be punctured or pierced, or removed entirely or partially, and the bag B will be connected to an end cap or cap C. The end cap or cap may be integrally attached to or adapted to be connected with an administration set AS. Typically, collapsible containers like bag B do not require vented caps C as the bag B collapses during operation as the contents are dispensed.

Since administration sets AS may be used for multiple types of containers, cap C may also preferably include a vent VT to equalize pressure between an interior of the container or bag B and the external atmosphere as the contents are administered. This capability is required to enable fluid to leave a rigid container that cannot flex or collapse to equalize pressure as fluid leaves the interior volume V.

The set AS will also include a lumen or tube T that extends to other connectors or a fluid recipient. During operation, the assembled RTH bag B and cap C may be hung from a gravity or elevation pole GP to administer or deliver fluids to the recipient. The intent of the GP is to raise the bag B higher than the fluid recipient to establish a head pressure on the liquid contained in the bag B that is sufficient to administer the liquid to the fluid recipient during gravity dispensement operation.

FIG. 2 is an elevation view of a prior art RTH, fillable, open-system, collapsible, and substantially transparent, polymeric bag B' that might be used for administration of enteral or intravenous (IV) fluids. This configuration is typical of open systems which often include a second bag port BP about a distal end of the bag B', which second bag port BP is most often and generally opposite the proximal end that carries the port P'. In alternative arrangements, the bag B' may also be used in a hybrid open-closed system wherein the bag is delivered with a concentrate that is hydrated or mixed with other components a user may desire to add for administration with the system.

In the configuration depicted in FIG. 2, the bag B' also includes a sidewall SW' that encloses an interior volume V' for containing a fluid. The bag B' further incorporates a neck N' with a finish F' terminating in a port P'. The post P' may include an end cap or connector CN' and sealed with removable and/or pierceable seal S', which seal S' may be formed from a pierceable septum.

In this arrangement, the seal or septum S' is penetrated to communicate fluid, typically an intravenously administered fluid, with a legacy spike LS' having a distal extent D' formed with a sharp or substantially pointed end E' formed as a legacy spike diameter SD' ramps down to the pointed end E', many types of which are well-known to the various IV fields of art. The legacy spike LS' forms a part of an administration set AS' and may be carried from a connector C' that is in fluid communication with a tube T' that extends to a fluid recipient. A user or fluid recipient may pierce the seal or septum S' with the legacy spike S' to establish the fluid communication.

Referring next to FIG. 3, another variation of RTH receptacles is shown. Here an RTH rigid bottle B" is depicted, which also includes a sidewall SW" that encloses an interior volume V" for containing a fluid. The rigid bottle B" may be used in open and closed system configurations and will incorporate a neck N" extending to a finish F" terminating in a rim R" that defines a fluid communication port P". The finish F" may carry or integrally incorporate an end cap or connector CN" that may define the port P". The port P" may be sealed with a removable or pierceable sealing membrane, seal, and/or septum S".

Here again, an administration set AS" may include tubing T" extending to a fluid recipient to communication fluid from the rigid bottle B". A connector C" is typically connected to the tubing T" and may carry a legacy spike LS", which can pierce the seal or septum S" to establish the fluid communication.

With continued reference to the various figures, and now also to FIGS. 4, 5, and 6, further enlarged views of certain prior art components are depicted for further illustration. FIG. 4 is an enlarged view of the rigid bottle of FIG. 3, which shows the neck N" and finish F" of the bottle B", and with the rim R" carrying the fluid seal membrane or septum S" affixed to the rim R".

The detail view of FIG. 5 shows an enlarged view of the neck N", rim R", port P", and seal or septum S". Cross-sectional view 6-6 illustrates the relationships of these components. View 6-6 also shows the seal or septum S", to have a low-internal-pressure-induced, curved lower surface as may be used with film seal membranes and seals S" that seal the interior volume V" in a vacuum. View 6-6 also identifies an additional seal or septum material SM, which can extend within neck N" much like a stopper or cork used in other applications.

Despite many attempted improvements over the years, manufacturers, distributors, consumers, and users of such fluid receptacles, containers, bottles, bags, and the connector assemblies and administration sets have continued to experience a number of difficulties and challenges, and continue to strive for improvements.

In one example of such challenges, users and fluid recipients have been known to use administration sets and components inadvertently that are intended for IV fluid administration with enteral fluid administration products. This has resulted in frustrated fluid recipients and users that have been thwarted in their attempts to administer enteral fluids.

Those having skill in the field have recognized that the smaller fluid pathway diameters of IV administration sets, connectors, and systems are unsuited for rapid enteral indwelling delivery of more viscous and dense enteral fluids. Those attempting to interconnect IV fluid administration connectors, systems, and administration sets to enteral fluid containers, receptacles, bottles, pouches, and bags, have also experienced fluid leaks that waste valuable enteral products.

Additional frustrations can be experienced by users and fluid recipients that attempt to administer IV fluids using incompatible enteral administration sets, connectors, and systems. Such incompatible and unintended uses, applications, and circumstances create obstacles to effecting otherwise desirable administration of desired fluids at preferred flow rates to fluid recipients, and may also introduce leaking of valuable IV products unintended for delivery and administration using such enteral fluid delivery systems.

One of the problems that has been seen is that legacy IV spikes such as legacy spikes LS', LS can sometimes be forcibly introduced into enteral connectors, systems, and administration sets. While many variations of such legacy IV spikes LS', LS" have found their way into the marketplace, a substantial majority of such legacy IV spikes are usually in the range of about 1.00 inches to about 1.25 inches in length from shoulder to pointed tips. Such legacy IV spikes are also usually formed to have a diametrical diameter that is approximately between about 0.250 and about 0.375 inches.

In enteral administration sets, connectors, and systems that use the aforementioned seals and septums, there are limited means by which to prevent an unskilled user or fluid recipient from ignoring incompatibility issues and the undesirability of using inappropriate combinations of components. Further, prior components can present inconveniences wherein legacy spikes may puncture a seal, septum, and/or sealing membrane, such as a polymeric or plastic or foil seal, in a way that causes the seal, septum, and/or sealing membrane to seal against the exterior diameter of the legacy spike after puncture or piercing. Another challenge to users and fluid recipients includes the legacy spike causing particles or pieces of the seal, septum, and/or sealing membrane to separate during piercing and puncture and thereafter becoming lodged and impeding fluid communication in a fluid pathway.

Some manufacturers have attempted to introduce features to prevent users and fluid recipients from employing inappropriate combinations of connectors and systems in untoward, incompatible applications. Some such features were aimed at introducing proprietary connection components that cannot accept connectors from other manufacturers.

However, this approach often only compounded the frustrations experienced by users and fluid recipients who experienced leaks when forcibly connecting the incompatible components. Even with seemingly compatible components from assertedly cooperative manufacturers, such prior components have offered challenges to the users.

One challenge that has persisted as reported by such users includes that it is often impossible even for skilled users and fluid recipients to discern when connectors are properly joined together to establish fluid flow. These same and additional users have also repeatedly voiced concerns that the prior art connectors make it difficult to assemble even cooperative components in view of the manufacturer introduced, proprietary connector complexities, which purport to prevent incompatible connections.

Those with knowledge in the field of enteral administration sets, connector assemblies, and systems have long sought to create new components and systems that address the need to prevent incompatible connections, but which do not impose added challenges to the user and fluid recipients. Despite the prior art advances in many areas of connector design that have attempted improved connectability, designers have also sought improved ways to replace unintuitive complexities with intuitively easy-to-use features that reduce user confusion.

What has long been needed in the field of art of enteral connector assemblies and systems is a connector assembly and system that addresses the many issues surrounding prior designs. More specifically, an improved connector assembly and system is needed to increases the probability that experience and inexperienced users and fluid recipients will be unable to establish fluid connections between inappropriate connectors, systems, and administration sets. Even more preferably, it is important to enable users and fluid recipients to have increased confidence during operation of such connector assemblies and systems that they have properly connected components and properly established fluid communication.

Even in view of the many attempts in the prior art to produce effective enteral fluid delivery sets that include connector assemblies and systems, manufacturers, distributors, users, fluid recipients, and those skilled in the relevant fields of technology have remained convinced that further improvements are possible. The market continues to seek improved and easier-to-use connector assemblies and systems that are substantially less susceptible to being forcibly introduced into incompatible and inappropriate applications. Under ideal circumstances, such improvements would also incorporate all of the advantages of the prior art, while withstanding the unexpected and incompatible, forcible use attempts.

SUMMARY OF THE INVENTION

Many of the problems of the prior art have been overcome with the instant invention, and sought after improvements in the field have been achieved in new and novel ways. The improvements described herein enable previously unavailable features including considerably improved ways to prevent, if not sometimes entirely eliminate, incompatible and inappropriate connections between the inventive enteral connector assemblies and systems, and non-compatible components such as legacy IV spikes.

The innovative connector assemblies and systems also introduce new and more effective positive control connection capabilities, which will minimize the possibility for connector leaks, maximize the convenience of use for the user and/or fluid recipient, and increase the likelihood that such connector assemblies and systems will only be used with compatible components and with intended applications. Such improvements and advances in the art are also further augmented by new types of visual cues, and superior modes of dual-mode connect-disconnect tactile user feedback mechanisms.

In one preferred configuration of the invention, an enteral connection system is adapted to communicate fluid between a receptacle such as a fluid container, bottle, pouch, and/or receptacle, and an enteral administration or feeding set. The receptacle is formed from at least one or a plurality of sidewalls that cooperate to define an interior volume for containing a fluid.

The sidewalls also extend to a finish that forms a neck that extends to a rim defining a fluid communication port. An imaginary plane is also defined by the substantially planar rim, which is also referred to herein as a receptacle seal plane. An optional sealing membrane or seal or septum may cover and/or be formed about the rim to seal the fluid contents of the interior volume prior to communication or dispensing of the fluid.

Preferably, the enteral connection system also further includes an end cap or connector that is receivable about the fluid communication port. The connector or end cap is also formed with at least one cap wall that defines an interior lumen or fluid pathway for communicating the fluid between the receptacle and the administration or feeding set. The interior lumen and end cap are also preferably defined with a proximal end that is receivable about the fluid communication port, and a substantially opposite distal end.

Also preferably, the interior lumen defines generally adjacent to the proximal end a cap seal port defined by a periphery of the end cap wall. The periphery of the end cap wall further defining a cap seal plane. It may be optionally preferred that the end cap when received about the fluid communication port of the receptacle or container is ideally positioned to enable the cap seal plane and the receptacle seal plane to be substantially coplanar.

More preferably, the cap wall has an interior face or surface that supports and carries at least one spike barrier substantially proximate to the proximate end of the end cap wall and interior lumen. Even more preferably, the spike barrier substantially spans the interior lumen. The spike barrier also establishes an interstice defined and bounded about a circumference by the at least one cap wall, and at ends by the spike barrier and the cap seal plane.

The spike barrier also further preferably includes a periphery that defines and circumscribes at least one barrier port through the barrier. More preferably, the barrier port is in fluid communication with the interior lumen and enables fluid communication through the barrier. Also preferably, the periphery establishes a barrier geometry that further defines a barrier keyway that is shaped and sized to be incompatible for passage there through of one or more legacy spikes.

By substantially spanning the interior lumen or fluid pathway, the spike barrier creates a fence, barricade, and/or barrier to unintended or forcible use of incompatible connectors, which can include for purposes of example but not limitation, legacy spikes. A further feature of the spike barrier is to simultaneously enable fluid communication through the interior lumen or fluid pathway, and past the barrier only when used with compatible connector assemblies and systems.

Even more preferably, the bounded interstice establishes a legacy distance and a legacy diametrical dimension. The legacy distance preferably spans an axis line that approximately extends perpendicularly between the cap seal plane and the spike barrier. The legacy diametrical dimension preferably spans a smallest distance across the diameter of the interior lumen between the at least one sidewall or sidewalls. More preferably, the legacy distance and legacy diametrical dimension are approximately perpendicular.

In other possibly useful variations, the interstice is bounded by the cap wall to have at least one legacy diametrical dimension that is less than diametrical dimension of at least one legacy spike.

It is optionally preferred that the legacy distance exceeds a length of at least one legacy spike, which prevents the at least one legacy spike from extending through any port or keyway of the spike barrier and through the interstice to the cap seal plane. It is also preferred that the legacy diametrical distance optionally is less than the diameter of at least one legacy spike.

In this way, the spike barrier and/or the interstice, either alone and/or in combination can prevent legacy spikes and other incompatible connectors from establishing fluid communication with a sealed receptacle, container, bottle, pouch, and/or bag that incorporates the innovative connector assembly and system.

Additional modifications to the novel connector assemblies and systems may further include the end cap to have at least one partial turn groove or thread that may be formed about a portion of the cap wall or proximate thereto or in cooperation therewith. Those skilled in the relevant mechanical arts will recognize such partial turn grooves or threads as enabling partial turn connections of such connectors and systems with various fluid receptacles. Enabling connections with less than full turns increases the convenience to users and fluid recipients, who can then join the components more quickly and conveniently.

Other preferable and optional variations of the invention contemplate the connector assembly and system to further have and/or cooperate with an interconnect that is or that can be connected to an administration or feeding set. Preferably, the interconnect is movable and receivable about the end cap and/or receptacle or container between received and disconnected positions. The interconnect also preferably has at least one optional key that is shaped similarly and to be cooperative with the partial turn groove. In operation, the key and groove can thereby cooperate, when assembled and connected by a user, to translate the interconnect between received and disconnected positions relative to the end cap.

In another optional or preferred modification, the interconnect may include at least one and/or a plurality of piercing tines that can be carried from the interconnect. Preferably, the tines extend outwardly from the interconnect towards the spike barrier, when the interconnect is joined to the end cap. More preferably, the tines are configured to have a cross-sectional geometry substantially similar to the barrier keyway geometry so as to be receivable through the barrier keyway.

In further modifications of any of the preferred configurations, the invention contemplates snap-on, snap-fit, and/or snap-in interconnect and end cap arrangements. In these arrangements, the at least one and/or plurality of piercing tines include one or more keyed tines in combination with, in addition to, as a replacement, and/or formed as the piercing tines. More preferably, such one or more keyed tines in a cross-section may form and/or define the cross-sectional geometry substantially similar to the barrier keyway geometry.

In other possibly preferred variations, the piercing tine or tines and/or one or more keyed tines are configured with a tine length that will extend beyond the cap and/or receptacle seal plane, when the interconnect is joined to the receptacle and end cap. In operation, a tip of the tine will penetrate and/or pierce any seal, septum, and/or sealing membrane carried from a rim of the container, which seals the receptacle, and which establishes fluid communication between the interconnect and the interior volume of the receptacle and/or container.

This arrangement will also accomplish a similar result for other alternative variations wherein the seal, sealing membrane, or septum is also carried from a surface of the end cap and/or spike barrier. It may also be optionally preferred that such tine tips are specially shaped and formed whereby the tine tips puncture or pierce or plow or tear open any seal, septum, and/or sealing membrane in a way that establishes a fluid pathway wherein the seal, septum, and/or sealing membrane does not seal against the tine, and wherein the puncture does not cause particles or pieces to separate from the seal, septum, and/or sealing membrane.

In yet other sometimes preferred configurations, the interconnect may be adapted wherein the at least one key or keys are sized and shaped to be operative to obstruct the interconnect from being used with one or more legacy connectors. More preferably, the at least one partial turn groove of the end cap can be a female helical groove or thread, and the at least one key is a complementary helical male ridge. Even more preferably, the ridge and grooves are sized to have a shape, pitch, diameter, and other dimensions that are incompatible for use with legacy connectors such as IV administration connectors and other legacy enteral connectors that all may be unsuitable for use with the connector assemblies and systems of the invention.

The optionally preferred arrangements that incorporate such helical grooves and ridges may further have the pitch of the helical groove and the ridge selected to translate the enteral cap and interconnect between the received and disconnected positions in less than one turn, or as a result of only a partial turn of at least one of the enteral cap and the interconnect.

Further preferred configurations of the connector assemblies and systems may incorporate an optional feature wherein the at least one partial turn groove of the end cap also includes a substantially longitudinal portion, which is preferably approximately parallel to an axis of the interior lumen that follows the fluid pathway. More preferably, the longitudinal portion also includes an extent that has at least one partial turn detent.

The detent and/or the extent, alone or in combination, are preferably sized to receive and capture the at least one cooperative key upon receipt and a partial turn of the enteral cap. These features enable an haptic actuator capability operative to produce audible and/or vibrational tactile feedback to the user when the interconnect is connected and properly received against the end cap and receptacle.

Further possibly desired variations of the extent and detent can enable a disconnection deterrent capability, as well as a tactile feedback that is perceptible as an audible and/or vibrational alert to the user warning and/or confirming disconnection. Even more preferably, the extent and/or the detent can be sized and shaped to receive the cooperative key, but also to prevent release subsequent to capture for applications where it is desirable that the end cap and interconnect are inseparable once joined.

Most preferably, the cooperative key and extent are optionally shaped and sized to produce the audible and/or vibrational feedback having an amplitude that is easily perceptible to the intended user and/or fluid recipient.

These variations, modifications, and alterations of the various preferred and optional embodiments of the inventive container may be used either alone or in combination with one another and with the features and elements already known in the prior art and also herein described. Such embodiments can be better understood by those with knowledge and skill in the relevant fields of technology arts with reference to the following detailed description of the preferred embodiments and the accompanying figures, illustrations, and drawings.

BRIEF DESCRIPTION OF THE DRAWING(S)

Without limiting the scope of the present invention as claimed below and referring now to the drawings, figures, modified scale section views, and modified scale detail views, wherein like reference characters and numerals, and like characters and numerals with primes and double-primes, across the drawings, figures, and views refer to identical, corresponding, or substantially like and equivalent elements, methods, components, features, and systems:

FIG. 4 is an enlarged detail view of the rigid liquid product bottle of FIG. 3 that shows the lower finish and neck of the bottle having a fluid seal membrane or barrier affixed to a rim of the neck.

FIG. 5 is an enlarged detail view of the neck and seal of the bottle of FIG. 4.

FIG. 6 is an enlarged and rotated section view, taken along section line 6-6 of FIG. 5, of the neck and seal of the substantially rigid bottle.

Figure 1:
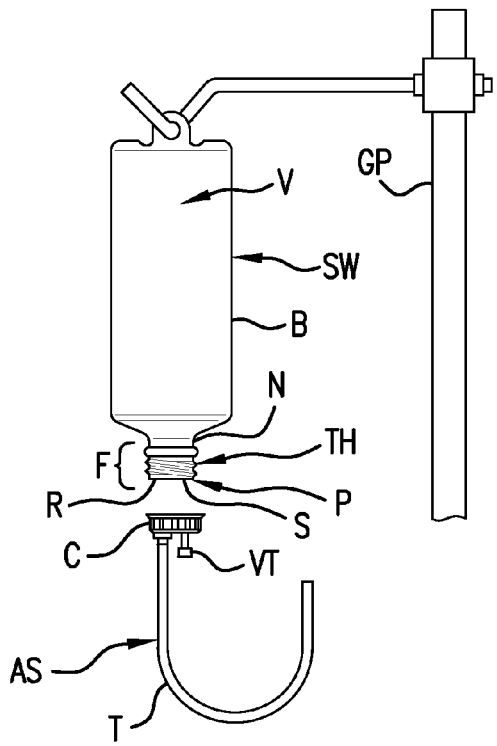
FIG. 1 is an elevation view of a prior art, ready-to-hang (RTH), prefilled, closed-system collapsible flowable product or fluid or liquid product bag, cap, and connector fluid tube set assembly hung from a gravity elevation pole.
Figure 2:
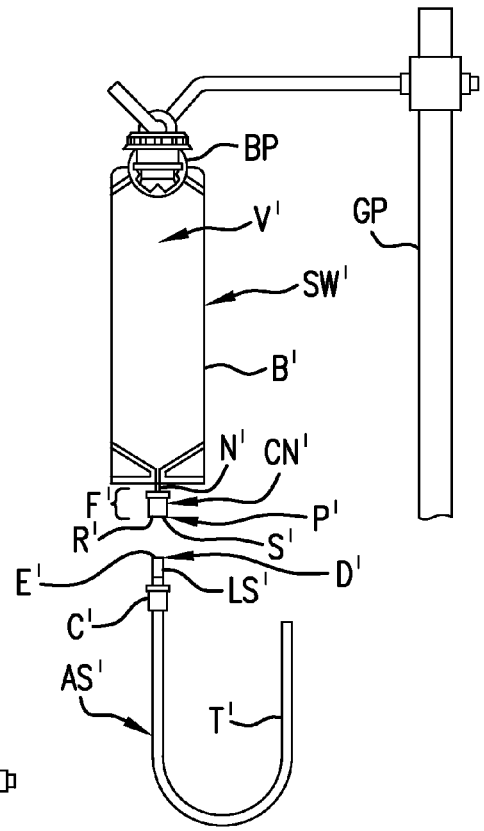
FIG. 2 is an elevation of a prior art, RTH, fillable, open-system collapsible liquid product bag, cap, and legacy spike connector fluid tube set assembly hung from a gravity elevation pole.
Figure 9:
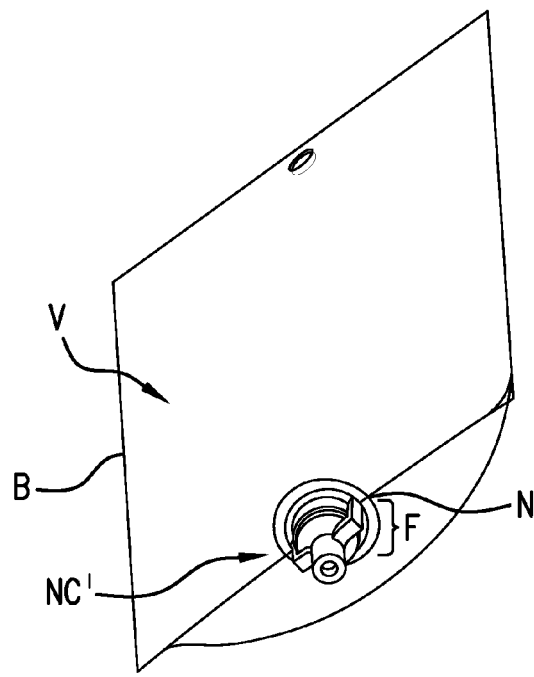
Figure 10:
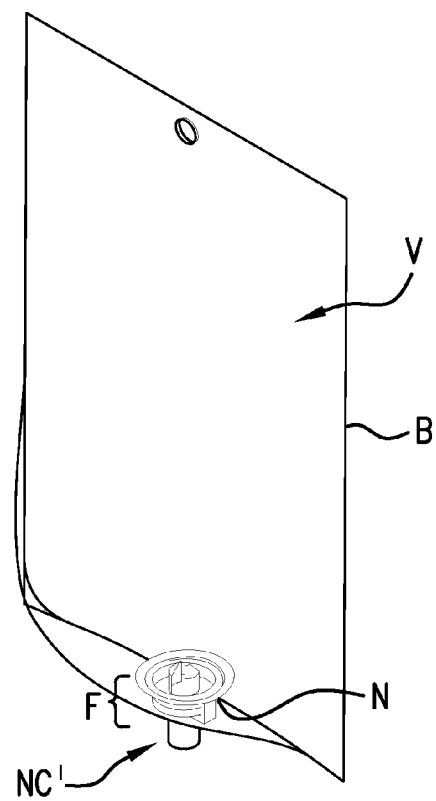
Figure 11:
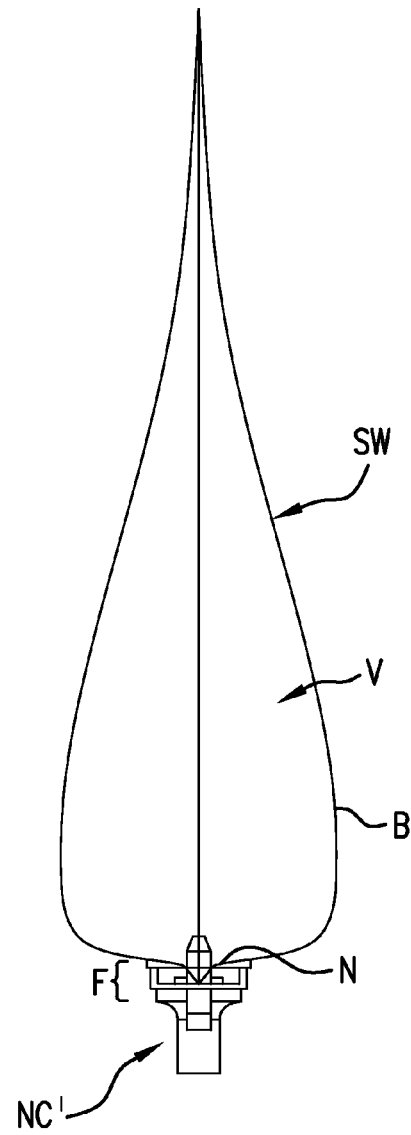

FIGS. 9, 10, and 11 are perspective and side views of a collapsible bag similar to those of FIG. 1, and assembled to another embodiment of an enteral connector assembly and system.

FIGS. 12, 13, 14, 15, 16, and 17 show various elevation and side views of another embodiment of an inventive enteral connector assembly and system adapted for use with collapsible bag containers such as those shown elsewhere herein.

FIGS. 18, 19, 20, 21, and 22 depict detail elevation and side views in modified scale of elements of the embodiments of FIGS. 12-17, with certain structure removed for illustration purposes.

Figure 22:
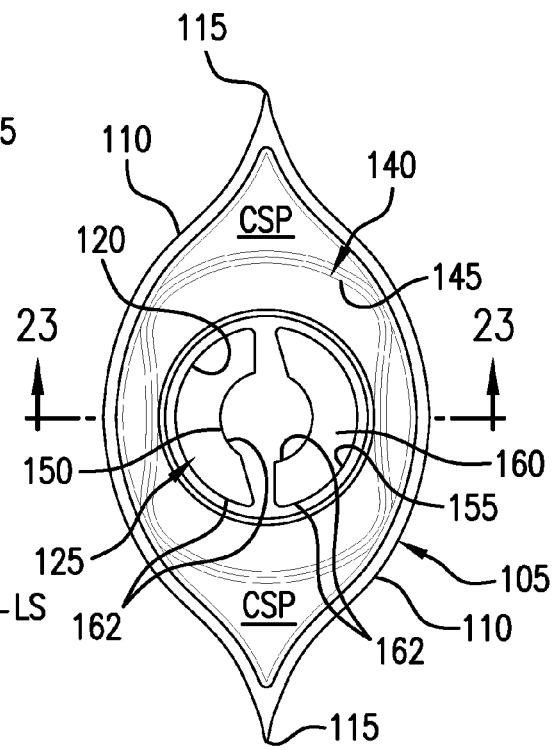
Figure 23:
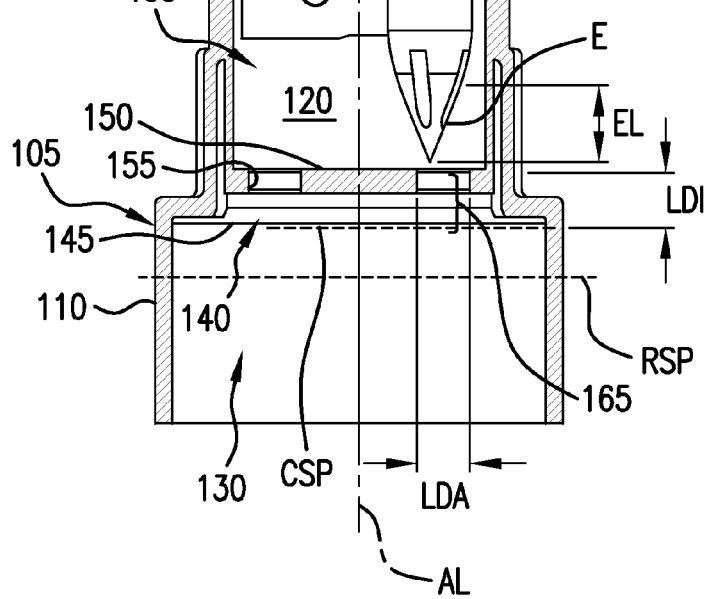

FIG. 23 is an enlarged and rotated section view, taken approximately along section line 23-23 of FIG. 22, and also showing an incompatible legacy intravenous spike.

Figure 24:
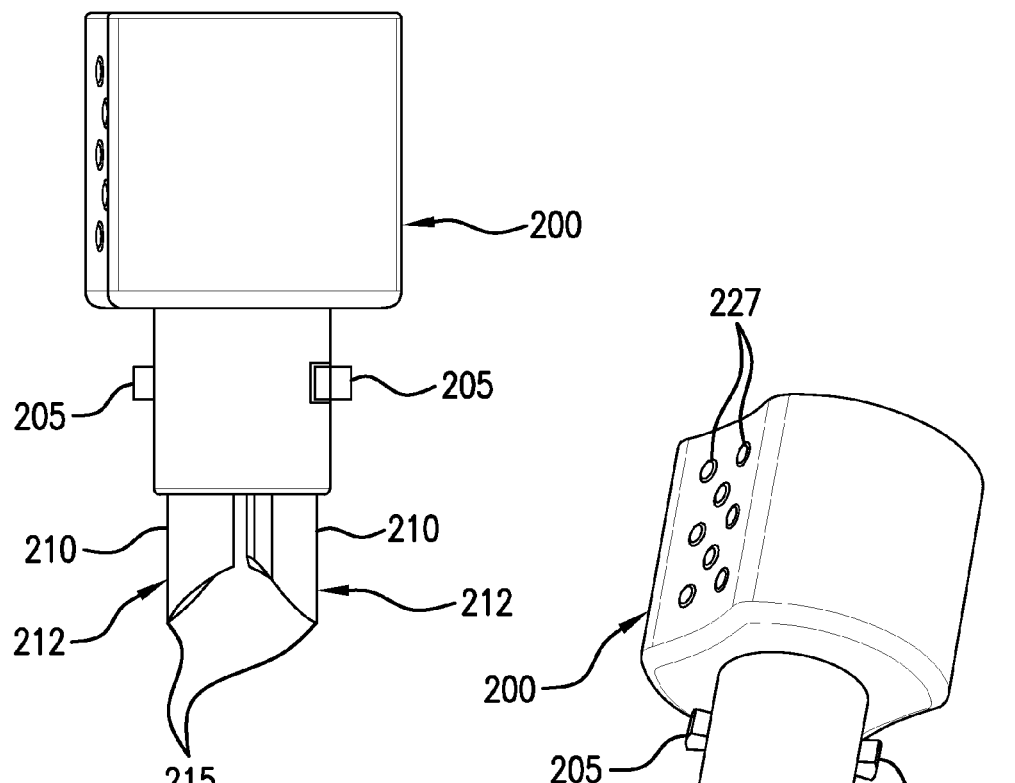
Figure 25:
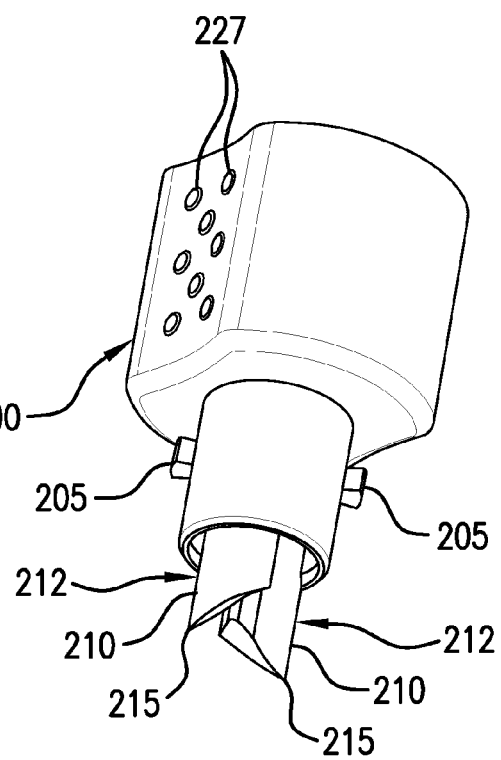
Figure 26:
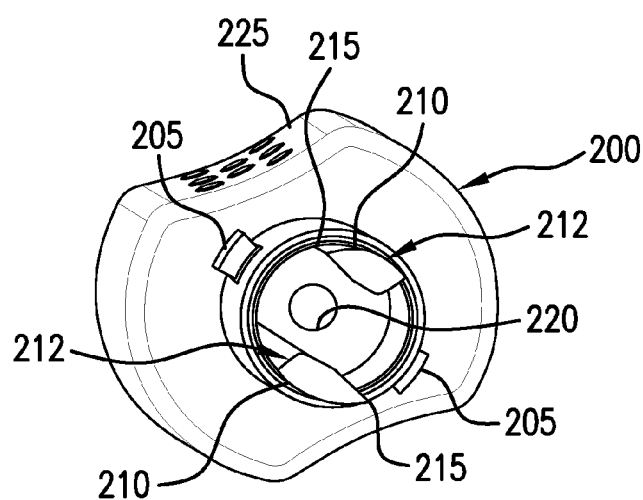
Figure 27:
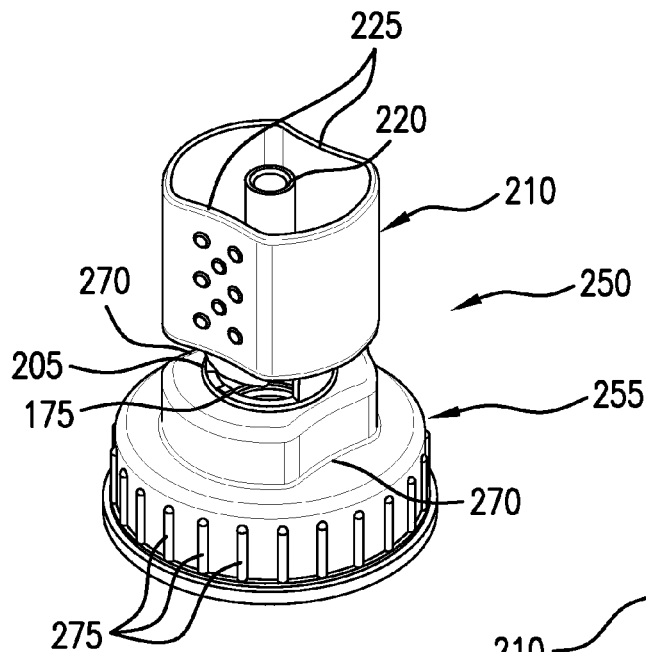
Figure 28:
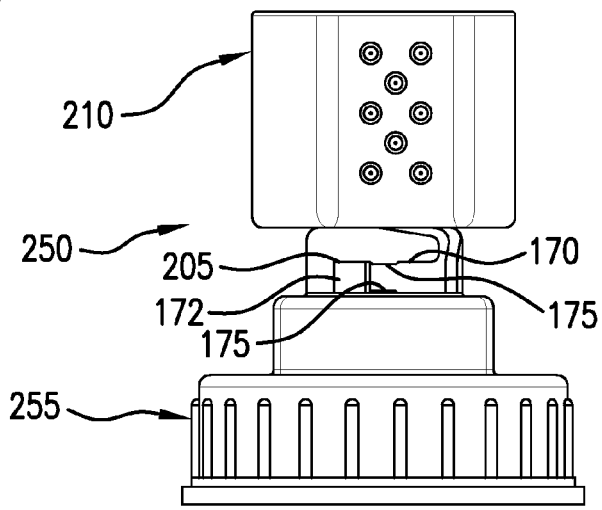
Figure 29:
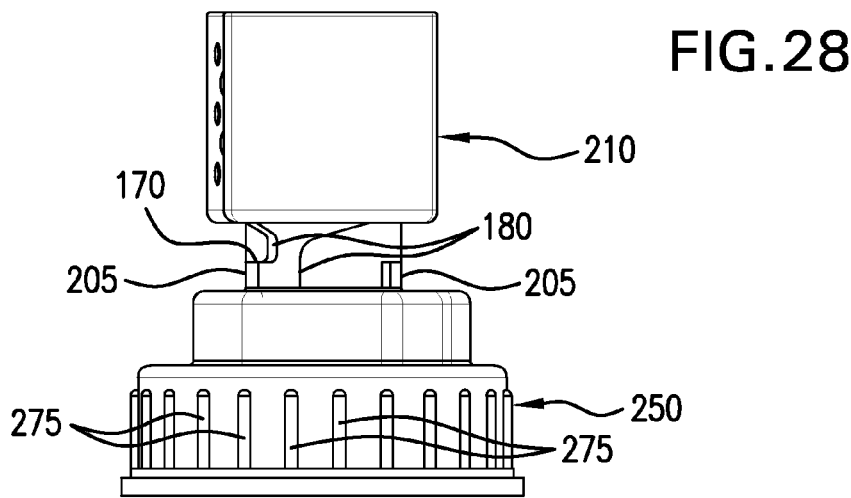

FIGS. 24, 25, and 26 show various elevation and side details views of the embodiments of FIGS. 12-17 and 27-30, but with certain structure removed for continued illustration purposes.

FIGS. 27, 28, 29, 30, 31, 32, 33, and 34 illustrate another embodiment of an enteral connector assembly and system adapted for use with rigid ready-to-hang bottles.

Figure 34:
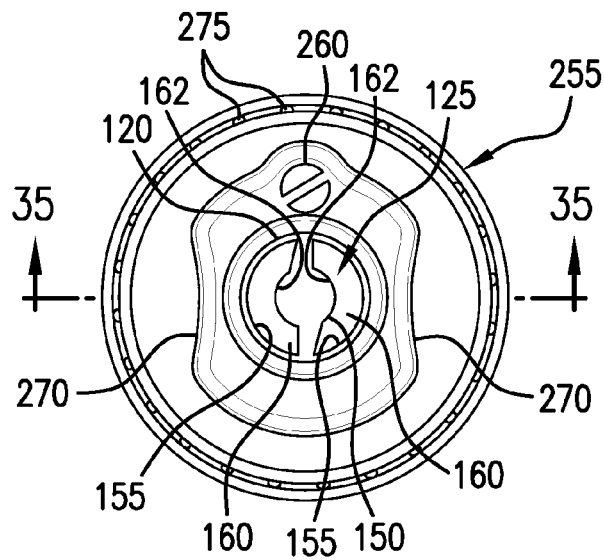
Figure 35:
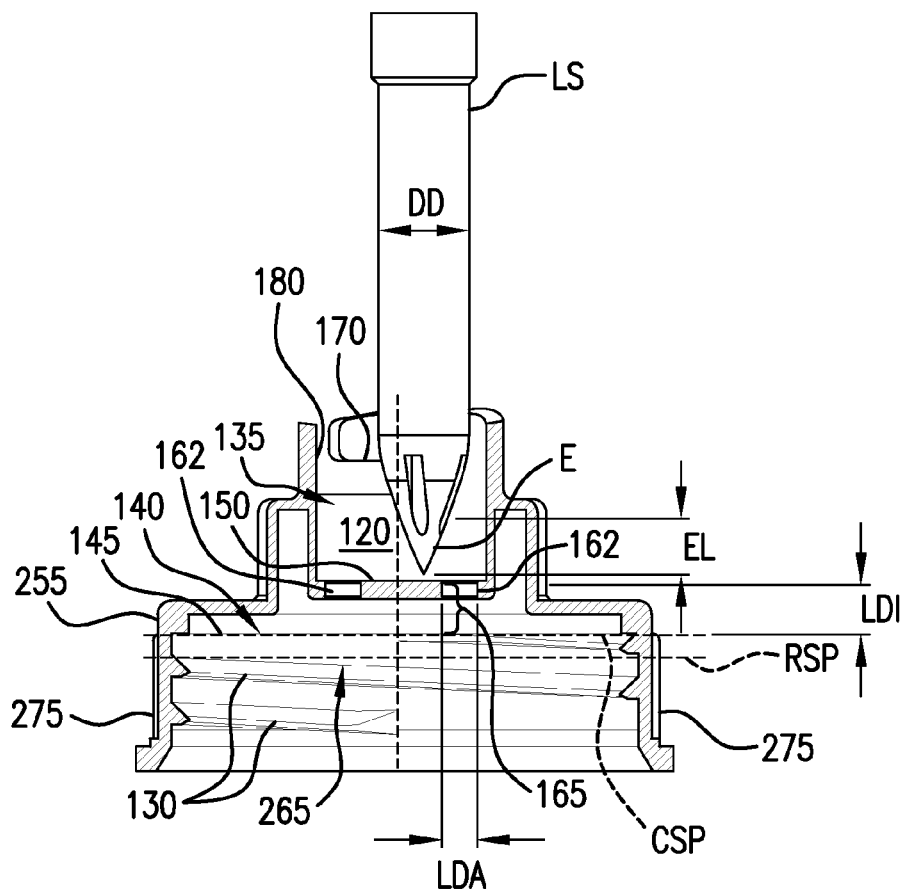
Figure 36:
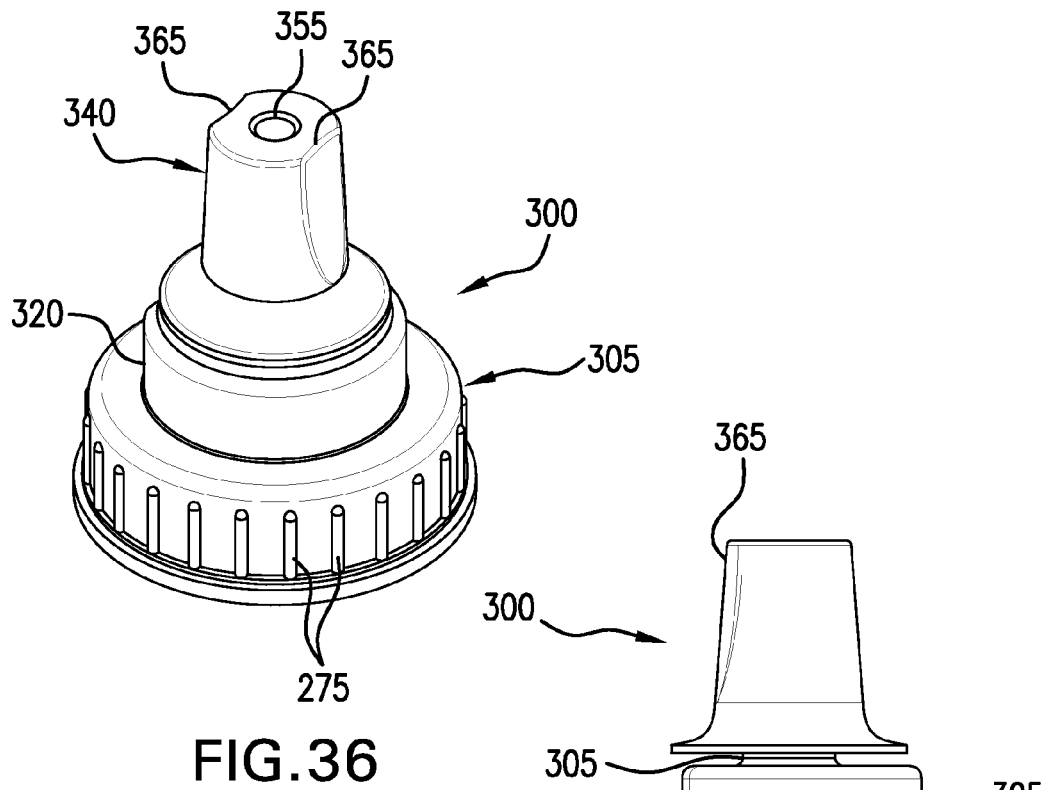
Figure 37:
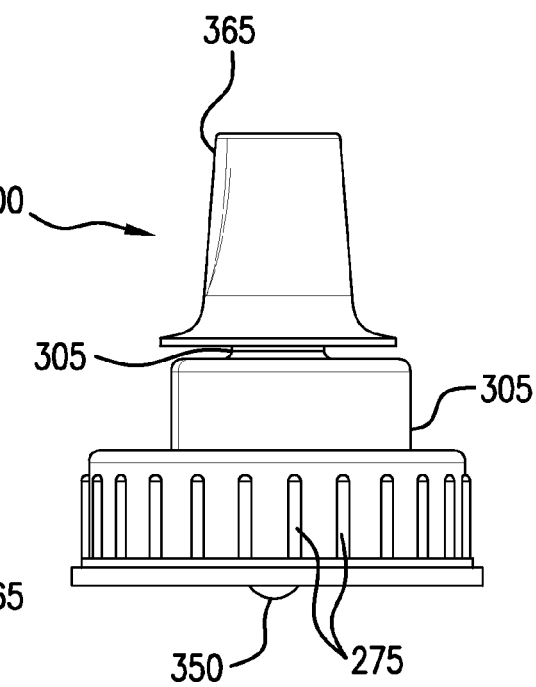
Figure 38:
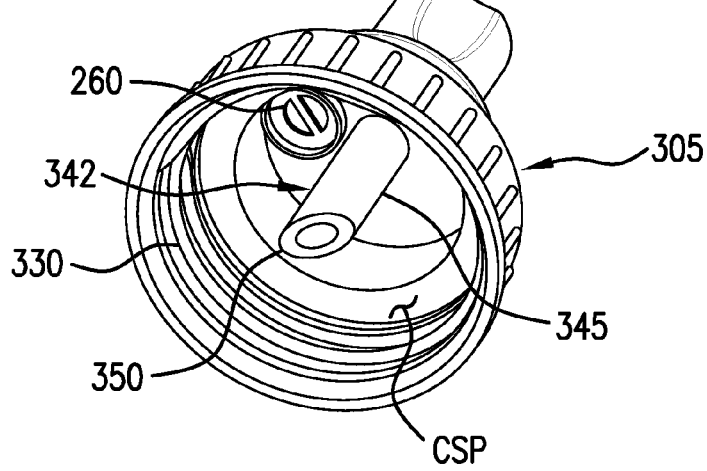

FIG. 35 is an enlarged and rotated section view, taken approximately about section line 35-35 of FIG. 34, and also showing an incompatible legacy intravenous spike.

FIGS. 36, 37, 38, and 39 are elevation and side views that describe another embodiment of a connector assembly and system.

Figure 39:
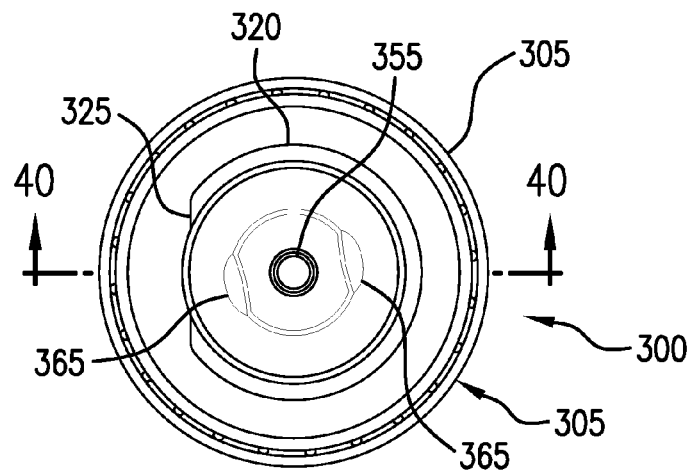
Figure 40:
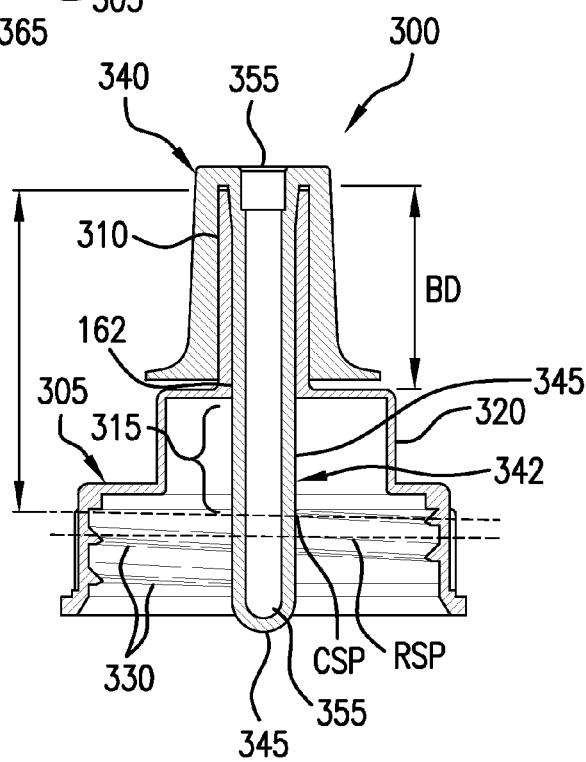

FIG. 40 is an enlarged and rotated section view, taken substantially along section line 40-40 of FIG. 39.

Figure 41:
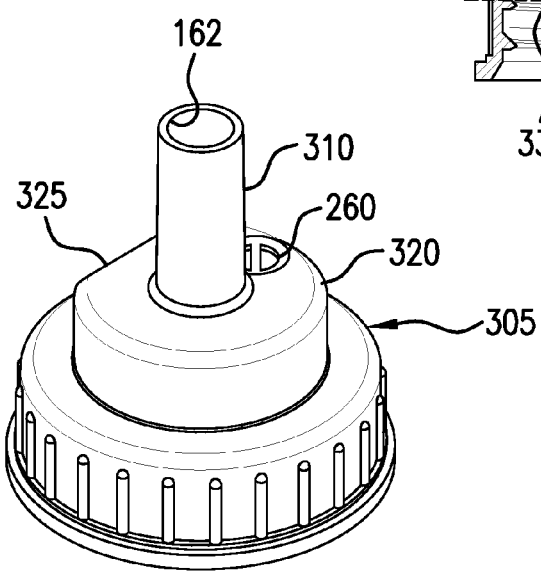
Figure 42:
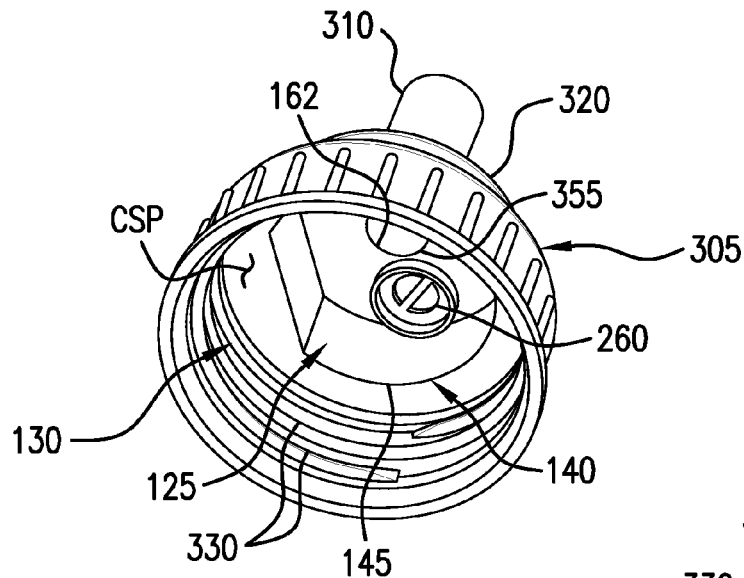
Figure 43:
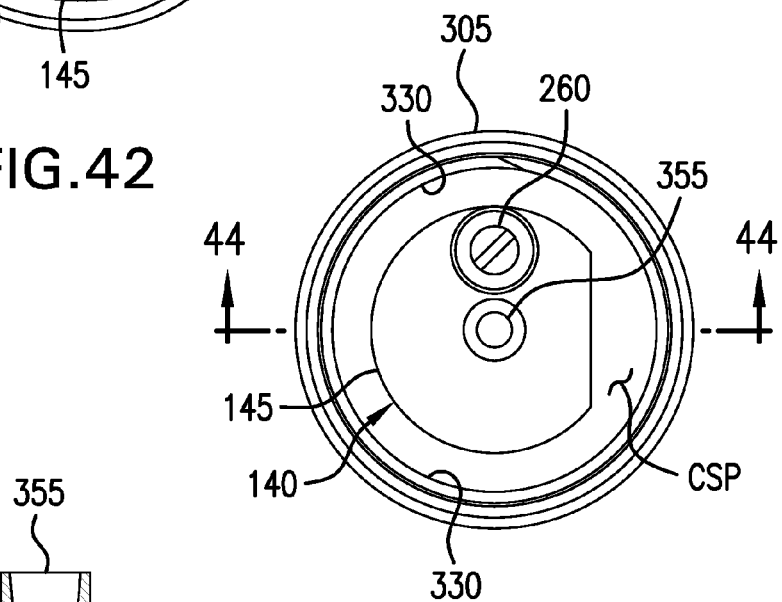

FIGS. 41, 42, and 43 depict detail elevation and side views in varied scale of the embodiments of FIGS. 27-40 with various elements removed for further depictions.

Figure 44:
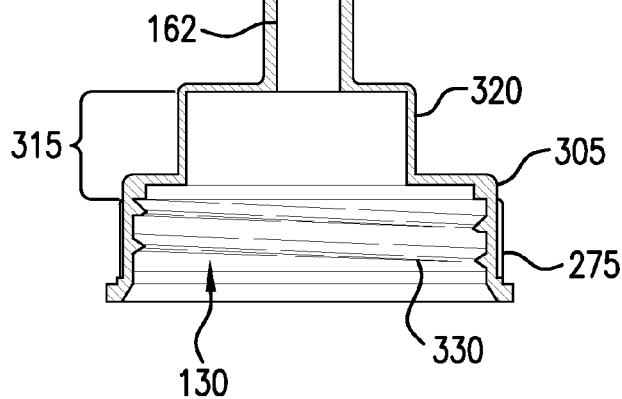

FIG. 44 is an enlarged and rotated section view, taken approximately about section line 44-44 of FIG. 43.

Figure 45:
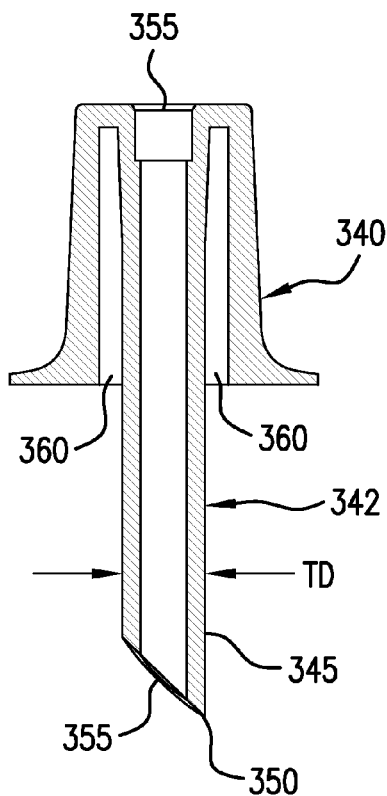

FIG. 45 is a detail section of assembly section view 40.

Figure 46:
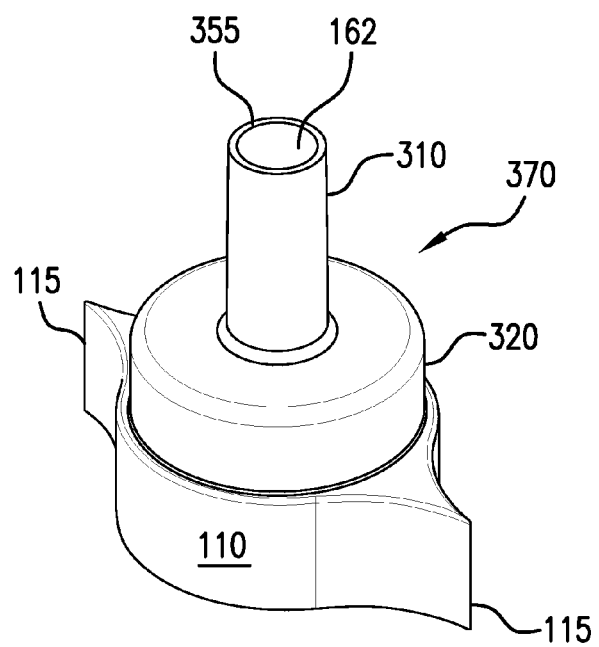
Figure 47:
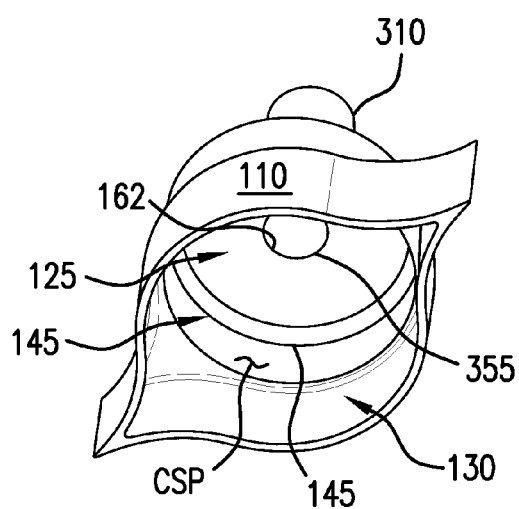
Figure 48:
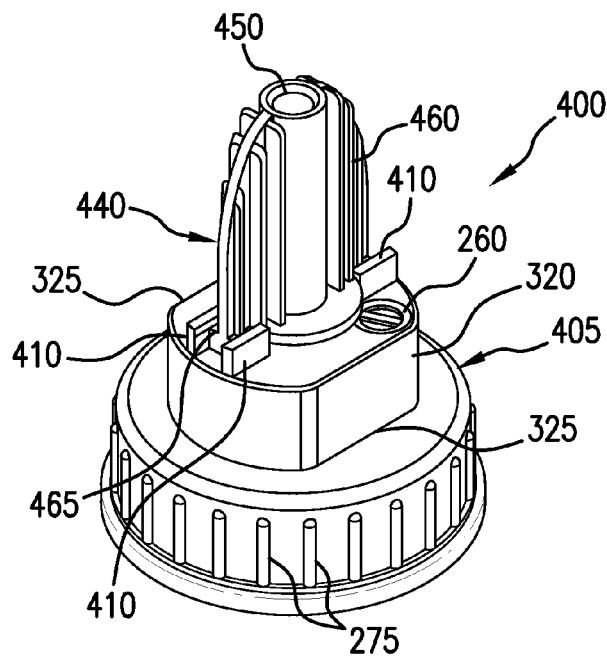
Figure 49:
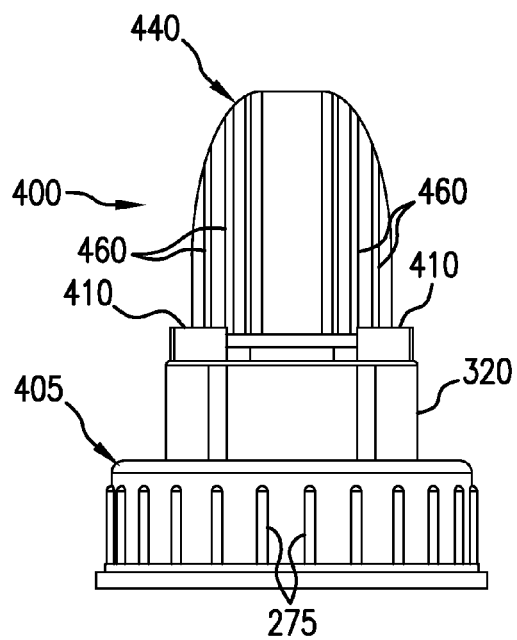
Figure 50:
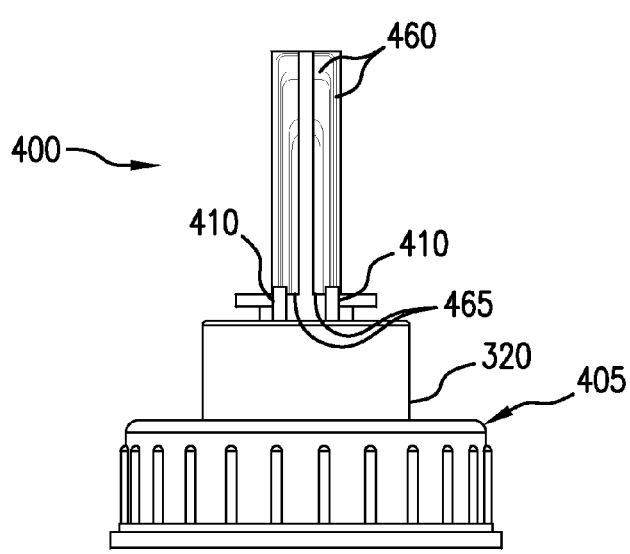
Figure 51:
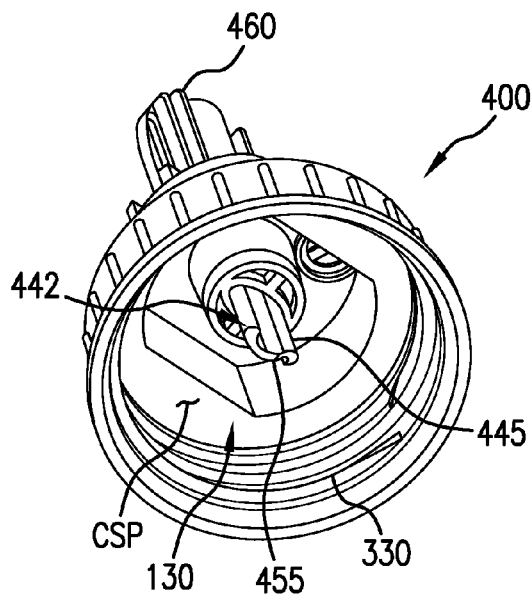
Figure 52:
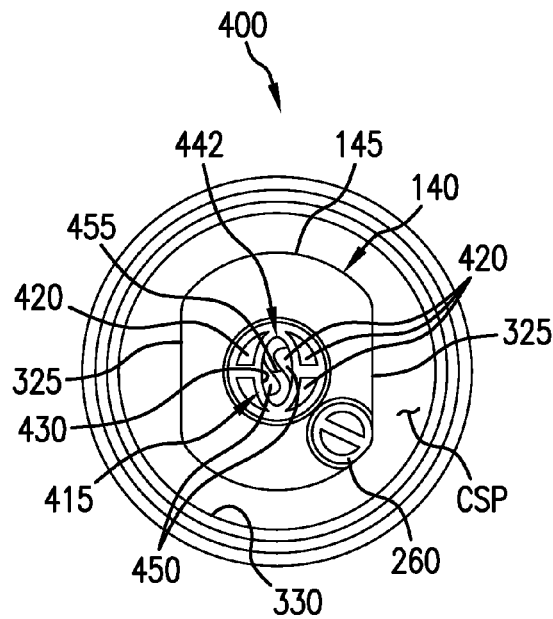

FIGS. 46 and 47 are elevation views in modified scale of a modified embodiment of the embodiments depicted in FIGS. 41-44.

FIGS. 48, 49, 50, 51, 52, and 53 are side and elevation views of another configuration of a connector assembly and system.

Figure 53:
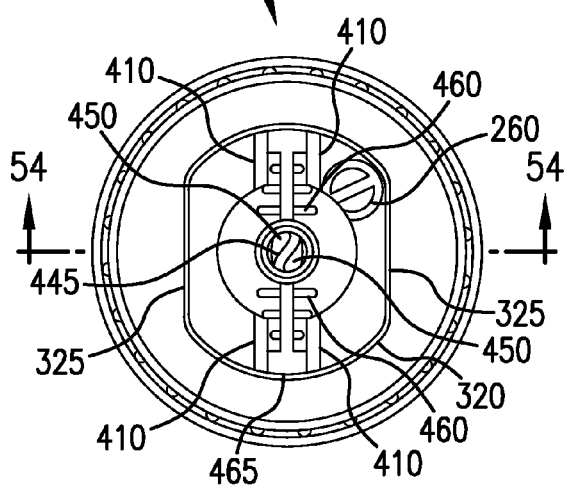
Figure 54:
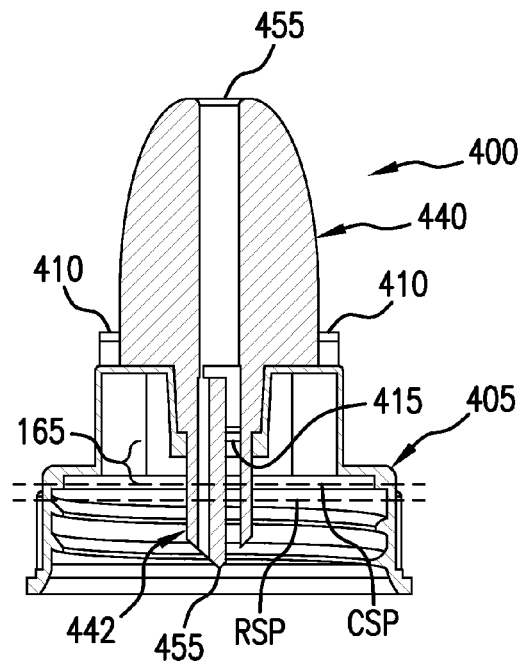

FIG. 54 is an enlarged and rotated section view, taken approximately about section line 54-54 of FIG. 53.

Figure 55:
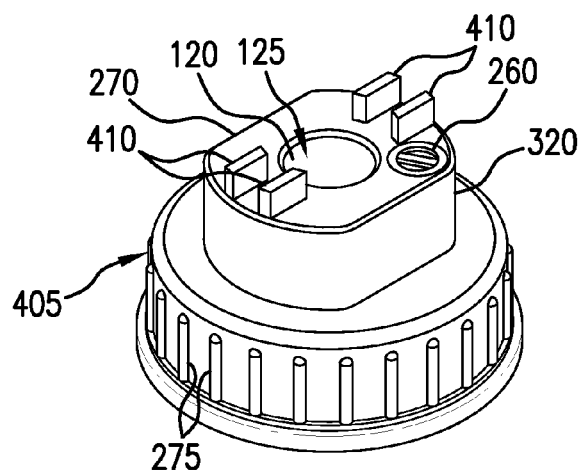
Figure 56:
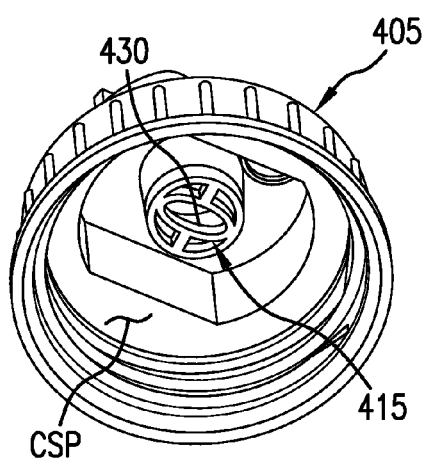

FIGS. 55 and 56 are detail elevation views in modified scale of the embodiments of FIGS. 48-53 with various elements removed for continued depictions.

Figure 57:
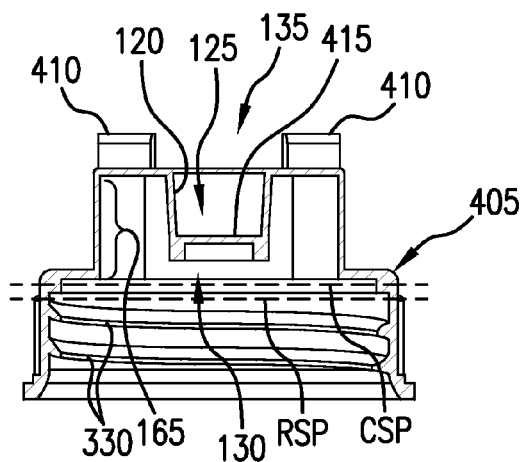

FIG. 57 is a detail section view of FIG. 54 with certain structure removed for added descriptions.

Figure 58:
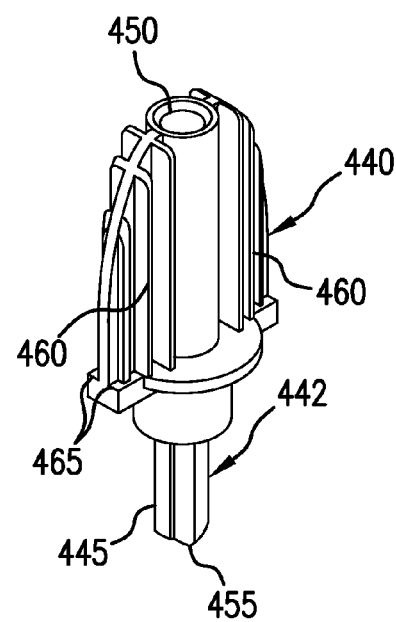
Figure 59:
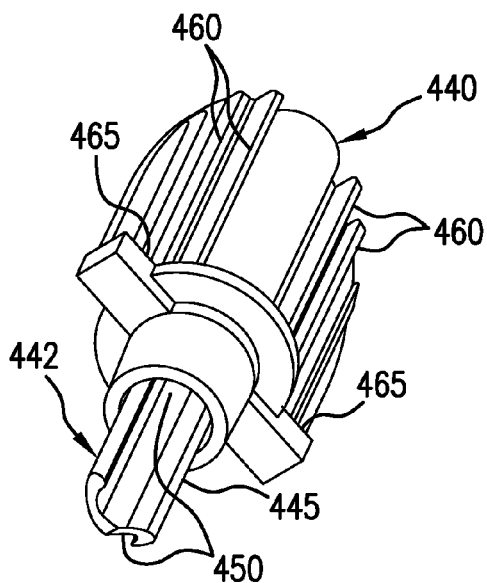

FIGS. 58 and 59 are rotated detail elevation views in varied scale of the embodiments of FIGS. 48-53 with certain structure removed for further discussion.

Figure 60:
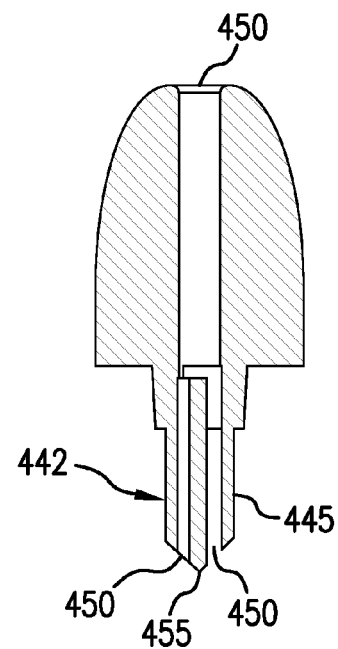
Figure 61:
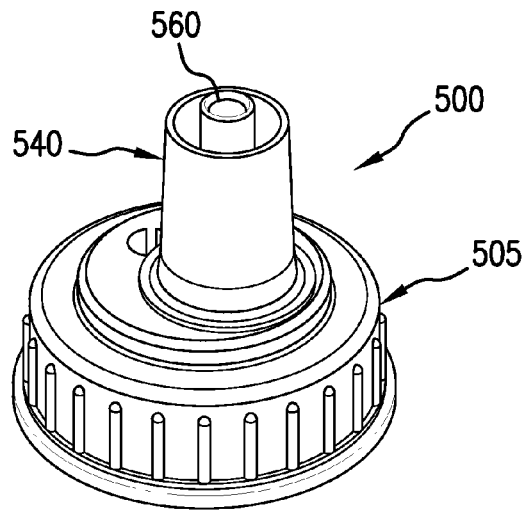
Figure 62:
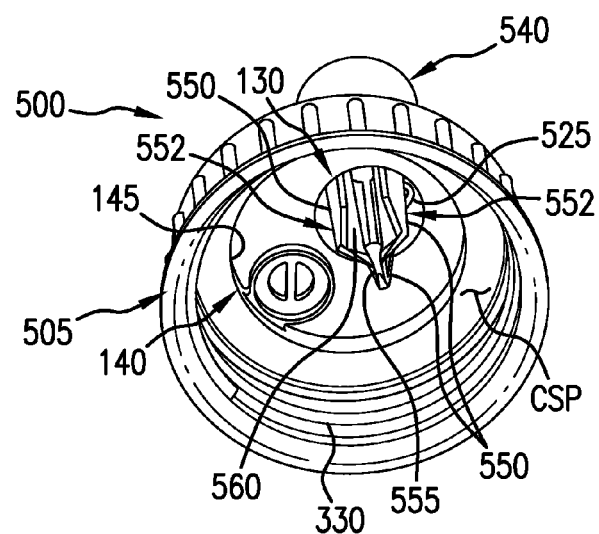
Figure 63:
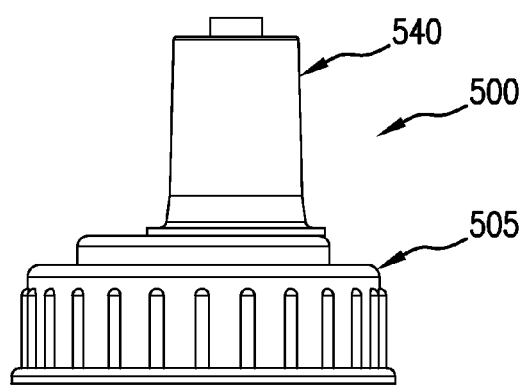

FIG. 60 is a detail section view of FIG. 54 with certain structure removed for added descriptions.

FIGS. 61, 62, 63, 64, and 65 are elevation and side views of yet other variations of connector assemblies and systems.

Figure 64:
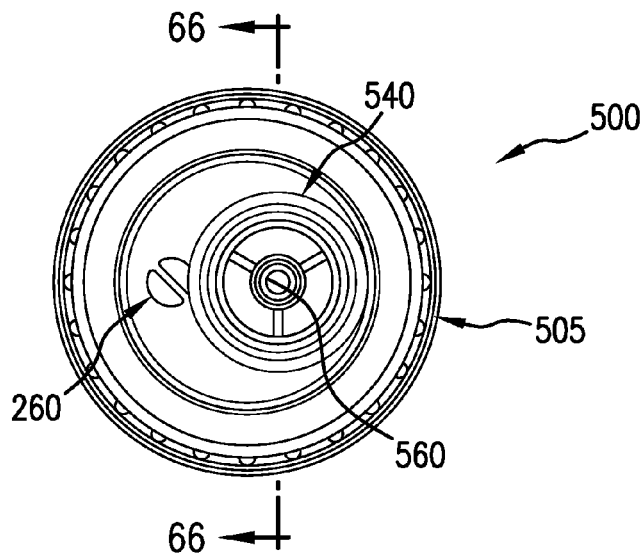
Figure 65:
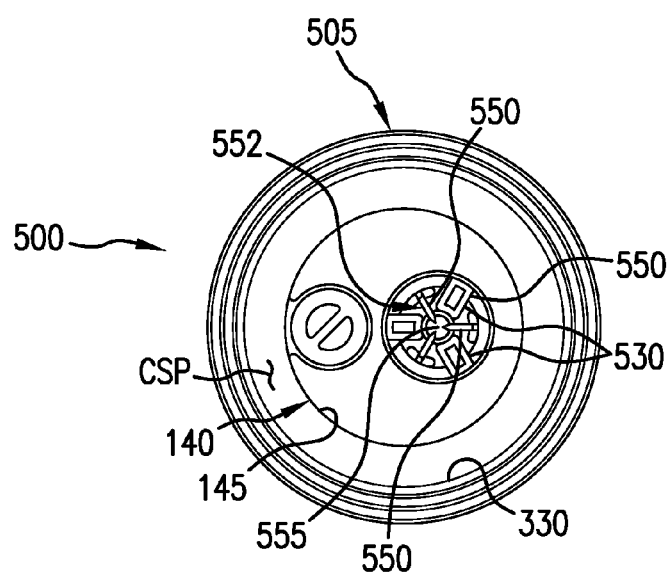
Figure 66:
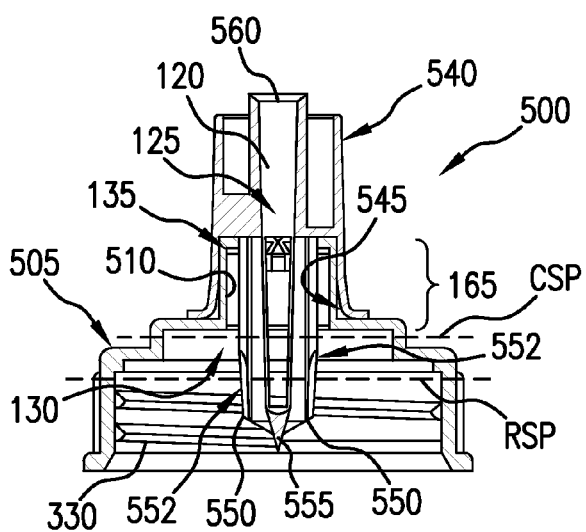
Figure 67:
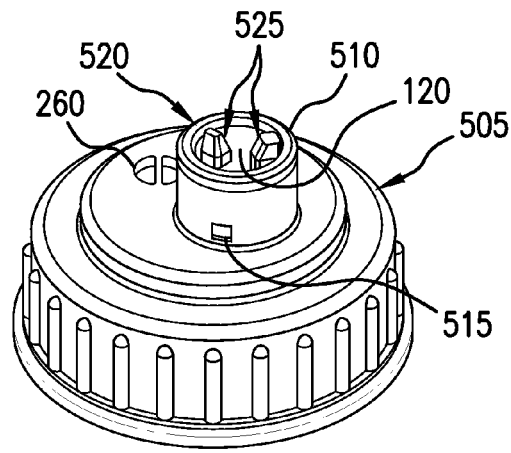
Figure 68:
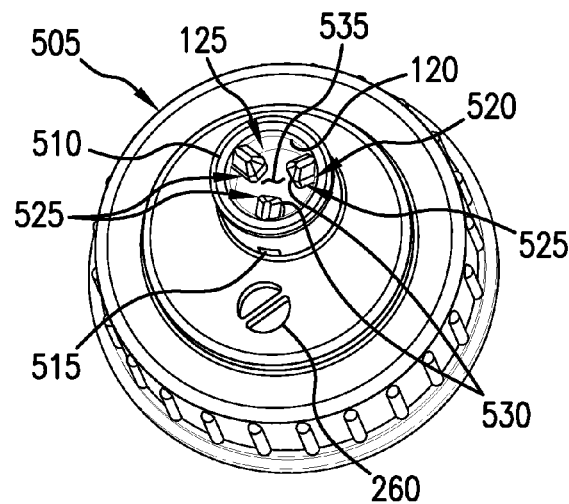
Figure 69:
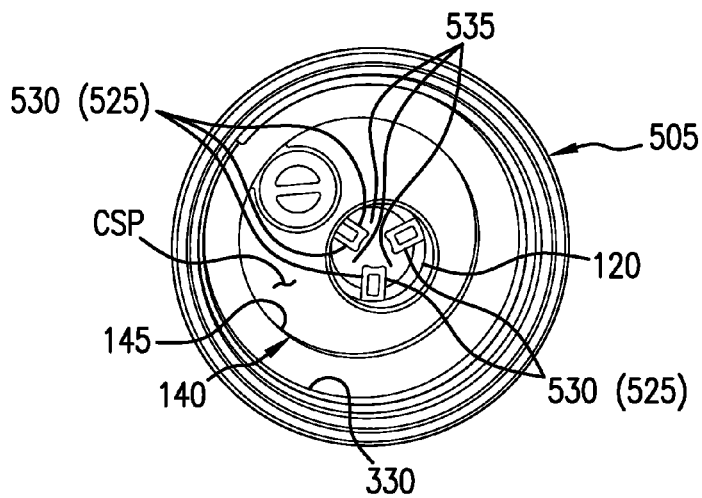

FIG. 66 is an enlarged and rotated section view, taken approximately about section line 66-66 of FIG. 64.

FIGS. 67, 68, 69, and 70 are detail elevation and side views in modified of the embodiments of 61-65 with certain components removed for further illustration.

Figure 70:
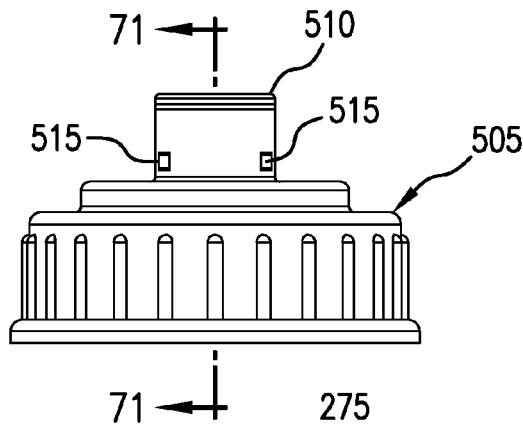
Figure 71:
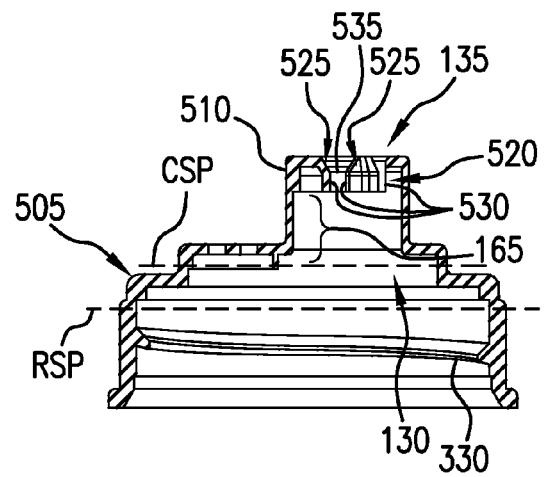
Figure 72:
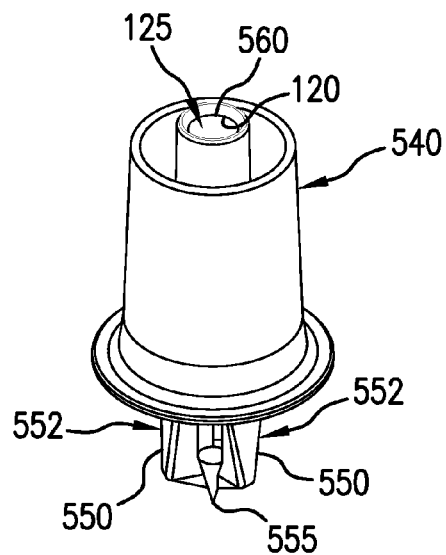
Figure 73:
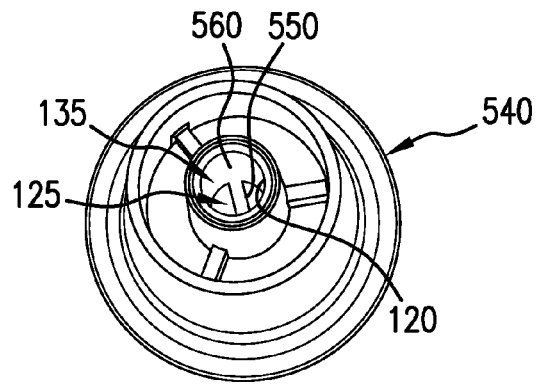
Figure 74:
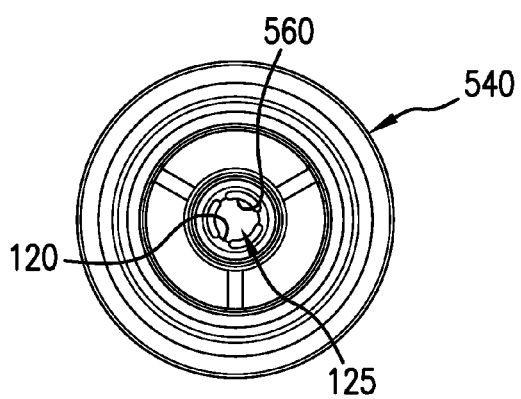
Figure 75:
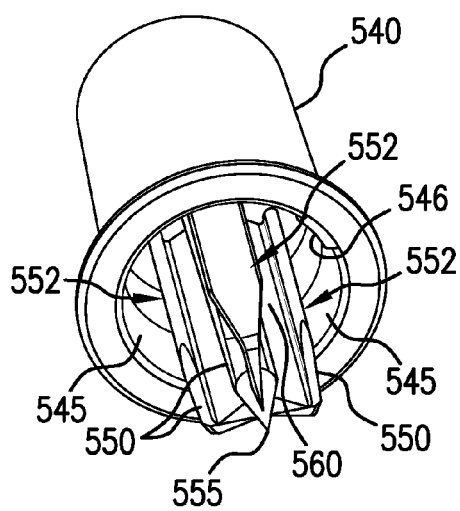
Figure 76:
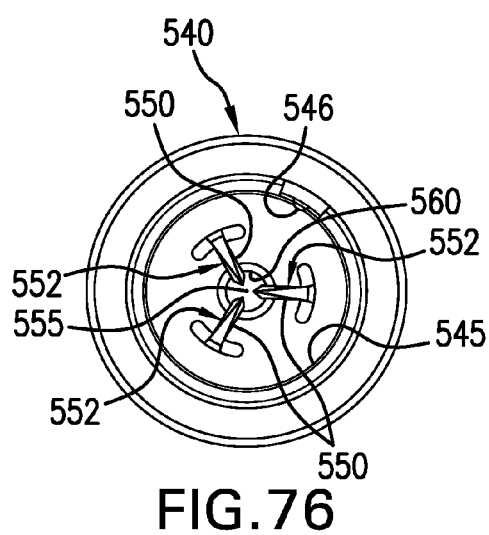
Figure 77:
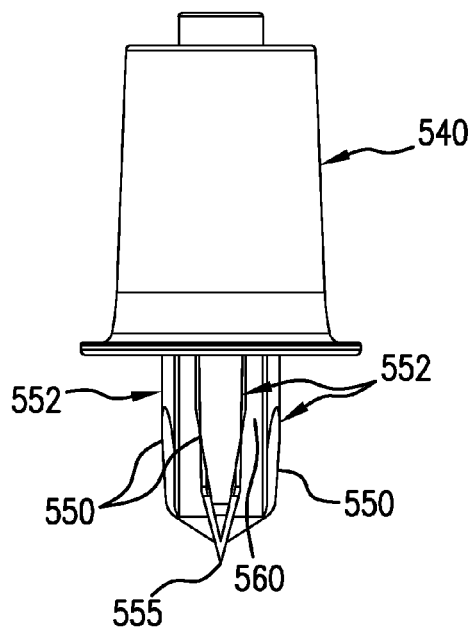

FIG. 71 is an enlarged and rotated section view, taken approximately about section line 71-71 of FIG. 70.

FIGS. 72, 73, 74, 75, 76, 77, and 78 are detail elevation views in modified scale of the embodiments of FIGS. 61-65.

Figure 78:
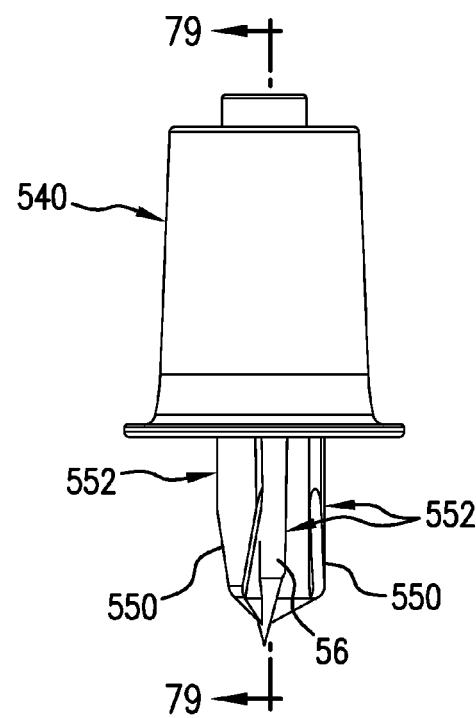
Figure 79:
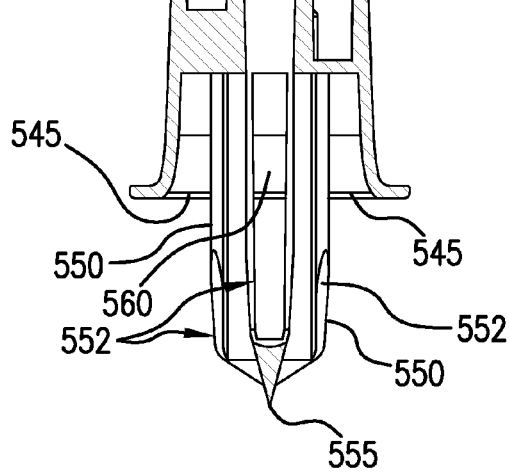
Figure 80:
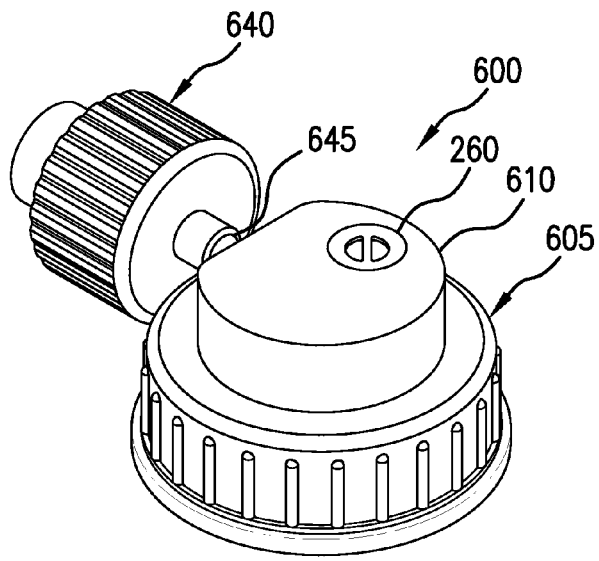

FIG. 79 is an enlarged and rotated section view, taken approximately about section line 79-79 of FIG. 78.

FIGS. 80, 81, 82, 83, and 84 are elevation and side views of another configuration of connector assemblies and systems.

Figure 84:
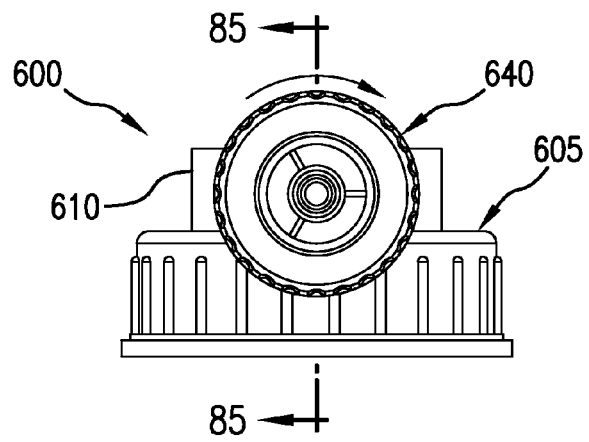
Figure 85:
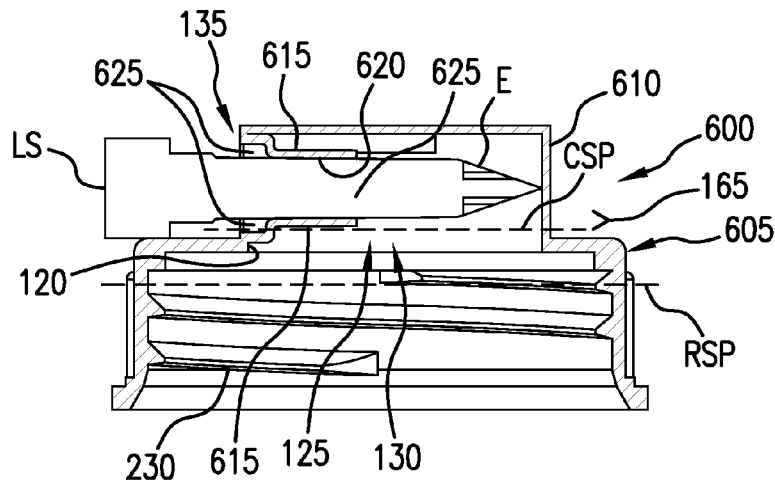
Figure 86:
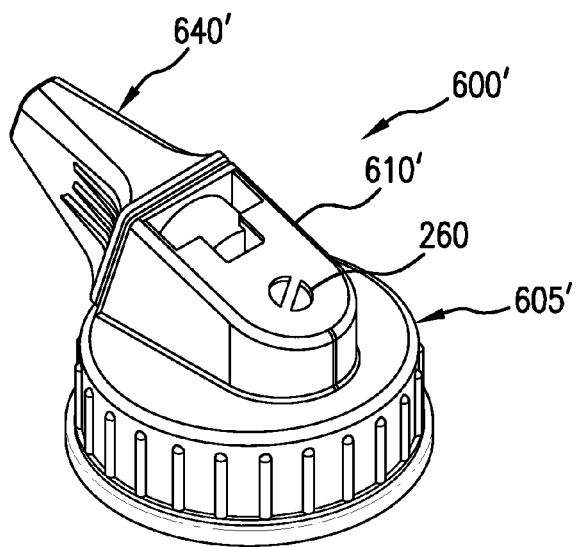
Figure 87:
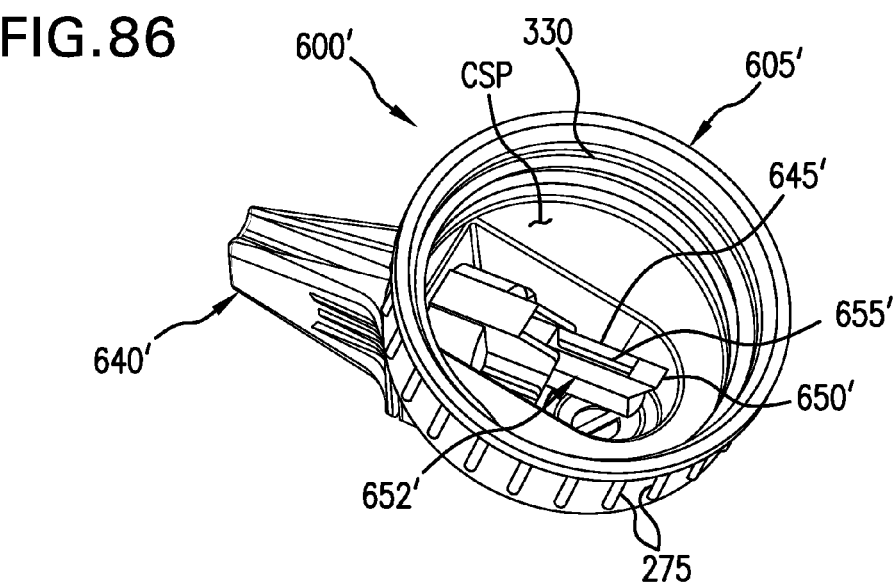
Figure 88:
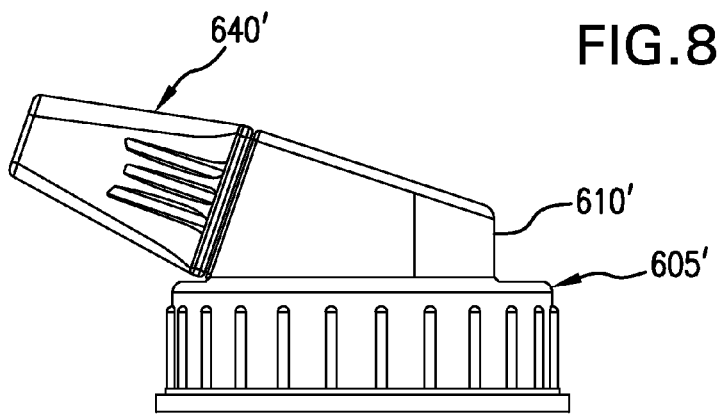
Figure 89:
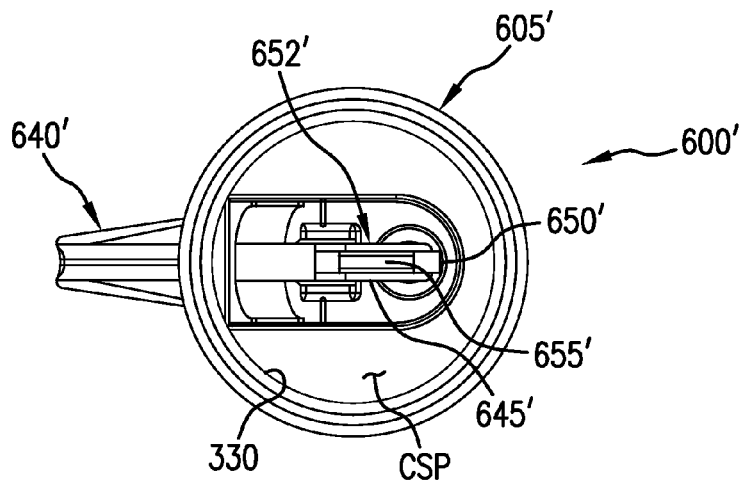

FIG. 85 is an enlarged and rotated section view, taken approximately about section line 85-85 of FIG. 84, with certain structure removed FIGS. 86, 87, 88, 89, and 90 are elevation and side views of another configuration of connector assemblies and systems.

Figure 90:
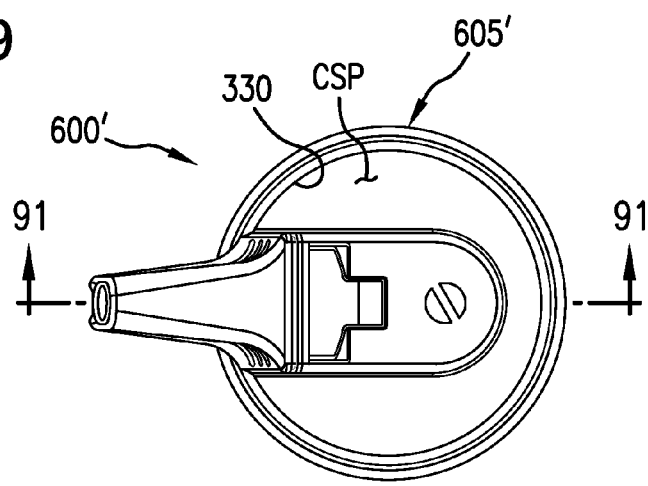
Figure 91:
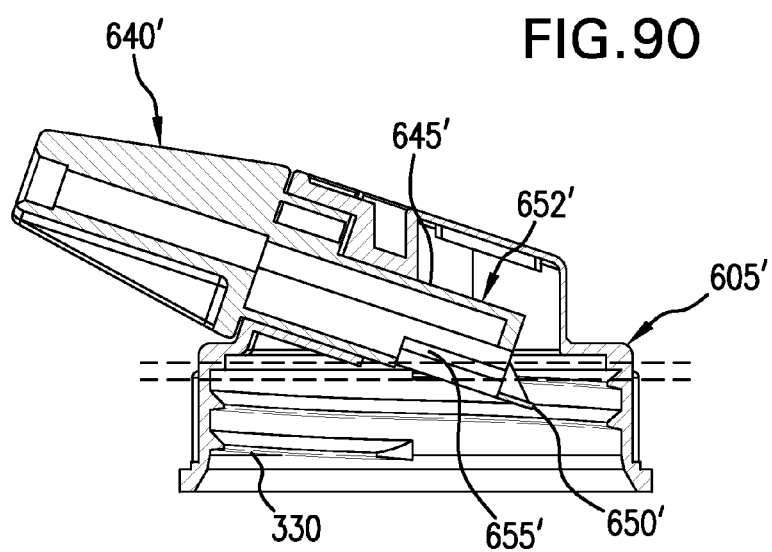

FIG. 91 is an enlarged and rotated section view, taken approximately about section line 91-91 of FIG. 90.

Figure 92:
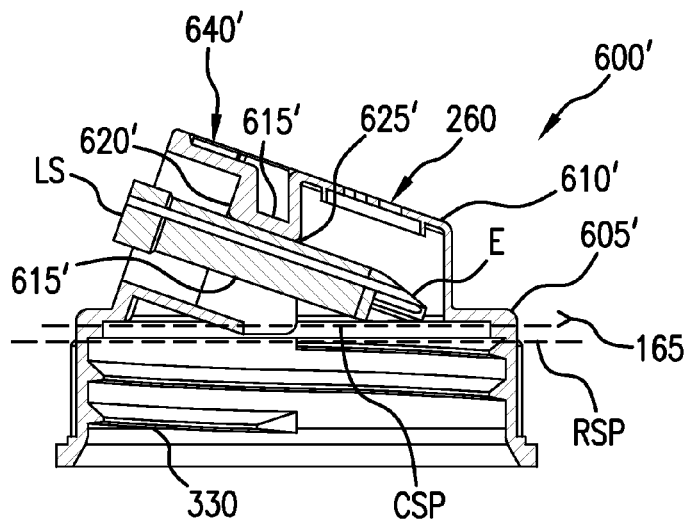

FIG. 92 is a detail section view of FIG. 91, with certain structure removed and an incompatible legacy spike shown for purposes of illustration.

Figure 93:
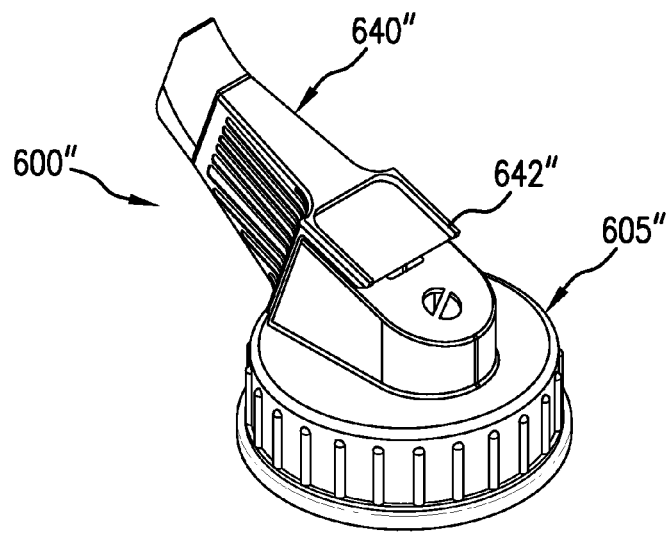
Figure 94:
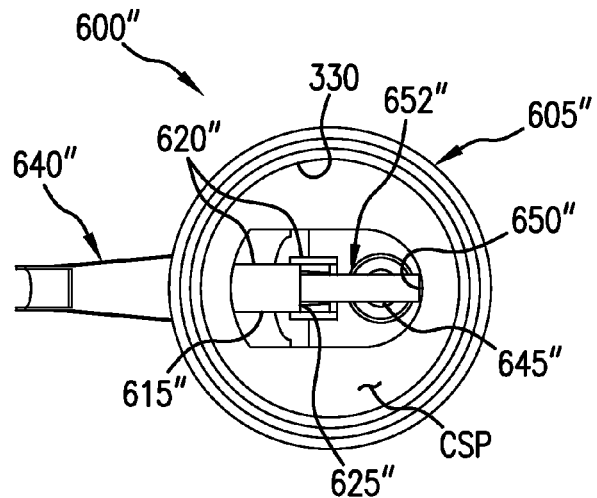
Figure 95:
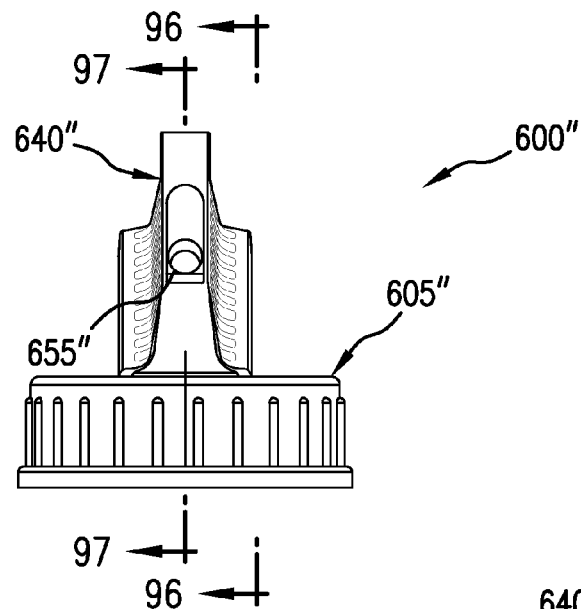

FIGS. 93, 94, and 95 are elevation and side views of an additional variation of connector assemblies and systems.

Figure 96:
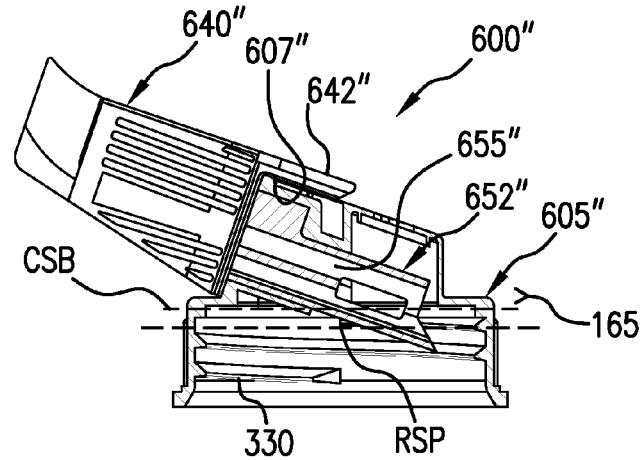

FIG. 96 is an enlarged and rotated section view, taken approximately about section line 96-96 of FIG. 95.

Figure 97:
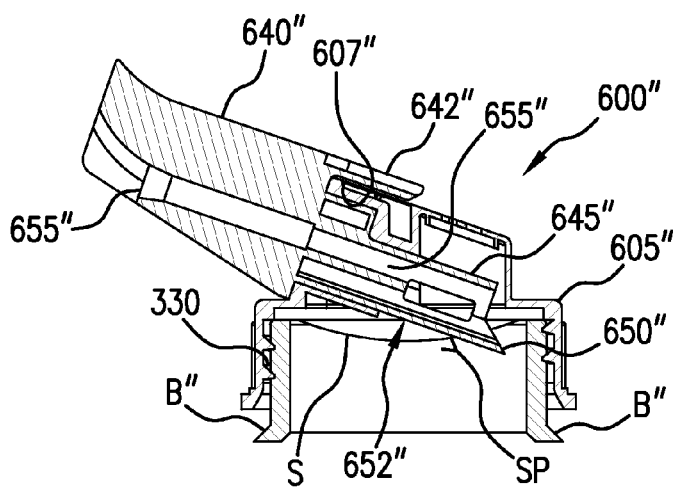

FIG. 97 is an enlarged and rotated section view, taken approximately about section line 97-97 of FIG. 95.

Figure 98:
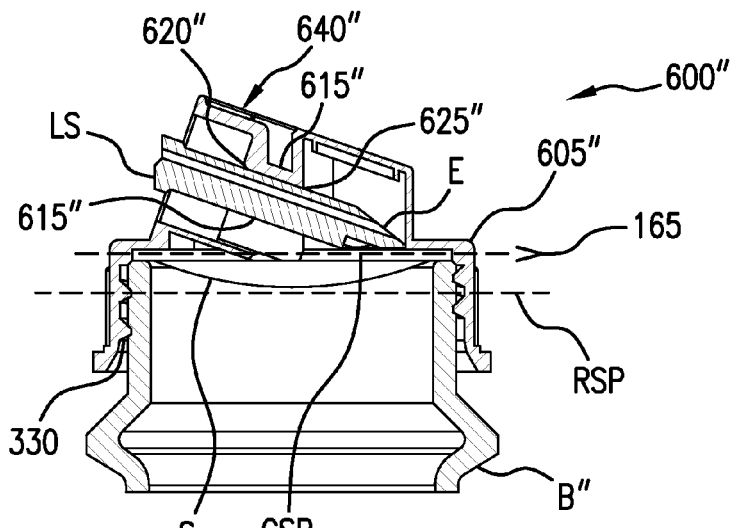
Figure 99:
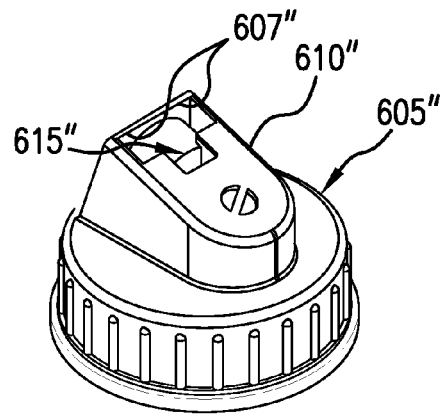
Figure 100:
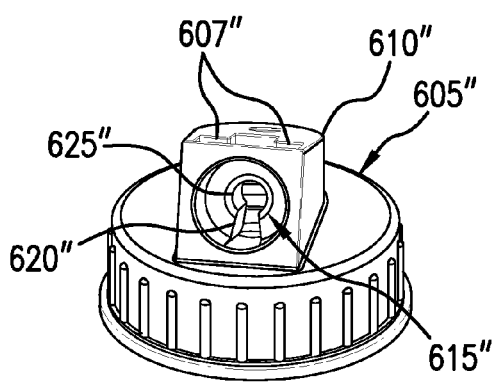
Figure 101:
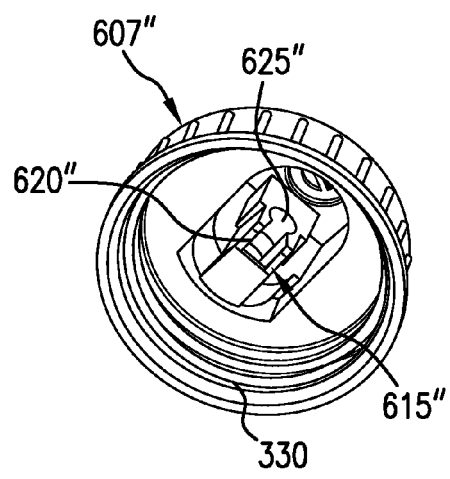
Figure 102:
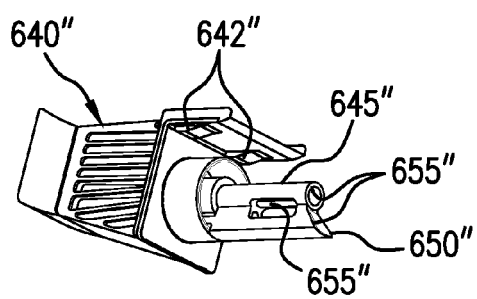
Figure 103:
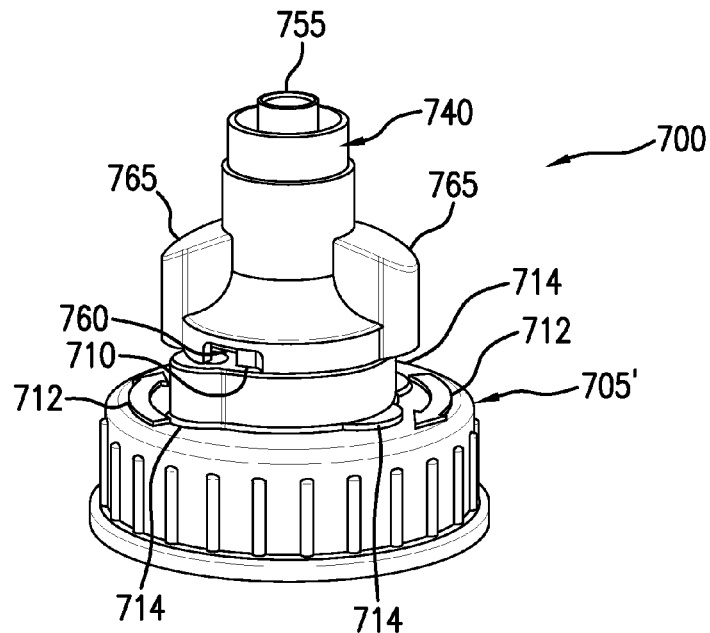
Figure 104:
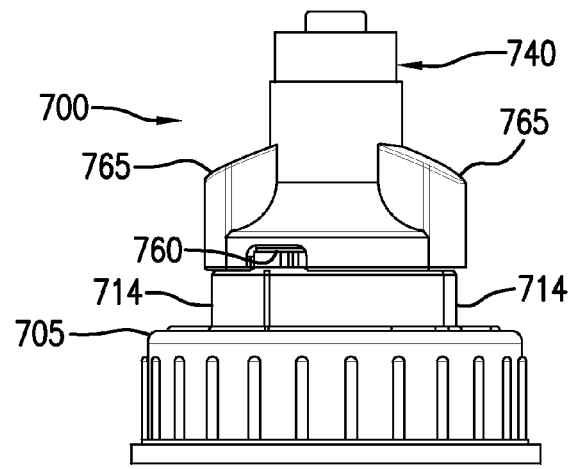
Figure 105:
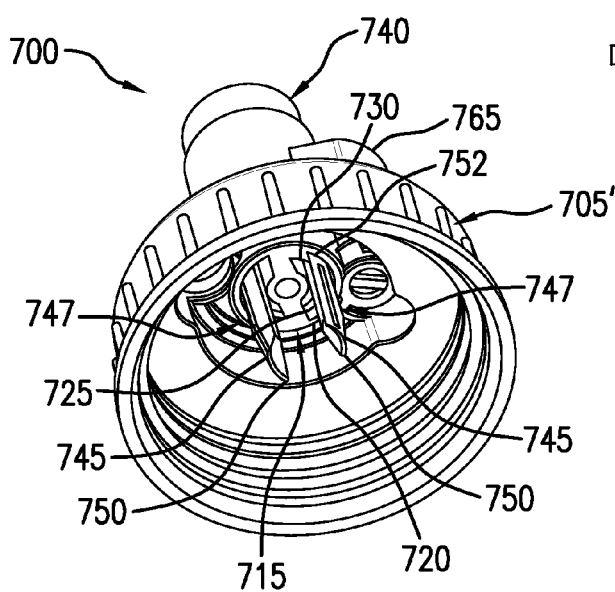

FIG. 98 is a detail section view of FIG. 97, with certain elements removed, and an incompatible legacy spike other components added tom demonstrate added features and capabilities.

FIGS. 99, 100, 101, and 102 are detailed elevation views in modified scales of the embodiments of FIGS. 93-95 with various components removed for further depictions.

FIGS. 103, 104, 105, 106, and 107 are elevation and side views of another version of a connector assembly and system.

Figure 106:
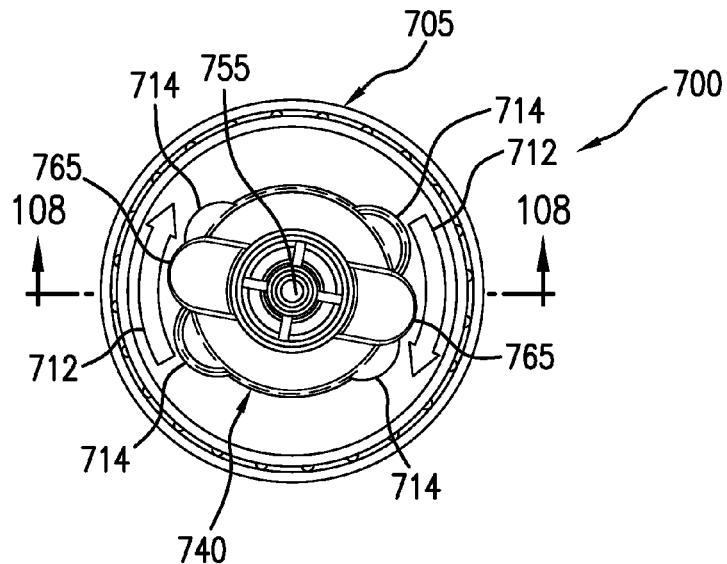
Figure 107:
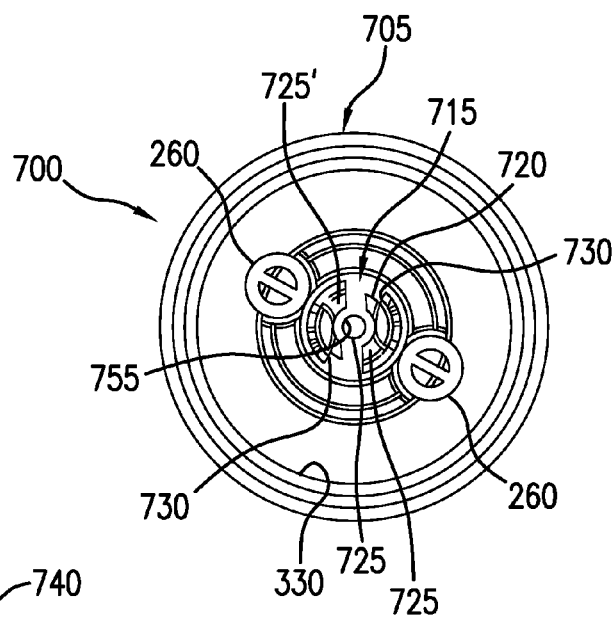
Figure 108:
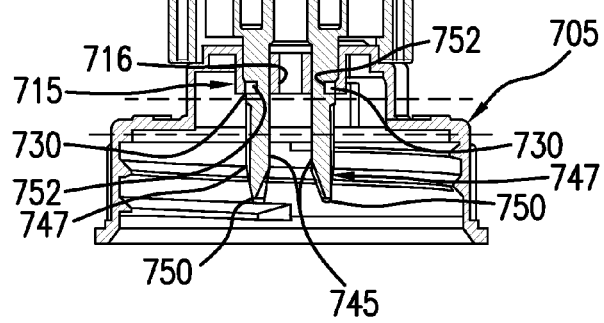

FIG. 108 is an enlarged and rotated section view, taken approximately about section line 108-108 of FIG. 106.

Figure 110:
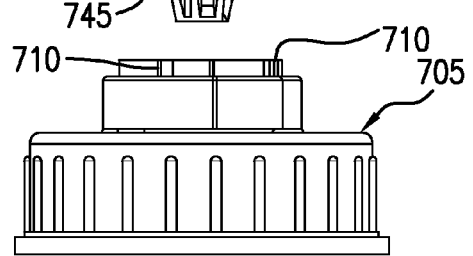
Figure 111:
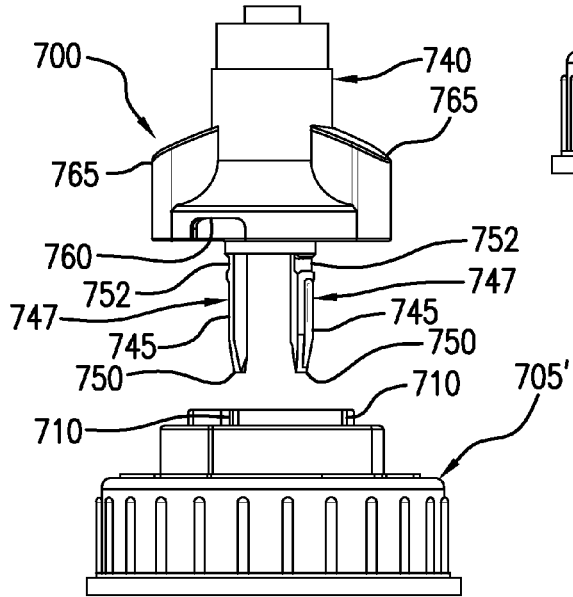

FIGS. 10, 110, and 111 are exploded and rotated in modified scale of the views of the embodiments of 103-107.

Figure 112:
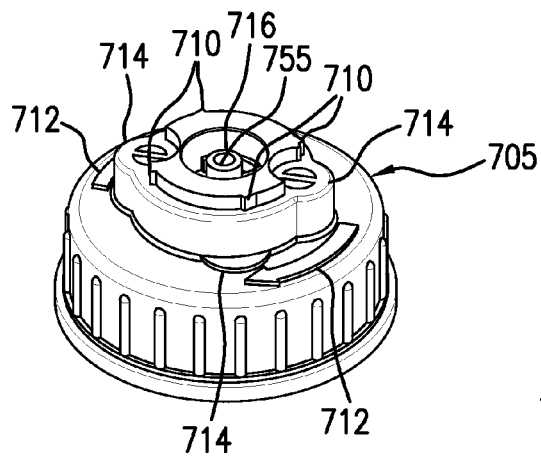
Figure 113:
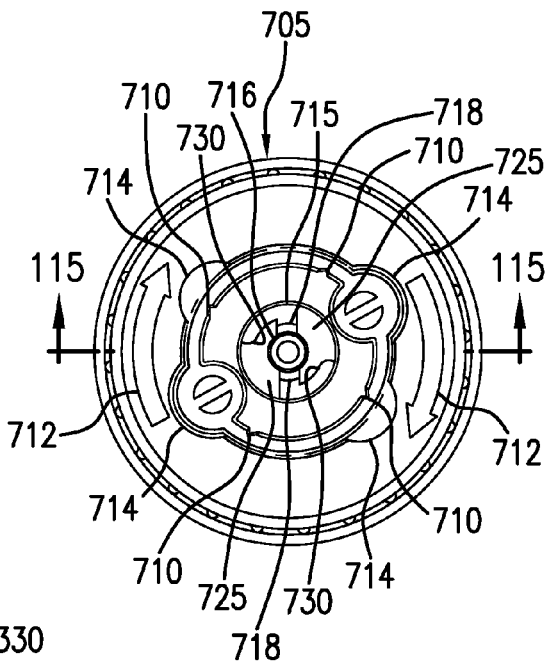
Figure 114:
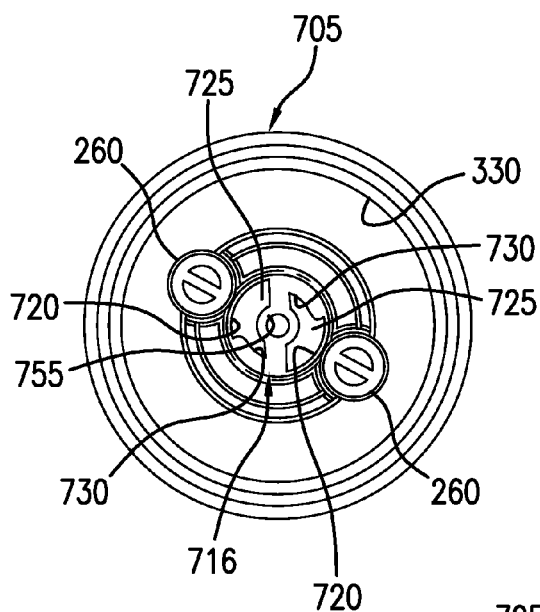

FIGS. 112, 113, and 114 are detail views in modified scale of the embodiments of 103-107.

Figure 115:
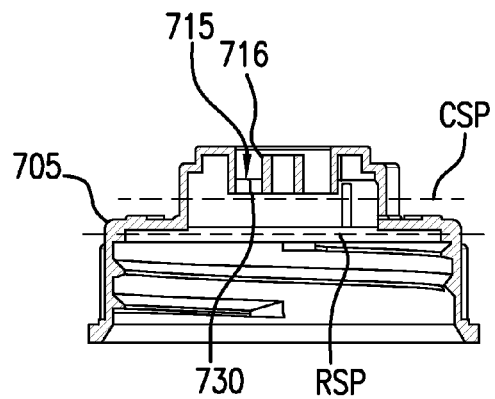

FIG. 115 is an enlarged and rotated section view, taken approximately about section line 115-115 of FIG. 113.

Figure 116:
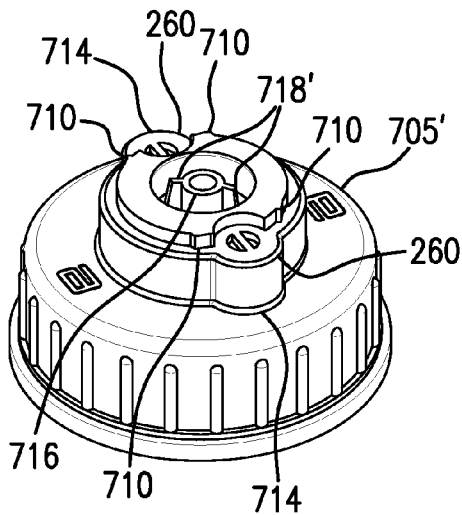
Figure 117:
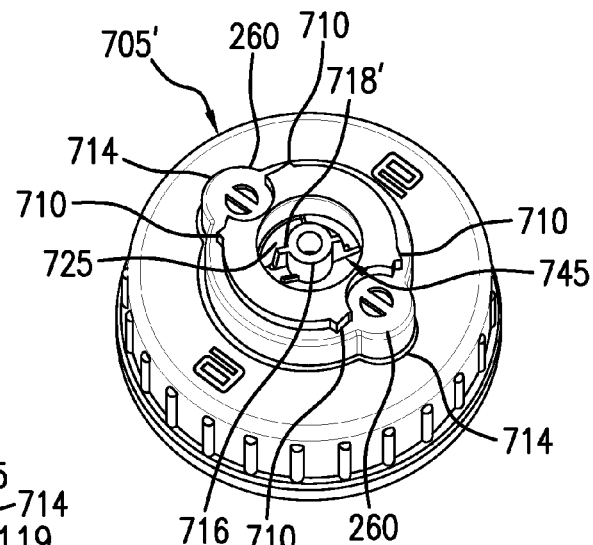
Figure 118:
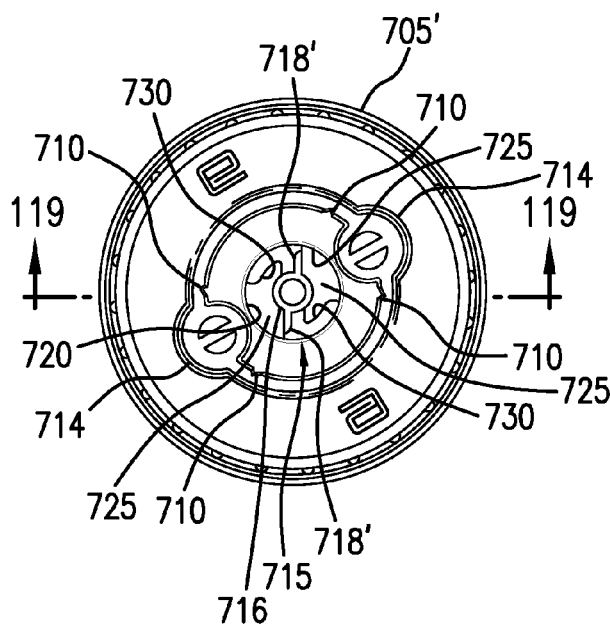

FIGS. 116, 117, and 118 are detail views additionally modified configurations of the embodiments of 103-113.

Figure 119:
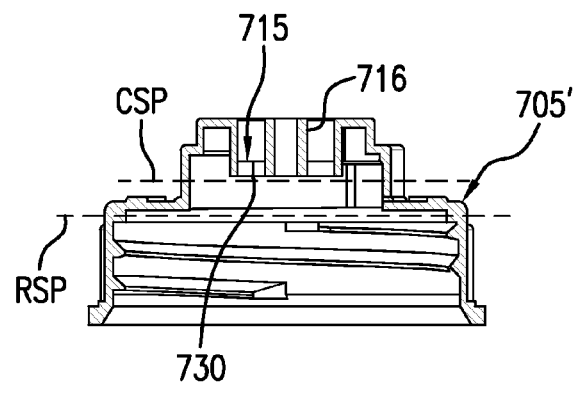
Figure 120:
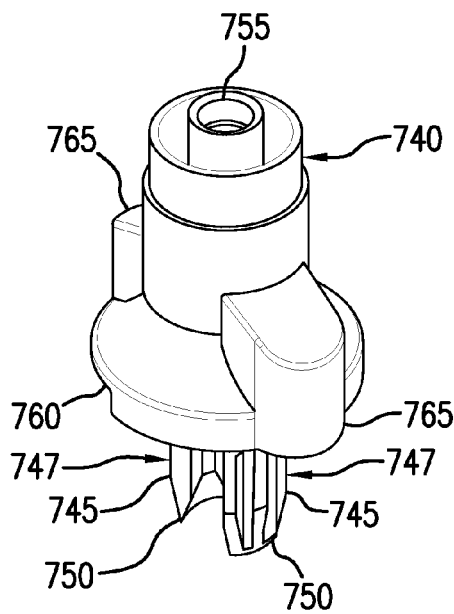
Figure 121:
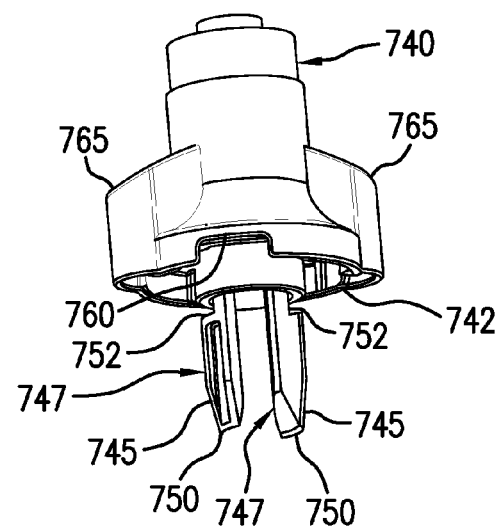
Figure 122:
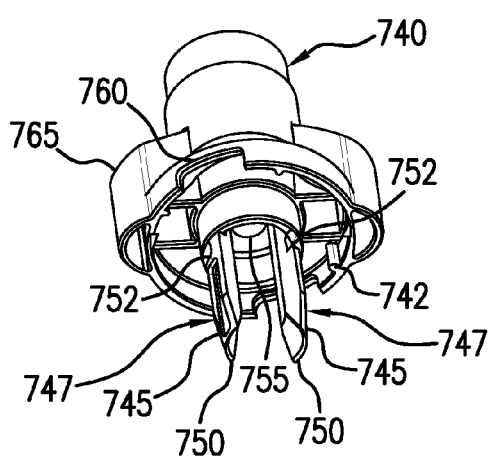
Figure 123:
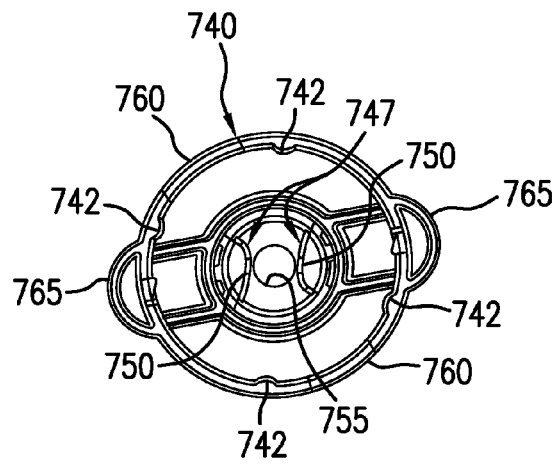
Figure 124:
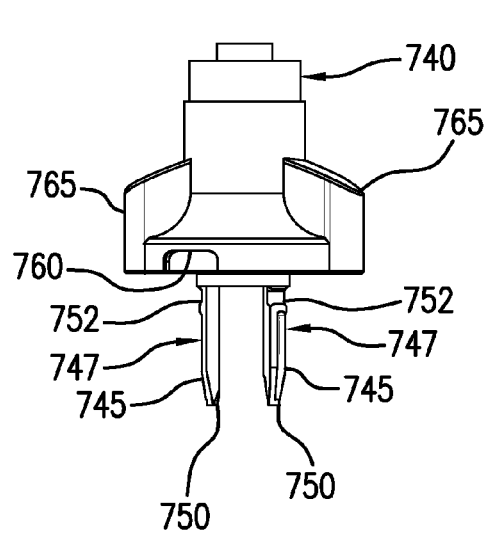
Figure 125:
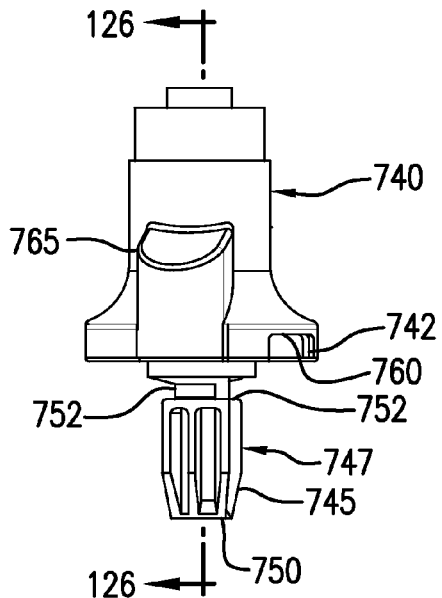

FIG. 119 is an enlarged and rotated section view, taken approximately about section line 119-119 of FIG. 118.

FIGS. 120, 121, 122, 123, 124, and 125 are detail views additionally modified configurations of the embodiments of 104-112.

Figure 126:
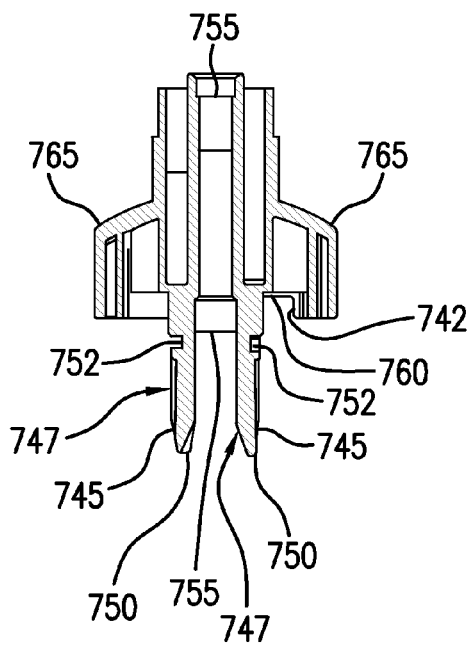

FIG. 126 is an enlarged and rotated section view, taken approximately about section line 126-126 of FIG. 118.

Figure 127:
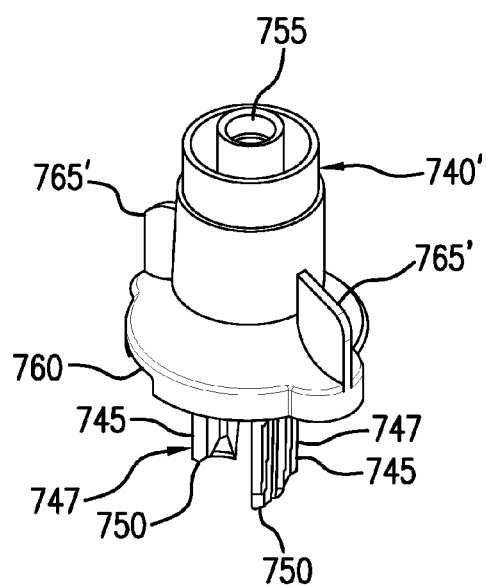

FIG. 127 is an elevation view in varied scale of modified configuration of the embodiments of FIGS. 120-126.

FIGS. 128, 129, 130, AND 131 are elevation and side views of variations of the some of the preceding embodiments that depict added features and capabilities of the connector assemblies and systems of the invention.

Figure 132:
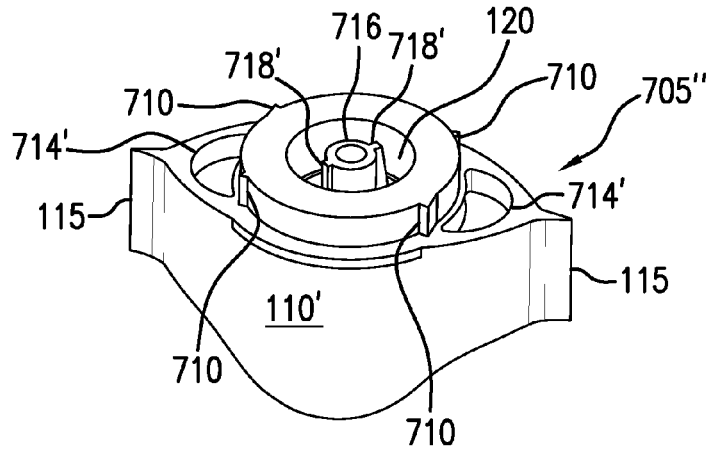
Figure 133:
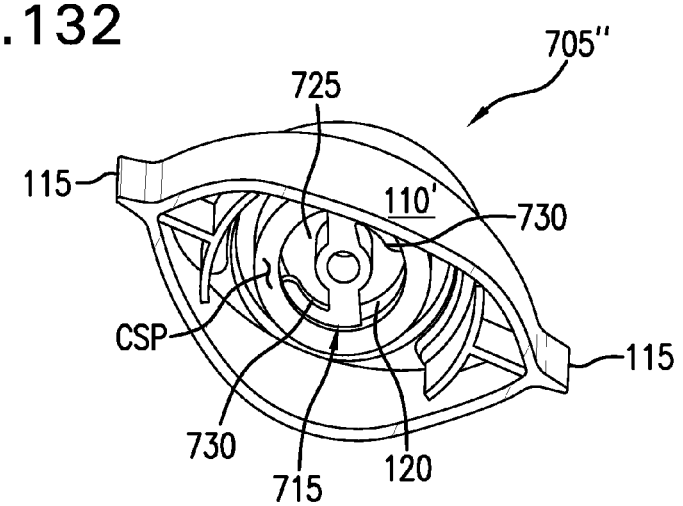
Figure 134:
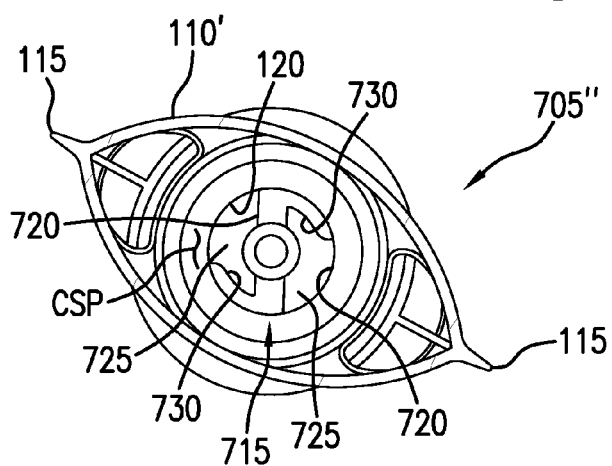

FIGS. 132, 133, and 134 are elevation and side views of additionally modified configurations of the inventive embodiments that illustrate further novel features.

Figure 135:
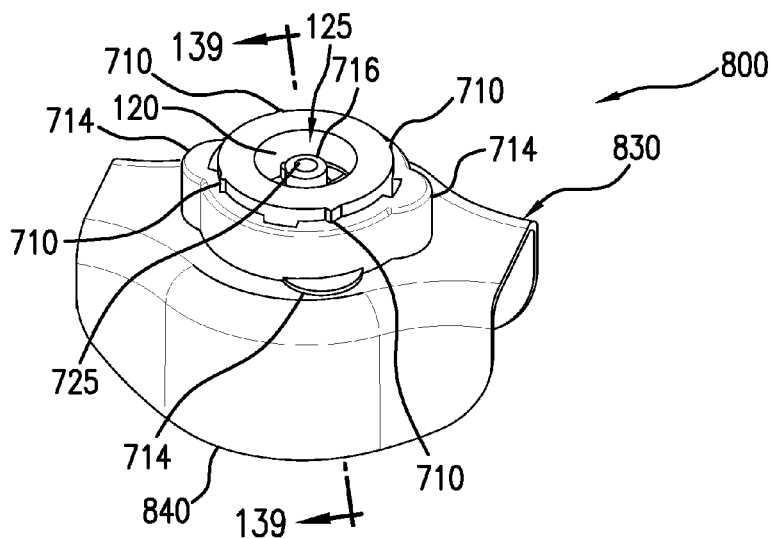
Figure 136:
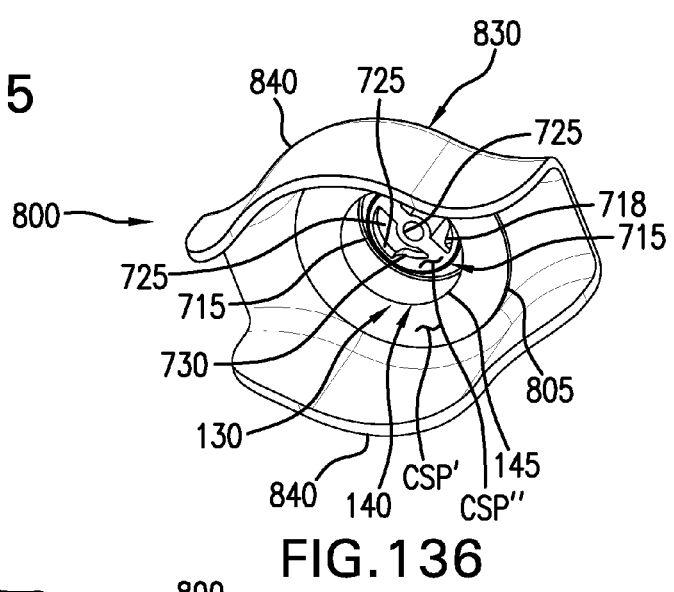
Figure 137:
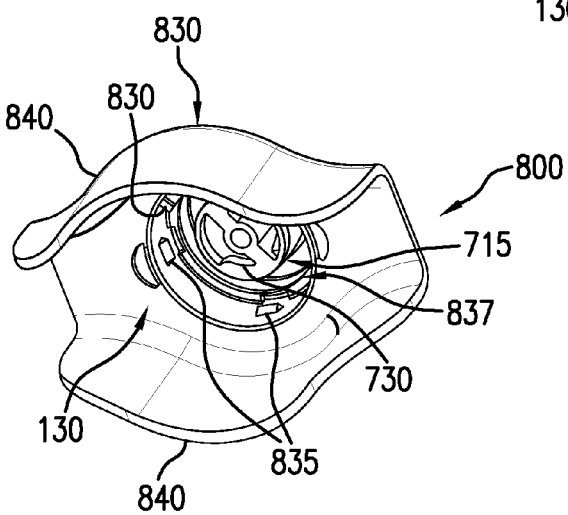

FIGS. 135, 136, and 137 are elevation and side views of other modifications of the arrangements of the preceding connector assemblies and systems.

Figure 138:
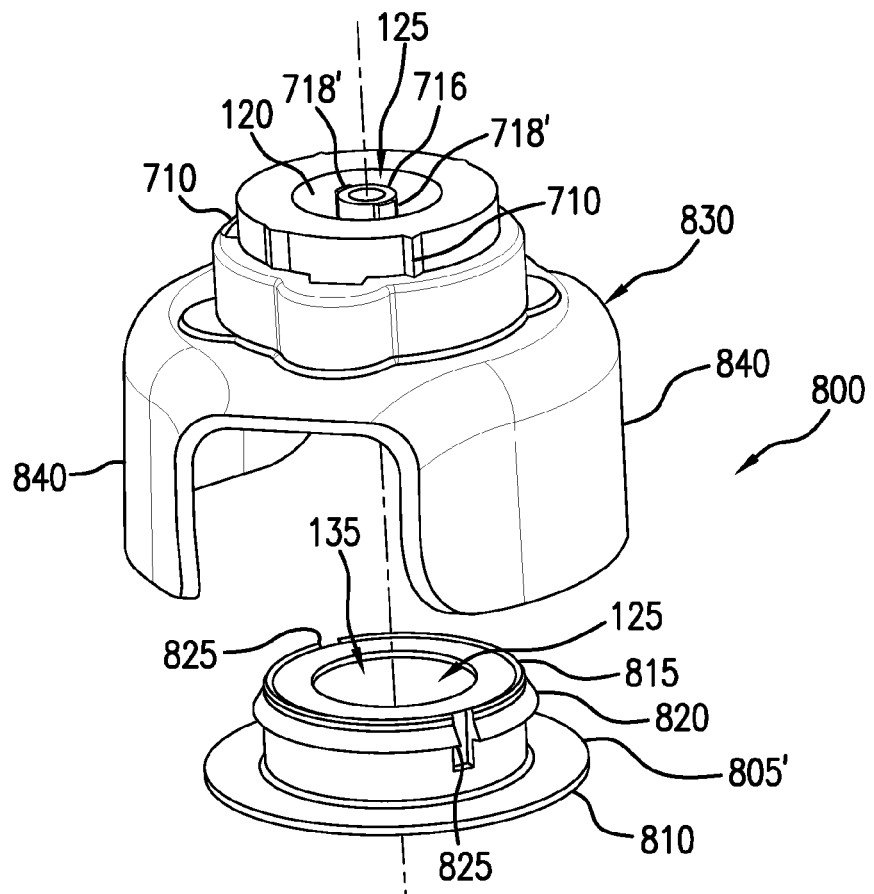

FIG. 138 is an exploded elevation view in modified scale of the connector assembly and system of FIGS. 135-137.

Figure 139:
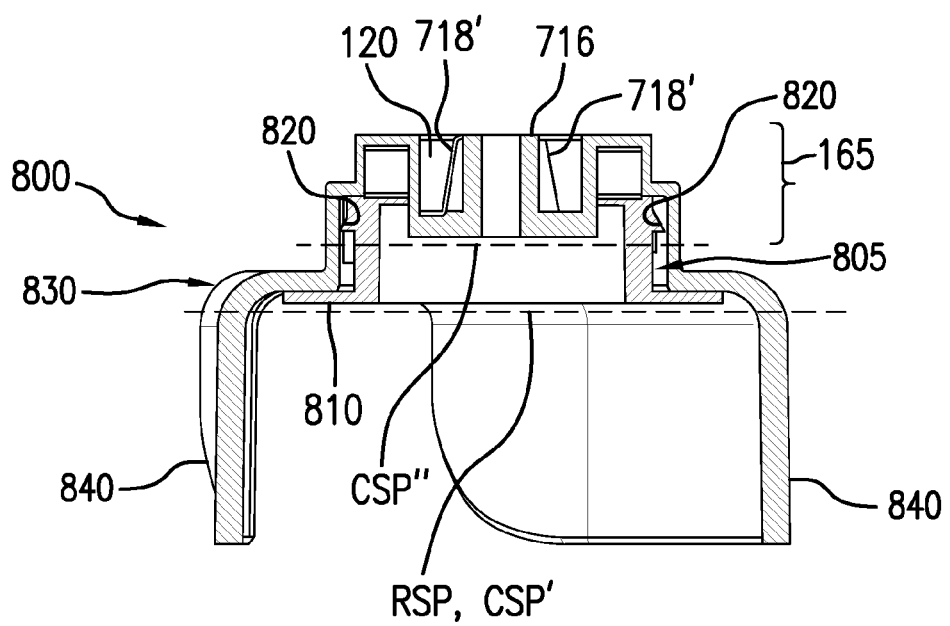

FIG. 139 is an enlarged and rotated section view, taken approximately about section line 139-139 of FIG. 135.

Figure 140:
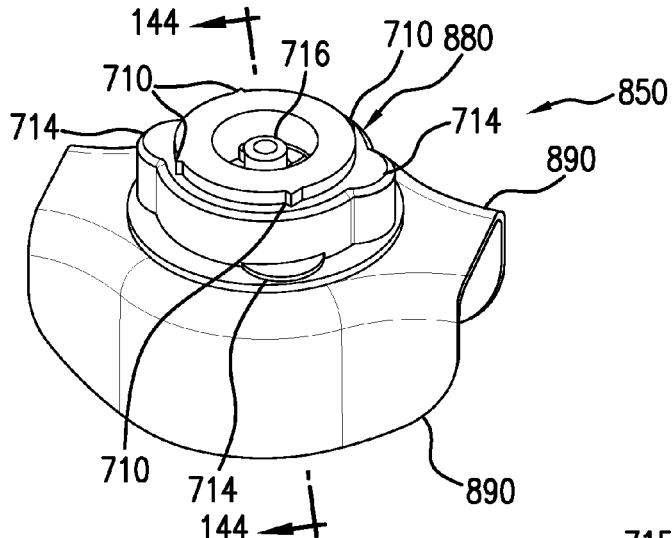
Figure 141:
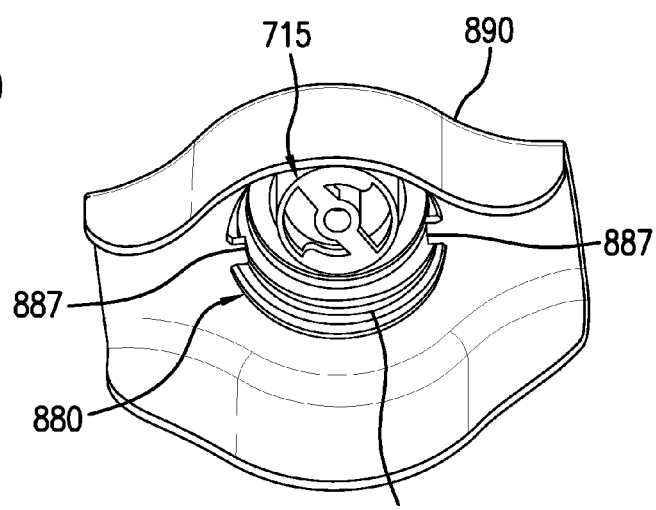
Figure 142:
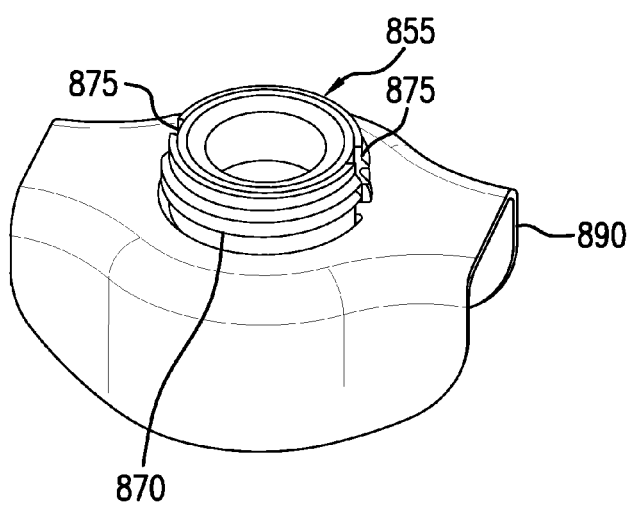

FIGS. 140, 141, and 142 are elevation and side views of further configurations of the many possibly desirable embodiments of connector assemblies and systems already depicted.

Figure 143:
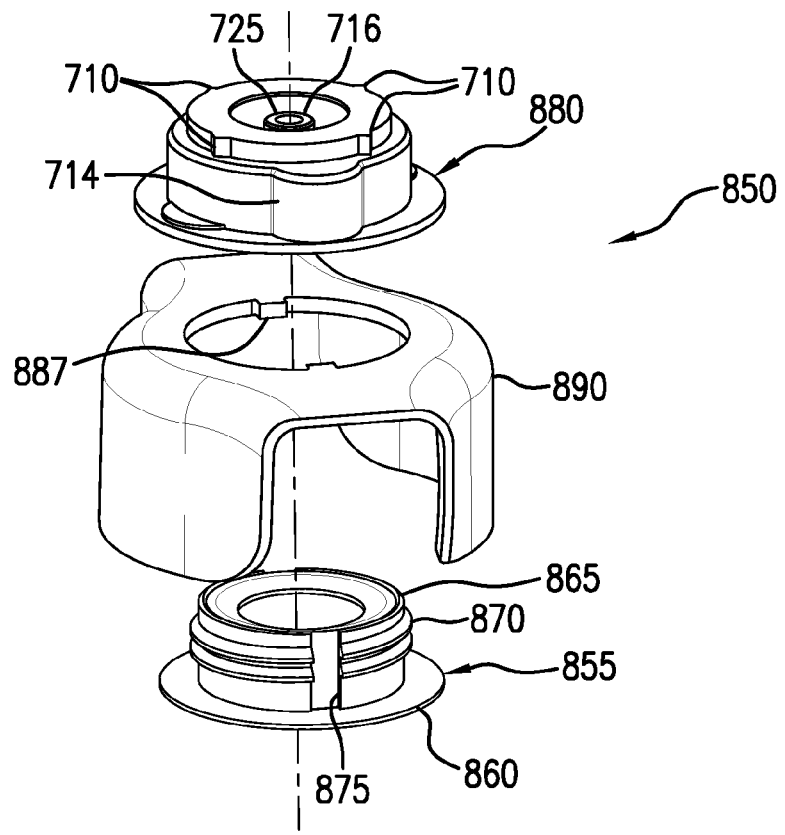

FIG. 143 is an exploded elevation view in modified scale of the connector assembly and system of FIGS. 140-142.

Figure 144:
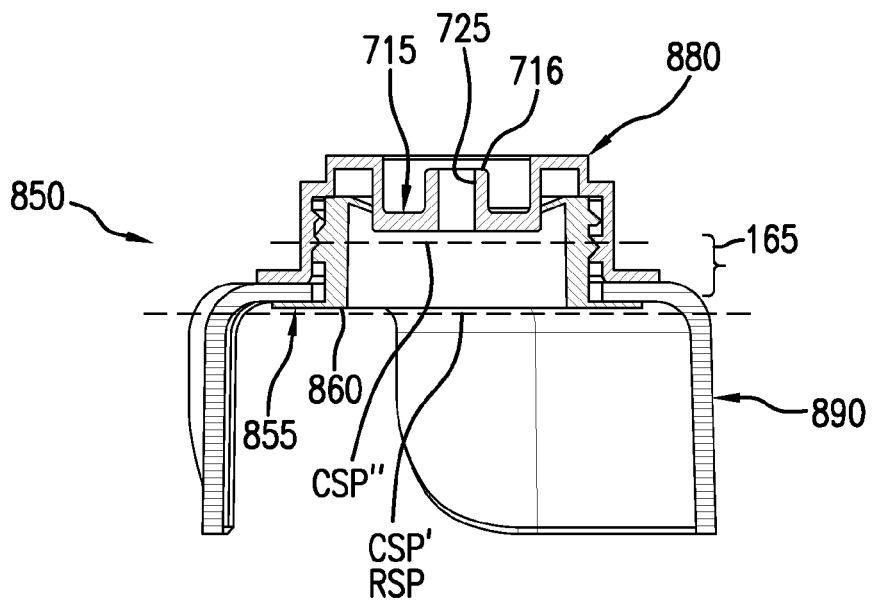
Figure 145:
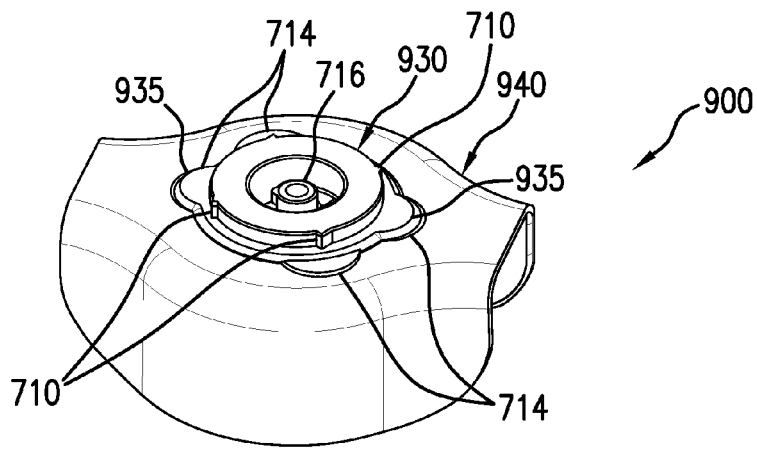
Figure 146:
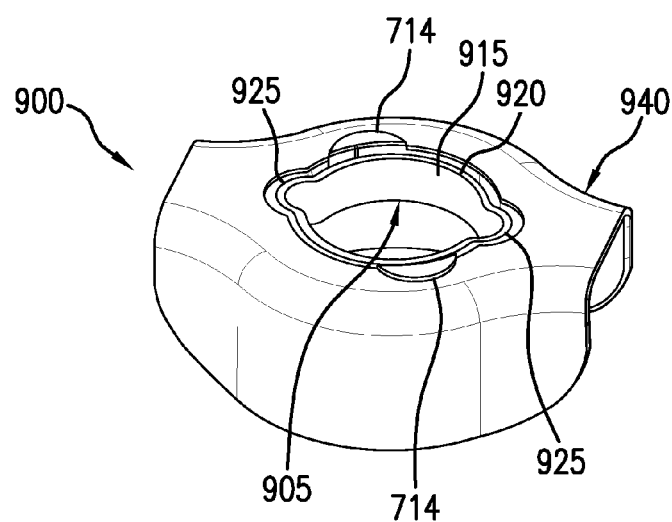
Figure 147:
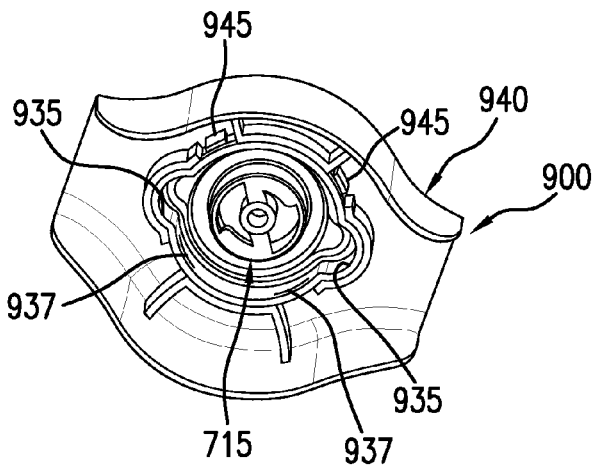
Figure 148:
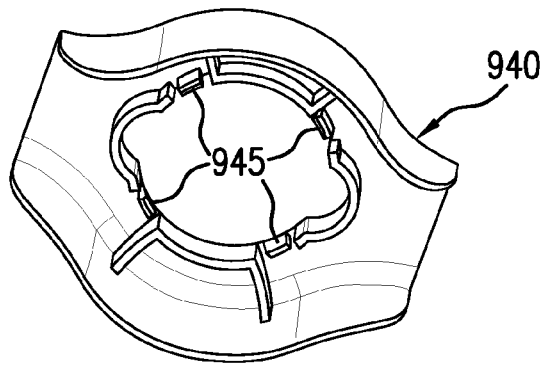

FIG. 144 is an enlarged and rotated section view, taken approximately about section line 144-144 of FIG. 140.

FIGS. 145, 146, 147, and 148 are elevation and side views of another variation of the preceding embodiments of connector assemblies and systems according to the principles of the invention.

Figure 149:
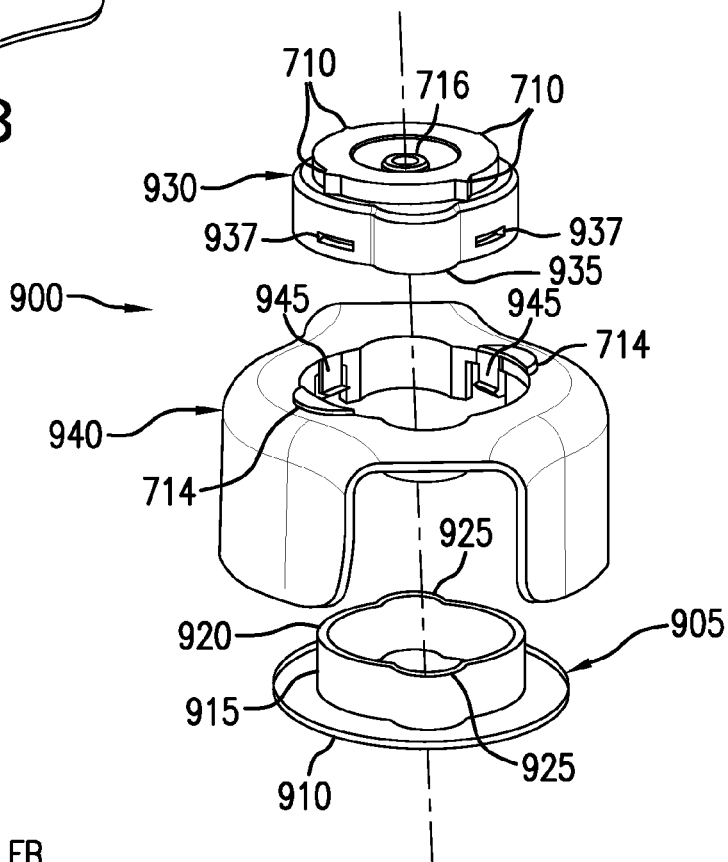

FIG. 149 is an exploded elevation view in modified scale of the connector assembly and system of FIGS. 145-148.

Figure 150:
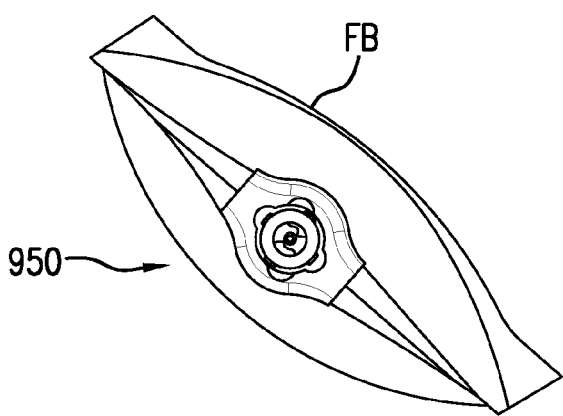

FIG. 150 is an elevation view representative of the connector assemblies and systems of FIGS. 128-148.

DETAILED DESCRIPTION OF THE INVENTION

Figure 3:
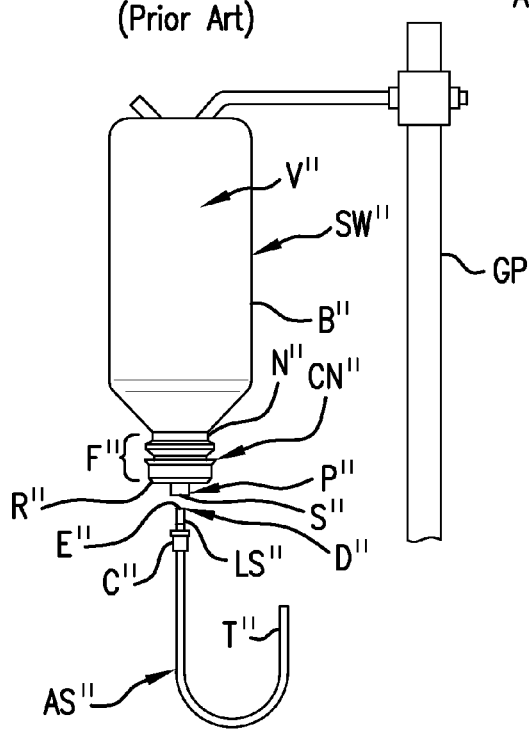
FIG. 3 is an elevation of a prior art, RTH, pre-filled or fillable, open or closed-system, substantially rigid, liquid product bottle, cap, and legacy spike connector fluid tube set assembly hung from a gravity elevation pole.
Figure 7:
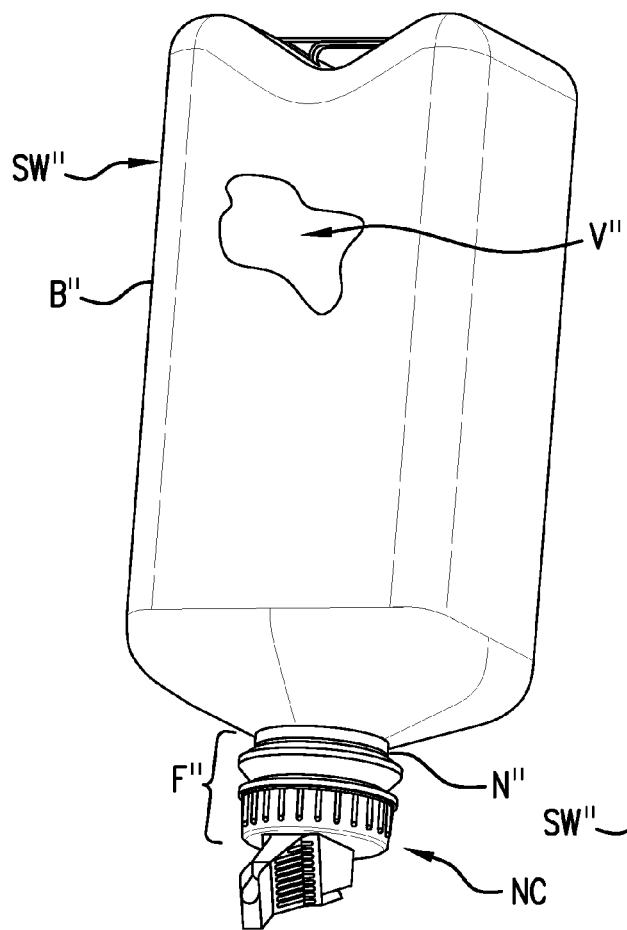
FIG. 7 depicts the RTH rigid bottle of the preceding figures assembled with an embodiment of an inventive enteral connector assembly and system.

In addition to continued reference the preceding illustrations, reference is now also made to FIGS. 7, 8, 9, 10, and 11 wherein the earlier discussed receptacles, containers, and substantially collapsible pouches or bags are depicted as being assembled to the innovative connector assemblies and systems of the invention. More specifically, FIG. 7 illustrates a novel and inventive connector NC assembled to the RTH substantially rigid bottle B' of FIG. 3.

Figure 8:
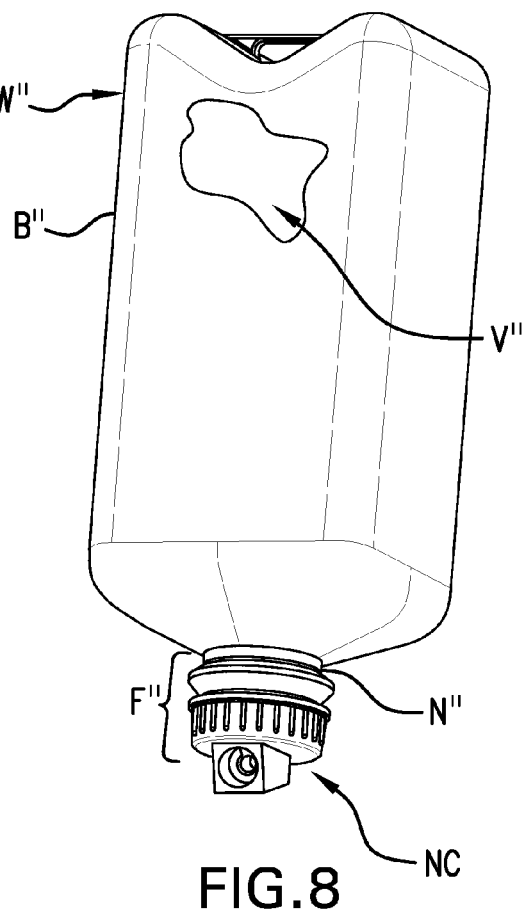
FIG. 8 is another detail view of the bottle and inventive connector assembly and system of FIG. 7 with an element removed for illustration purposes.

FIG. 8 depicts a portion of the connector NC having been removed and disconnected for purposes of further illustration. Similarly, FIGS. 9, 10, and 11 depict another variation of a new connector NC' having been molded in part and/or otherwise assembled to the substantially transparent, collapsible pouch or bag B, replacing the connector C of FIG. 1.

Also now referring to FIGS. 12-23, one of many possibly preferred configurations of the invention are depicted. More specifically, an enteral connection system 100 is configured to communicate fluid between a receptacle such as a fluid pouch and/or substantially collapsible bag, such as any of those pouches bags B, B' of FIGS. 1-2 and 9-11, and as otherwise described and contemplated herein.

Preferably, the enteral connection system 100 includes an end cap or connector 105 that is receivable about a fluid communication port of the bag or pouch. Alternative variations include the end cap or connector 105 contemplate a substantially canoe shaped configuration that is well-suited to assembly to a substantially polymeric collapsible pouch or bag.

In this contemplated arrangement, the bag or pouch can be formed to have a sidewall that is closed about three edges to form an interior volume, and to have an open end with a periphery defining a fluid communication port. The open fluid communication port is preferably received about an exterior surface 110 the end cap or connector 105. Preferably, at least two of the closed edges of the bag are received over cusps 115 of the canoe shaped end cap 105, which enables a high-quality bond to be effected between the bag or pouch and the end cap or connector 105.

Any of the variations of the connector or end cap 105 may also be formed with at least one cap wall 120 that defines an interior lumen or fluid pathway 125 for communicating a fluid between the pouch or bag and an administration or feeding set. The interior lumen 125 and end cap 105 are also preferably defined with a proximal end 130 and an opposite distal end 135. Preferably, the proximal end 130 of the interior lumen is positioned substantially about or adjacent to the fluid communication port of the bag or pouch.

Further preferred configurations include the interior lumen 125 to optionally define a cap seal port 140 defined by a periphery 145 of the end cap wall 120. The periphery 145 may be generally adjacent to the proximal end 130. The periphery 145 of the end cap wall 120 further also preferably defines a cap seal plane CSP, which those skilled in the relevant field of technology may understand is represented by a plane orthogonal to the section view of FIG. 23 and which parallels the line defined in FIG. 23 by periphery 145.

Also optionally preferred, is that the end cap 105 may be positioned to enable the cap seal plane CSP and a receptacle seal plane RSP (FIG. 23) to be substantially parallel. In alternative variations, the cap seal plane CSP and the receptacle seal plane RSP may also be coplanar.

In other modifications to the optional and preferred embodiments contemplated by the invention, an interior face or surface of the cap wall 120 may support and carry at least one spike barrier 150. The spike barrier 150 is preferably substantially proximate to the proximal end of the end cap wall 120 and interior lumen 125. More preferably, the spike barrier 150 substantially spans the interior lumen 125 as may be best understood by those knowledgeable in the field with reference to FIGS. 13, 16, 20, 22, and 23.

The spike barrier 150 more preferably includes an optional barrier periphery 155 that defines and circumscribes at least one barrier port 160 through the barrier 150. Also preferably, the barrier port 160 is in fluid communication with the interior lumen 125 to enable fluid communication through the barrier 150 and the interior volume of the pouch or bag.

The periphery 155 may also establish a barrier geometry that further defines a barrier keyway 162 that is shaped and sized to be incompatible for passage and/or introduction one or more legacy spikes, such as the legacy spike LS shown in FIG. 23. The barrier geometry may have the shape depicted in the various relevant diagrams, or may also have another shape that may accomplish the same result described here, as well as the connector compatibility requirement discussed elsewhere herein.

In these and similar configurations and arrangements, the spike barrier 150 substantially spans the interior lumen or fluid pathway 125 and creates a fence, barricade, and/or barrier to unintended or forcible use of incompatible connectors, which can include for purposes of example but not limitation, the depicted exemplar of a legacy spike LS.

A further possibly desirable capability or feature of the spike barrier 150 is to simultaneously enable fluid communication through the interior lumen or fluid pathway 125 by way of the barrier port 160. Most preferably, such fluid communication through and past the barrier 150 is only possible when used with compatible connector assemblies and systems as contemplated by the invention.

In any of the optionally preferred arrangements of the invention, the spike barrier 150 may establish a barrier interstice 165 (FIG. 23). The interstice 165 is preferably defined and bounded about a circumference by the at least one cap wall 120, and at ends by the spike barrier 150 and the cap seal plane CSP. With reference specifically to FIG. 23 and also to the discussion elsewhere herein, this enables the end cap 105 and the enteral connector system 100 to minimize the success of the unintentional and/or forcible introduction of a distal extent E a legacy spike LS (FIG. 23).

The bounded interstice 165 establishes a legacy distance and a legacy diametrical dimension. The legacy distance LDI (FIG. 23) preferably spans or is parallel to an axis line AL (FIG. 23). Such an axis line AL preferably approximately extends perpendicularly between the cap seal plane CSP and the spike barrier 150.

The legacy diametrical dimension or diameter LDA (FIG. 23) preferably spans a smallest distance across the diameter of the interior lumen 125 between the at least one side wall or side walls 120. More preferably, the legacy diameter LDA. More preferably, the legacy distance LDI and legacy diameter LDA are approximately perpendicular.

In other optionally preferred arrangements, the interstice 165 is bounded by the cap wall 120 to have at least one legacy diameter LDA that is less than diametrical dimension DD (FIG. 23) of at least one legacy spike such as legacy spike LS (FIG. 23). Any of the inventive embodiments may also preferably adapt the interstice 165 to have a legacy distance LDI exceeds a length or extent length EL of the legacy spike LS.

In operation and use, this configuration decreases the likelihood that a user or fluid recipient could successfully introduce a legacy spike LS into the enteral connector systems of the invention and establish fluid communication therewith. Even more preferably, these features may even prevent the distal extents E, E', E" of such legacy spikes LS from extending through any port 160 or keyway 162 of the spike barrier 150, such as barrier port 160. In certain alternative configurations, the keyway 162 may correspond to the port 160.

It is additionally intended that the distal extents E, E', E" will not extend beyond the interstice cap seal plane CSP and/or receptacle or bag seal planes RSP. Even more preferably, acting either alone or in any combination with the preceding elements, it is also preferred that the legacy diameter LDA will also be less than the diameter of a distal extent E, E', E" of such legacy spikes. This preferred modification prevents the distal extents from extending beyond the interstice 165 and reaching the cap seal plane.

These capabilities may be especially desirable in applications where the receptacle, bag, pouch, or other type of fluid container is intended for closed system enteral applications, when it undesirable to pierce or puncture the sealing membrane, seal, and/or septum with components such as the incompatible legacy spikes LS.

In this way, the contemplated legacy distance LDI of the interstice 165, and the legacy diameter LDA of the spike barrier port 160, either alone and/or in combination are substantially more effective than any prior article. This effective combination of features, elements, and capabilities will likely more readily prevent legacy spikes LS and other incompatible connectors from establishing fluid communication with a sealed receptacle, container, bottle, pouch, and/or bag.

In other preferred configurations, the new connector assemblies and systems 100 may further include the end cap 105 to have at least one partial turn groove or thread 170. The groove 170 may be formed about a portion of the cap wall 120 or proximate thereto or in cooperation therewith. Those skilled in the relevant mechanical arts will recognize such partial turn grooves or threads 120 to enable partial turn connections of such end caps and connectors 105 and systems 105 with other components.

With continued reference to the various figures and now also specifically to FIGS. 24-26, those experienced in the fields of art of the invention may comprehend other optionally preferred connector assemblies and systems that cooperate with an interconnect 200. The interconnect 200 may preferably be connected and/or joined to a length of tubing of an administration or feeding set that extends to a fluid recipient.

Figure 109:
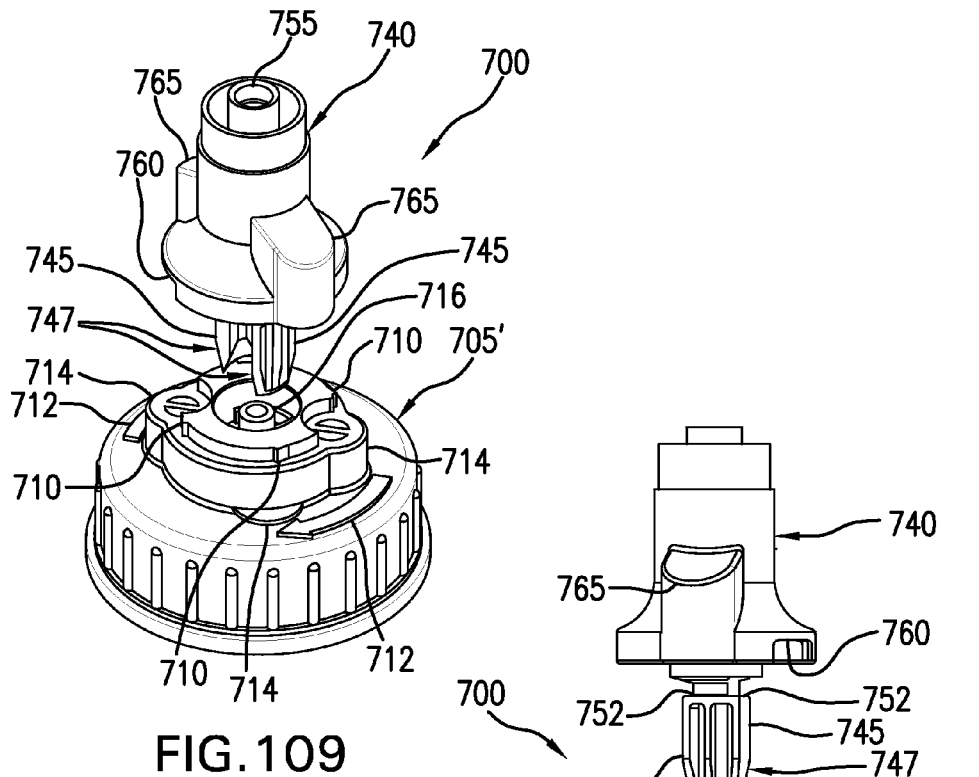

Preferably, the optional interconnect 200 is movable and receivable about the end cap 105 between received positions shown in FIGS. 12-17 and disconnected positions shown in FIGS. 18-26 (see also, for example, FIGS. 109-111). The interconnect 200 also preferably has at least one optional key 205 that is shaped similarly and to be cooperative with the partial turn groove 170. In operation, the key 205 and groove 170 can thereby cooperate, when assembled and connected by a user, to translate the interconnect 200 between the received and disconnected positions relative to the end cap 105.

In other optional configurations of any of the embodiments of the invention, the interconnect 200 may include one or more, and/or a plurality of piercing tines 210 and/or one or more keyed tines 212 that can be carried from the interconnect 210. In further preferred arrangements, the tines 210, 212 extend outwardly from the interconnect 200 towards the spike barrier 150, when the interconnect 200 is proximate to and/or joined to the end cap 105.

Also preferably, the tines 210, 212 may be configured to have a cross-sectional geometry, such as that illustrated in FIGS. 24-26, which is substantially similar to and/or cooperative with the geometry of the keyway 162 of the barrier periphery 155, so as to be receivable through the barrier keyway 162. The piercing tine or tines 210, 212 may also optionally be sized and/or configured to have a tine length that will extend beyond the cap seal plane CSP of the end cap 105 or the receptacle seal plane RSP of the pouch, bag, bottle, or other container.

It may also be optionally preferred for snap-on, snap-fit, and/or snap-in interconnect and end cap arrangements that the at least one and/or plurality of piercing tines 210 include one or more keyed tines 212 in combination with, in addition to, as a replacement, and/or formed as the piercing tines. More preferably, such one or more keyed tines 212 in a cross-section may form and/or define the cross-sectional geometry that is substantially similar to the barrier keyway 162 geometry.

When the interconnect 210 is connected to the end cap or connector 105 during operation, a tip 215 of each tine 210 and/or each of the one or more keyed tines 212 will penetrate and/or pierce any seal, septum, and/or sealing membrane that is sealing the receptacle. During connection and subsequent to such puncturing or piercing fluid communication is established between the interconnect 200, through an interconnect lumen 220, and the interior volume of the receptacle and/or container.

Also preferably and/or optionally, the tip 215 incorporates an angled and/or specially shaped ramp or plow or tearing configuration, which pierces and/or punctures the seal, septum, and/or sealing membrane so as to establish a fluid pathway therethrough that does not seal against the tine 210, and which does not cause particles or pieces of the seal, septum, and/or sealing membrane to separate therefrom. The established fluid pathway may also preferably enable flow of air into a rigid bottle arrangement as fluid is dispensed so as to equalize pressure within the interior volume during dispensement.

Any of the contemplated embodiments of the interconnect 200 may also optionally incorporate any number of ergonomically desirable features, which may include grips and interconnect shapes 225 that are conformal to a typical thumb and forefinger profile to improve grasping, as well as stippling 227 that may improve anti-slip capabilities.

Figures 18, 19, 20:
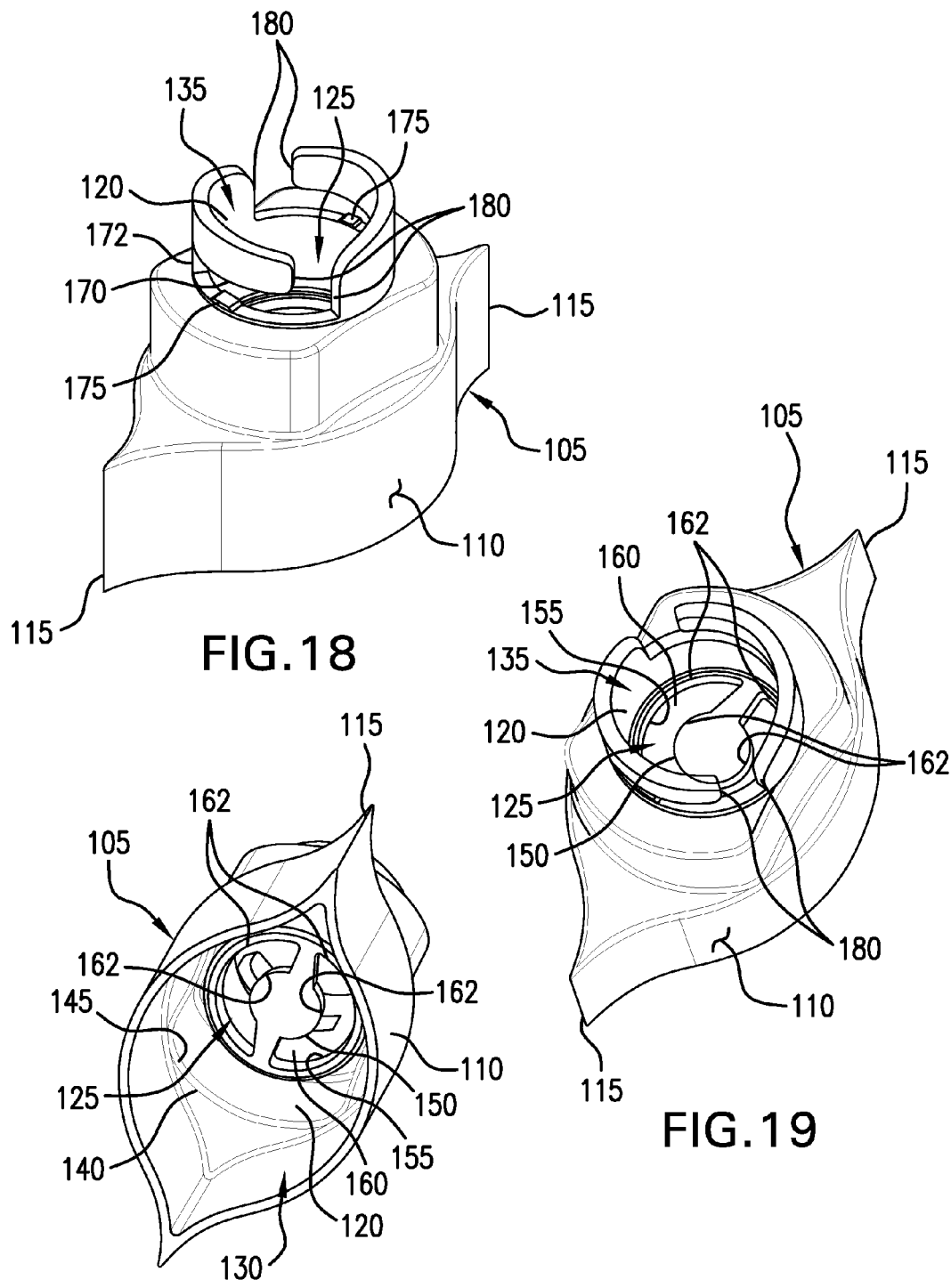
Figure 21:
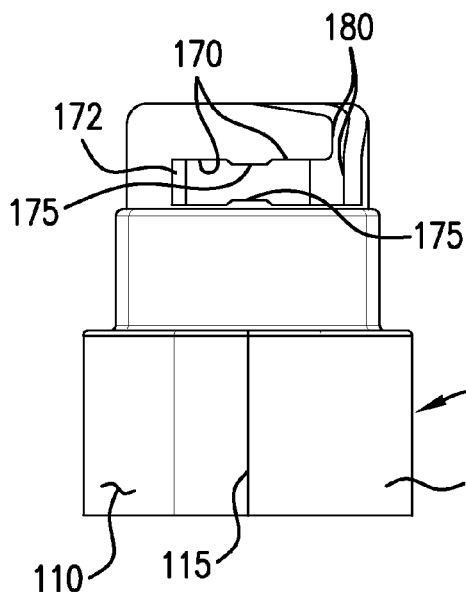

In further optionally preferred variations, the contemplated sealing membranes, seals, and septums may be incorporated onto a portion of the end cap 105. For example, but not for purposes of limitation, such a seal, septum, and/or sealing membrane may be affixed to the cap seal port 140 (FIGS. 13, 16, 20). Such a configuration may be used either alone and/or in combination with the seals and septums contemplated for use in sealing the receptacles, containers, pouches, bags, and rigid bottles.

Any of the arrangements contemplated herein may also be preferably adapted to have the interconnect 200 optionally configured wherein the at least one key or keys 205 are sized and shaped to be operative to obstruct the interconnect from being used with one or more legacy connectors. Also optionally preferred, the at least one partial turn groove 170 of the end cap 105 may be a female helical groove or thread, and the at least one key is a complementary helical male ridge. Even more preferably, the ridge and grooves are sized to have a shape, pitch, diameter, and other dimensions that are incompatible for use with legacy connectors such as IV administration connectors and other legacy enteral connectors that all may be unsuitable for use with the connector assemblies and systems of the invention.

The optionally preferred arrangements of a groove 170 and key 205 optimally sized for interconnection only with compatible components, can be further arranged as depicted to, during operation, translate the enteral cap 105 and interconnect between the received and disconnected positions in less than one turn. In other words, the interconnect 200 and the end cap 105 may be thereby joined as a result of only a partial turn of at least one of the enteral cap 105 and the interconnect 200.

Another possibly preferred adaptation of any of the embodiments, may include the groove 170 to have a groove extent 172 (FIGS. 15, 14, 18) that includes at least one partial turn detent 175 (FIGS. 12, 14, 18). The detent 175 and/or the extent 172, alone or in combination, are preferably sized to receive and capture the at least one cooperative key 205 upon receipt and a partial turn of the enteral cap 105 relative to the interconnect 200. This rotationally operative detent 175, when sized properly relative to the key 205, enable an haptic actuator capability of the connector system 100.

In other possibly desired alternatives, the groove 170 may be further adapted as a partial turn groove 170 that incorporates a substantially longitudinal portion 180. The longitudinal portion 180 receives the key 205 in a telescopic and/or bayonet fashion, where after the key 205 engages the groove 170.

More preferably, the relative sizes of the key 205 and detent 175 are selected to produce audible and/or vibrational tactile feedback to the user when the interconnect 200 is connected and properly received against the end cap 105. Such relative size control can be further optionally modified wherein the detent 175 and extent 172 are positioned, shaped, and sized wherein a disconnection deterrent capability is established wherein both undesired disconnection is physically resisted by detent 175 and key 205, and they also operate as the haptic actuator warning and/or alerting of unintended disconnection.

Depending upon such relative sizing, the disconnect deterrent may prevent disconnection subsequent to the key 205 being captured by the detent 175 and extent 172. In other configurations, the relative sizing arrangement can achieve the aforementioned tactile feedback in the form of an audible and/or vibrational alert that is perceptible by the user.

With reference now also to FIGS. 27-35, another possibly desired series of embodiments are shown, which knowledgeable artisans may comprehend to be an enteral connector assembly and system 250 that is adapted for use with RTH substantially rigid bottles such as bottle B" in FIGS. 3-8. Many of the features, elements, components, and capabilities described elsewhere herein are compatible for use in these proposed arrangements, as can be understood by comparing reference numerals and characters used in this figures that are the same as those identified elsewhere.

For further example, but not for purposes of limitation, the connector assembly and system 250 is adapted to cooperate with the interconnect 200 and its various features. Additionally, a modified end cap 255 is depicted that includes a pressure equalization vent port 260, which operates to equalize pressure within the dispensing bottle during fluid administration as fluid drains from the bottle. Although not shown, the vent port 260 typically also may preferably include a filter media, as can be often appreciated by those skilled in the field of art. Threaded grooves 265 (underside view of FIG. 31), conformal grip indents 270, and anti-slip ribs 275 may also be incorporated for added user convenience.

Another alternatively preferred and modified connector assembly and system 300 is illustrated in FIGS. 36-45, which incorporates many of the elements and features of other embodiments of the invention. In the embodiments, an end cap or connector 305 includes a bayonet mount spike barrier 310 establishes a bayonet distance BD, which that is adapted to substantially exceed the length of the legacy spikes described elsewhere herein.

An interstice 315 is established by the bayonet mount spike barrier 310 and a cap tub 320 that combine to establish the bayonet distance as a legacy distance LDI, which is adapted to substantially exceed the length of at least one legacy spike. The end cap 305 may also include a grip indent 325 to enable a user to rotate the end cap 305 during connection and removal from other components. This arrangement may also include threads 330 to enable connection to a variety of threaded bottles, as well as bags that have threaded connections molded therein, as described elsewhere herein.

This variation of a modified connector assembly and system 300 also contemplates a cooperatively modified interconnect 340 that may also be a keyed tine 342 having a cross-sectional geometry compatible with the bayonet mount spike barrier 310, and which also includes and/or which may be formed as a single, substantially centered tine 345. The keyed tine 342 and/or tine 345 extends to a specially shaped piercing tip 350 adapted to tear open the seal, septum, and/or sealing membrane, and which is formed to have a tine diameter TD. The modified interconnect also preferably includes a fluid communication lumen 355 disposed within the bayonet mount spike barrier 310, which terminates in a barrier port at the proximal end 130 of the lumen 355.

A telescopic receiver 360 is formed within the interconnect 340 proximate to an exterior surface of the keyed tine 342, 345, for cooperative receipt of the bayonet mount spike barrier 310 during connection to the end cap 305. The modified connector assembly and system 300 is preferably adapted to have the tine diameter TD to substantially exceed the diameter of at least one legacy spike such that the keyed tine 342 and/or tine 345 is incompatible for use with legacy IV administration connectors and connector sets.

With continued reference to the immediately preceding figures, and reference now also to FIGS. 46 and 47, another possibly desirable modification to the system 300 is contemplated by the invention. The system 300 is modified to incorporate an alternative end cap 370 that is adapted to use the bayonet mount configuration connected to a polymeric soft pouch or collapsible bag by gluing, heat staking, welding, co-molding, or other suitable means. Such bags or pouches can be any of those illustrated and contemplated in the relevant discussions elsewhere herein.

In yet another group of possibly preferred modifications to any of the embodiments of the invention, FIGS. 48-60 depict varied connector assembly and system 400, which is shown to be adapted for a threaded connector of a bottle of bag type receptacle. As with other alternative variations, use with welded, heat-staked, glued, and other non-threaded connections with bags is also contemplated.

The assembly and system 400 includes an end cap connector 405 that include many elements already described. A snap fitting 410 is included about the cap tub 320, which releasably or fixedly receives an interconnect 440. The end cap 405 incorporates a spike barrier 415 having barrier ports 420 defined by a barrier periphery 425, which also defines a substantially central barrier keyway 430.

The modified interconnect 440 is also depicted, which may be formed as and/or include at least one keyed tine 442 that may be being formed as tine 445 having a substantially serpentine cross-section and an overall exterior cross-section that operates as a key compatible for receipt through the barrier keyway 430. The interconnect 440 may also include a fluid communication lumen 450 extending to a specially shaped piercing tip 455 arranged to plow and/or tear open the seal, septum, and/or sealing membrane. The interconnect may preferably incorporate finger grips 460, and a snap ledge 465 for cooperative receipt in snap fitting 410.

Next referring now also to FIGS. 61-79, another alternatively preferred connector assembly and system is illustrated. A modified end cap 505 is contemplated that includes a bayonet 510 with detents 515 about an exterior surface. Another optionally preferred spike barrier 520 is carried from an interior surface of the end cap wall 120. The spike barrier 520 may further include a plurality of barrier ribs 525 that define a barrier keyway 530 and fluid communication ports 535.

An alternative variation interconnect 540 includes a telescopic receiver 545 having one or more interiorly projecting detent nibs 546 that cooperatively capture the detents 515 to connect the interconnect 540 to the end cap 505 and enable the haptic actuator connection and disconnection capabilities. A plurality tines 550 project from the interconnect 510 and may also be formed as the one or more keyed tines 552 that terminate at a piercing tip 555 that is specially shaped to tear and/or plow open the seal, septum, and/or sealing membrane. Also preferably, the interconnect 540 includes an inner disposed fluid communication lumen 560 between the plurality of tines 550 and/or keyed tines 552.

Any or all of the various optionally preferred configurations of the invention may be further modified as depicted in FIGS. 80-85 to include another type of connector assembly and system 600. The end cap 605 of this arrangement may include a spike cap tub 610 that carries a spike barrier 615 from the interior end cap wall 120 that also defines the interior lumen 125 of other embodiments. The spike barrier 615 may further include a barrier keyway 620 that defines a barrier port 625.

A rotatable interconnect 640 is also contemplated that includes at least one keyed tine and/or tine 645 projecting from the interconnect 640, which carries a rotatable piercing fin 650. Also preferably, the keyed tine 642 may be formed as the combination of the tine 645 and the piercing fin, or in an optionally preferred modification wherein the tine 645 has a cross sectional geometry shaped for compatibility with the barrier keyway 620, with or without the possibly complementary piercing fin 650.

More preferably, the piercing fin 650 is arranged to be receivable by the barrier keyway 620 during connection of the interconnect 640 with the end cap 605. Also preferably, after connection of the interconnect 640 to the end cap 605, the interconnect 640 is rotated about a piercing rotation direction PR.

Figure 81:
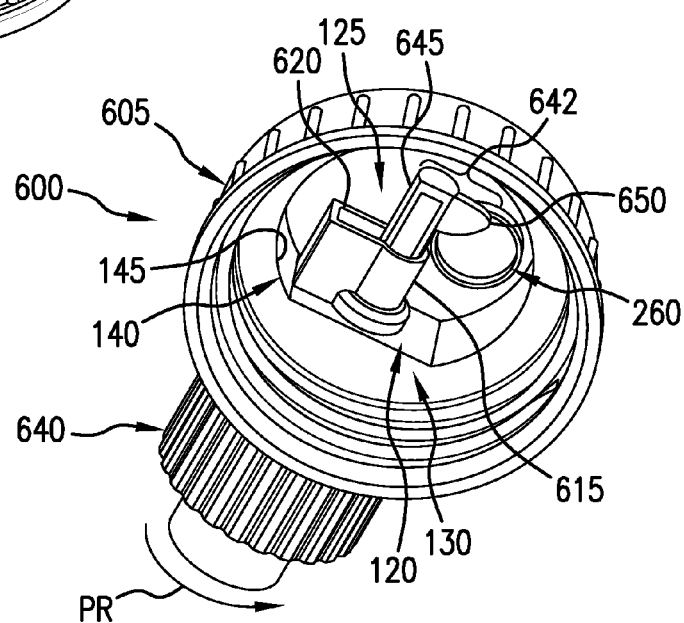
Figure 82:
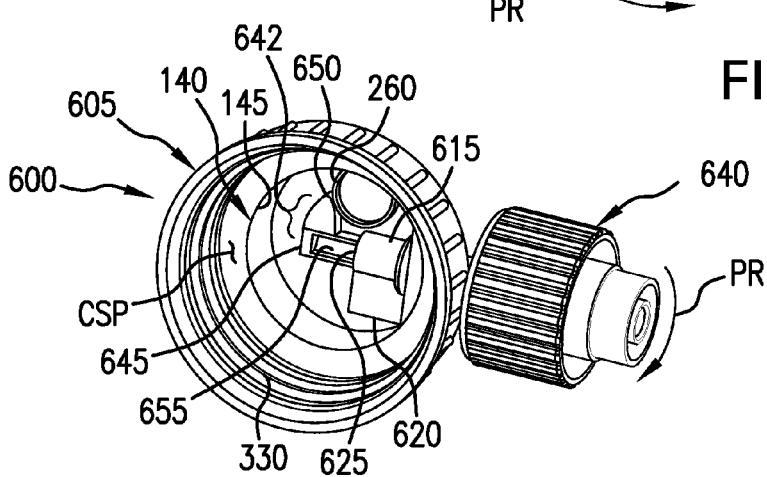
Figure 83:
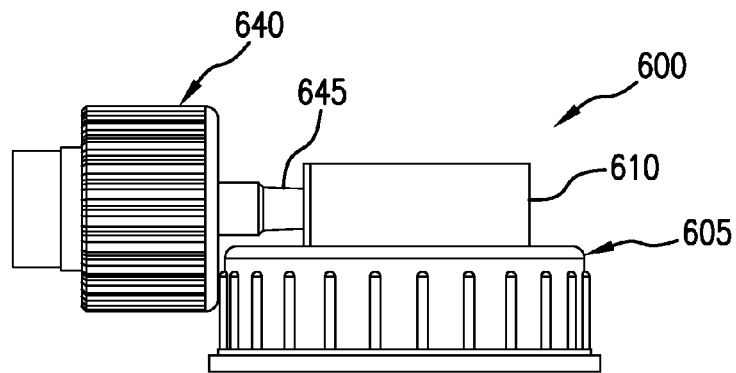

During rotation, the piercing fin preferably passes through and extends into the cap seal plane CSP, until reaching a rest position as shown in FIGS. 81 and 82. In this position, the tine lumen 655 is in fluid communication with the fluid pathway 125 within the end cap 605 and the fluid in a receptacle or container, if a seal or septum was pierced, such as with a closed system container or receptacle.

In another possibly desired modification to the preceding embodiment, or any other embodiments of the invention, a connector assembly and system 600' preferably includes an alternative, angled end cap 605' as can be seen in FIGS. 86-92. The end cap 605' may include any of the other features and elements of the invention, and may have a spike cap tub 610' and a spike barrier 615' that may be carried from the cap wall 120 within the tub 610'. A barrier keyway 620' defines a barrier port 625'.

An interconnect 640' is also preferably included that has at least one interconnect latch 642', and at least one piercing tine 645' with a specially shaped piercing tip 650' and projecting from the interconnect 640'. It may also be preferred that the at least one tine 645' is shaped as a keyed tine 652' to be compatibly receivable with the barrier keyway 620' during connection of the interconnect 640' with the end cap 605'.

In another modification possibly desired for use with any of the embodiments, a connector assembly and system 600", as illustrated in FIGS. 93-102, may incorporate an end cap 605", which may have a spike cap tub 610" having one or more capture detents 607". The detents 607" enabling the haptic actuator connection and disconnection capabilities. The end cap 605" may also include a spike barrier 615", which spike barrier 615" may extend from the cap wall 120 within the tub 610". A barrier keyway 620" may also be incorporated and may define a barrier port 625".

An interconnect 640" may be used with this end cap 605" and may be configured with at least one interconnect latch 642'. At least one piercing tine 645" with a specially shaped piercing tip 650" may depend outwardly from the interconnect 640", and project from the interconnect 640". It may also be preferred that the at least one tine 645" is specifically sized and shaped as a keyed tine 652" to cooperate with the similarly sized and shaped barrier keyway 620". In operation, and upon connection, the piercing tine 645" pierces a seal S to tear and/or plow open and establish a seal puncture SP and fluid communication through the seal S (FIG. 97).

The piercing tip 650", like the many other possibly preferred tips of other embodiments, includes a specially shaped form that punctures or pierces or plows or tears open the seal, septum, and/or sealing membrane to establish a fluid pathway. This is accomplished whereby the tip 650" tears and plows open the seal, septum, and/or sealing membrane without causing pieces or particles to separate therefrom, in a way which also prevents the seal, septum, and/or sealing membrane from sealing against the at least one tine 645".

For arrangements adapted for use with a rigid receptacle or bottle or container, the seal puncture SP is preferably torn open to enable both fluid communication for dispensement from the interior volume and to equalize pressure therein to enable gravity flow dispensement operations.

Referring next to FIGS. 103-127, another optionally preferred connector assembly and system 700 is depicted across the many drawing views. An alternative preferred end cap 705 may include haptic improvements such as visual, audible, tactile and ergonomic aids. For example, the end cap 705 may include one or more partial turn nubs 710, which can be configured as small ramps as may be seen in the various figures. Depending upon the size and shape of the ramps, various amplitudes of audible and tactile/vibrational feedback can be created to alert the user to a correct connection or possible disconnection.

Additionally visual cues can be included in the way of visual connect indicia 712, which can be arrows designated the correct direction for turning components upon assembly to ensure a correct connection. Alternatively, the visual indicia 712 may also be attach and lock alignment symbols or shapes, which can align with cooperative components. Along this line of indicia, attach-lock bumps or bump shapes 714 may be included about a visually perceptible surface of the end cap 700, which may serve to alert users of correct alignments of components during assembly and connection operations.

The end cap also preferably incorporates a spike barrier 715. More preferably, the spike barrier may also include a barrier post 716, which act as an alignment guide during connection of cooperative components. More preferably, the barrier post 716 can be sized to decrease the effective diameter of the fluid pathway to lessen the likelihood that a legacy spike or other incompatible connector can be inadvertently or forcibly introduced into the end cap 705.

To strengthen the barrier post 716 for purposes of increasing the capability to resist introduction of undesirably and incompatible components to the end cap 705, barrier ribs 718 can be formed about the post 716 and the spike barrier 715. As with other optionally preferred embodiments, the spike barrier 715 also may define a barrier keyway 720 that is specially shaped to enable passage of compatibly shaped connector components, while resisting introduction of incompatible components, such as legacy spikes discussed elsewhere herein.

It is also preferred that the barrier keyway 720 incorporate one or more barrier ports 725 to enable fluid communication through the spike barrier 715. It may also be preferred to include one such barrier port 725 through the barrier post 716 as may be understood with reference to the noted figures. For added possible benefit, the spike barrier 715 may be further modified in various alternative arrangements to include barrier latch wings 730.

The barrier latch wings 730 may be adapted to engage with cooperative, compatible components, while also reducing the effective diameter of the barrier ports 725 to lessen the probability that incompatible components, such as the oft mentioned legacy spikes LS, form inappropriate introduction into the connector assembly and system 700.

The end cap 700 is even more preferably adapted for compatibility with an interconnect 740 configured to interact with the noted elements and features of the end cap 700. For example, the interconnect 740 may optionally include partial turn detents 742 cooperative with the partial turn nubs 710 to establish the noted haptic actuator connection and disconnection capabilities and benefits.

Further possibly desired capabilities enabled by the illustrated nubs 710 and detents 742 may also be adapted to enable a partial relative turn between the end cap 705 and the interconnect 740 during assembly. More preferably, the nubs 710 and the detents 742 prevent more than such a partial turn so that the components can be properly and conveniently aligned without damage from over turning.

The interconnect 700 also preferably includes one or more tines 745 with specially shaped piercing tips 750 that plow or tear open the seal, septum, and/or sealing membrane to prevent post-piercing sealing and without separating pieces or particles from the seal, septum, and/or sealing membrane. The tines 745 being preferably and/or optionally adapted to also be keyed tines 747 that have a cross-sectional shape that complements and which is compatible for receipt through the barrier keyways 720. More preferably, the tines 745 and/or keyed tines 747 incorporate proximate a root area of the tines 745, 747, which root area further defines a latch key 752.

The latch key 752 is preferably sized to engage with the barrier latch wings 730 as the interconnect 740 is connected to the end cap 705, and turned relative to the end cap 705. Even more preferably, the latch key 752, the barrier latch wings, and the partial turn nubs 710 and detents 742 are all positioned relative to one another whereby upon a partial turn of the interconnect 740 relative to the end cap 705 simultaneously engages all of the cooperative elements.

It is also preferred that the interconnect 740 includes a fluid communication lumen 755 that can communicate fluid between an interior volume of a receptacle or container and an enteral administration set, that has a tube extending to a fluid recipient. In further optionally desired configurations, the interconnect 740 may also include one or more filter breathers 760. Such filter breathers 760 are preferably incorporated about a portion of the interconnect 740 whereby when the interconnect 740 is properly connected to the end cap 705, the filter breathers rotate into a position proximate to the vent ports 260 that may contain filters.

During operation and use with closed systems having substantially rigid bottles, the filter breathers 760 enable unobstructed air flow with the vent ports 260 and internal filter media so as to equalize pressure with the interior volume as fluid is dispensed there from.

The interconnect 740 may also include one or more turn knobs 765 that may be adapted to cover the vent ports 260 from direct exposure to moisture and contaminants. The turn knobs 765 may while also be adapted to ensure communication of air between the vent ports 260 and the filter breathers 760, which breather may be directly adjacent to the turn knobs 765 as shown in the figures.

With continued reference to the previously discussed figures, and now also to FIGS. 128-131, a modified end cap 705' is shown adapted to employ the features and elements of end cap 705, while also being further modified for use with a polymeric soft pouch or collapsible bag. To this end, the alternatively preferred end cap 705' includes the substantially canoe shaped exterior surface portion 110 and edge cusps or rails 115 from other embodiments. In this configuration, the modified end cap 705' can be heat-staked, welded or glued to such a bag or pouch, and remain compatible for use with the interconnect 740.

For certain applications, it may be optionally preferred to further modify the substantially canoed shaped end cap 705'. With reference now also to FIGS. 132-134, it may be apparent to those having knowledge in the relevant arts that another alternative variation can be achieved in the form of end cap 705". To increase the ability of a user to better grip and manipulate a flexible, polymeric soft pouch or collapsible bag, an exterior surface 110' can be extended further.

In addition to increasing the compatibility for use by certain users who may require increased gripping area such as extended surface 110'. The increased surface area 110' may also increase the surface to which the polymeric bag can be heat-staked and/or welded, thereby increasing the strength of the heat-staked, welded, and/or glued interface between the bag the exterior surface 110'.

Another form of an attach and lock indicia 714' is also represented in the configuration of deep recesses, which can be imprinted with colors or other visually perceptible indicia to assist users in understanding how to align and assembled the end cap 705' to cooperative and compatible components such as interconnect 740.

Attention is now invited to FIGS. 135-139 wherein another alternatively modified connector system and assembly 800 is shown to include an end cap 805. In this possibly preferred adaptation of other embodiments, the end cap 805 is arranged to find utility with polymeric soft pouches and collapsible bags such as those depicted in FIGS. 9, 10, and 11, among others.

Many features and elements have specifically been incorporated here from the connector assembly and system 700, while other new and innovative features and elements have also been devised. In this optionally preferred arrangement, the interconnect 740 is especially compatible for use with the assembly and system 800.

The end cap 805 preferably may be attached to the bag about the cap seat 810 by co-molding, heat-staking, welding, gluing, or other suitable means of attachment. The end cap 805 may further include a rim 815 formed with a snap-on ramp 820 and guide channels 825. A saddle collar 830 includes clips 835 that cooperate to snap onto and engage the snap-on ramp 820 as guide rails 837 slide into guide channels 825 to align the saddle collar 830 to the end cap 805.

The saddle collar 830 is formed with saddle grip walls 840 that depend around and outside a portion of the pouch or bag to improve the ability of users to manipulate the bag or pouch. More preferably, the saddle grip walls are formed from a polymeric material that is more rigid than the polymeric material that may be used to form the soft pouch or bag.

Of the many innovations evidenced by the assembly and system 800, a modified cap seal plane CSP' is depicted. In addition to any seal, sealing membrane, or septum that may be affixed to a fluid communication port on the bag, another seal, sealing membrane, or septum may be also be affixed to the underside of the cap seat 810, which may place the added seal adjacent to any seal on the bag port. It may alternatively preferred to place a seal or septum or sealing membrane about another possibly preferred cap seal plane CSP" (FIGS. 136, 139).

In another preferred and optional modification to any of the inventive configurations, a connector assembly and system 850 is shown in FIGS. 140-145, being adapted for use with the interconnect 740. An end cap 855 includes a cap seat 860 that is connected to a bag similar that shown in FIGS. 9, 10, and 11. A rim 865 of the end cap 855 further may include threads 870 and guide channels 875. A saddle collar 880 includes threads 885 complementary to threads 870. A saddle grip wall 890 includes guide tabs 887 for receipt in the channels 875 to align the saddle grip walls 890 with the end cap 855.

A further modification to the saddle wall embodiments is contemplated in FIGS. 145-149 with connector assembly and system 900, which is also adapted for use with flexible bags as contemplated in the systems 800 and 850. The system and assembly preferably includes an end cap 905 formed from a polymeric material such as a silicone-based material that is suited for and susceptible to co-molding processing.

The end cap 905 is formed with a cap seat 910, and a circumferential wall 915 extending to a rim 920. The circumferential wall 915 preferably further includes diametrically opposed alignment guide bumps 925. A saddle collar 930 is formed with guide bumps 935 and latch detents 937. The detents 937 operative to enable the haptic actuator connection and disconnection capabilities and benefits. A saddle grip wall 940 includes guide recesses 942 and latch clips 945.

During assembly and fabrication, the cap seat 910 is co-molded, welded, heat-staked, and/or glued to the fluid communication port of the flexible bag. Next, the saddle grip wall 940 is aligned and placed about the circumferential wall 915 of the end cap 905. Thereafter, the saddle collar 930 is inserted into the assembly 900 whereby the latch clips 945 of the saddle grip wall 940 are captured in respective latch detents 937 in the saddle collar 930.

With continued reference to FIGS. 9-11, and also to 135-149, and now also to FIG. 150, those having some knowledge and understanding of the relevant arts may be able to comprehend that the connector assembly and system 950 depicted in FIG. 150 renders any of the assemblies and systems 800, 850, and 900 assembled to a soft pouch and/or flexible bag FB.

INDUSTRIAL APPLICABILITY

The embodiments of the present invention are suitable for use in many applications that involve delivery and administration of enteral liquids and fluids to fluid recipients. The many optionally preferable arrangements of the inventive connector assemblies and systems of the invention are readily modified to accommodate nearly any conceivable type of such application. The shape, size, and arrangement of the many illustrated features, elements, capabilities, and components of the novel connector assemblies can be modified according to the principles of the invention as may be required to suit a particular type of enterally administered liquid or fluid, as well as many possible preferred viscosities and densities of such substances.

Such modifications and alternative arrangements may be further preferred and or optionally desired to establish compatibility with the wide variety of possible applications that are susceptible for use with the inventive and improved connectors, assemblies, and systems for delivering enteral fluids, which are described and contemplated throughout the many depicted embodiments. Further modified arrangements are also possible as may be contemplated by those having skill and knowledge in the relevant fields of technology, which prevent or discourage attempts by users to connect legacy IV spikes and IV connectors and other types of undesirable and incompatible components.

Accordingly, even though only few such embodiments, alternatives, variations, and modifications of the present invention are described and illustrated, it is to be understood that the practice of such additional modifications, combinations, and variations and the equivalents thereof, are within the spirit and scope of the invention as defined in the following claims.

The invention claimed is:

1. An enteral connection system adapted to communicate fluid between a receptacle and an enteral feeding set, the receptacle including at least one side wall defining an interior volume and having a finish that forms a fluid communication port defining a receptacle seal plane, the system comprising:
    an end cap receivable about the fluid communication port and formed with at least one cap wall defining an interior lumen for communicating the fluid between the receptacle and the feeding set;
    the cap wall having an interior face carrying at least one spike barrier radially spanning the interior lumen to establish an interstice therein between the barrier and the receptacle seal plane when the end cap is received about the receptacle;
    at least one barrier port formed in the spike barrier and in fluid communication with the interior lumen;
    a periphery circumscribing the at least one barrier port and having a barrier geometry that establishes a barrier keyway; and
    wherein the interstice and at least one spike barrier establish a distance exceeding a length of at least one incompatible spike to prevent the at least one incompatible spike from extending to the seal plane.

2. The enteral connection system according to claim 1, further comprising:
    the end cap including at least one partial turn groove formed about a portion of the cap wall; and
    an interconnect having at least one key cooperative with the partial turn groove to translate the interconnect between received and disconnected positions relative to the end cap.

3. The enteral connection system according to claim 2, further comprising:
    at least one piercing tine carried from the interconnect and configured with a cross-sectional geometry substantially similar to the barrier geometry to be receivable through the barrier keyway;
    wherein the at least one piercing tine extends beyond the seal plane to enable fluid communication between the interior volume and the enteral feeding set; and
    wherein the at least one key obstructs receipt of the interconnect in at least one incompatible connector.

4. The enteral connection system according to claim 2, further comprising:
    the at least one partial turn groove is a female helical groove and the at least one key is a complementary helical male ridge; and
    wherein a pitch of the helical groove and the ridge is selected to translate the enteral cap and interconnect between the received and disconnected positions in a partial turn of at least one of the enteral cap and the interconnect.

5. The enteral connection system according to claim 2, further comprising:
    the at least one partial turn groove includes a substantially longitudinal portion with an extent having at least one partial turn detent sized to receive and capture the at least one cooperative key upon receipt and a partial turn of the enteral cap.

6. The enteral connection system according to claim 5, wherein at least one of the at least one partial turn detent and the at least one cooperative key are adapted as a haptic actuator operative to emit perceptible feedback as the interconnect and the enteral cap translate into the received position.

7. The enteral feeding system according to claim 4, further comprising:
    at least one haptic actuator carried by at least one of the enteral cap and the interconnect; and
    wherein the at least one haptic actuator emits perceptible feedback as the interconnect and the enteral cap translate into the received position.

8. The enteral feeding system according to claim 7, wherein the perceptible feedback includes at least one of an audible and a tactile vibration.

9. An enteral connection system adapted to communicate fluid between a receptacle and an enteral feeding set, the receptacle including at least one side wall defining an interior volume and having a finish that forms a fluid communication port defining a seal plane, the system comprising:
    an end cap receivable about the fluid communication port and formed with at least one cap wall defining an interior lumen for communicating the fluid between the receptacle and the feeding set;
    the cap wall having an interior face carrying at least one spike barrier that radially spans the interior lumen to establish an interstice therein between the barrier and the seal plane;
    at least one barrier port formed in the spike barrier and in fluid communication with the interior lumen;
    a periphery circumscribing the at least one barrier port and having a barrier geometry defining a barrier keyway;
    an interconnect adapted to be moved between received and disconnected positions cooperatively with the end cap;
    at least one piercing tine carried from the interconnect and configured with a cross-sectional geometry substantially similar to the barrier geometry to enable receipt through the barrier keyway when the interconnect is moved into the received position;
    wherein the at least one piercing tine extends beyond the seal plane to enable fluid communication between the interior volume and the enteral feeding set; and
    wherein the interstice and at least one spike barrier define a distance there between greater than a length of at least one incompatible spike, whereby the legacy distance extends beyond an extent of the at least one incompatible spike.

10. An enteral connection system adapted to communicate fluid between a receptacle having a receptacle port and an enteral feeding set, the system comprising:
    an end cap receivable at a proximal end about the port and formed with at least one cap wall defining an interior lumen extending between proximal and distal ends and in fluid communication between the receptacle and the feeding set;
    the cap wall having an interior face that includes near the proximal end a lumen seal port receivable about the receptacle port, the seal port defining a cap seal plane that spans the interior lumen;
    at least one spike barrier radially spanning the interior lumen near the distal end and establishing an interstice between the barrier and the seal port that defines a distance;
    at least one barrier port formed in the spike barrier and in fluid communication with the interior lumen;
    a periphery circumscribing the at least one barrier port and having a barrier geometry; and
    wherein the interstice and at least one spike barrier define a distance greater than a length of at least one incompatible spike, whereby the distance extends the cap seal plane beyond an extent of the at least one incompatible spike.

11. The enteral connection system according to claim 10, further comprising:
a pierceable seal covering the receptacle port; and
wherein when the end cap is received about the receptacle port, a plane of the receptacle port is coplanar with the cap seal plane, and the pierceable seal obstructs the fluid communication.

12. The enteral connection system according to claim 10, further comprising:
a pierceable seal covering the seal port; and
wherein when the end cap is received about the receptacle port, the pierceable seal obstructs the fluid communication.

13. The enteral connection system according to claim 10, further comprising:
the end cap including at least one partial turn groove formed about a portion of the cap wall; and
an interconnect having at least one key cooperative with the partial turn groove to capture the interconnect from a disconnected position to a received position relative to the end cap.

14. The enteral connection system according to claim 13, further comprising:
at least one piercing tine carried from the interconnect and configured with a cross-sectional geometry substantially similar to the barrier geometry to enable receipt through the port keyway when the interconnect is translated into the received position;
wherein the at least one piercing tine extends to the cap seal plane piercing the seal to enable the fluid communication; and
wherein the at least one key is operative to obstruct receipt of the interconnect in at least one incompatible connector.

15. The enteral connection system according to claim 13, further comprising:
a plurality of piercing tines carried from the interconnect and configured with a cross-sectional geometry substantially similar to the barrier geometry to be receivable through the port keyway;
wherein at least one of the plurality of piercing tines extends to the cap seal plane to pierce the seal and enabling the fluid communication; and
wherein the at least one key is operative to obstruct receipt of the interconnect in at least one incompatible connector.

16. The enteral connection system according to claim 13, further comprising:
the at least one partial turn groove is a female helical groove and the at least key is a complementary helical male ridge; and
wherein a pitch of the helical groove and ridge is selected to translate the enteral cap and interconnect between the received and disconnected positions in a partial turn of at least one of the enteral cap and the interconnect.

17. The enteral connection system according to claim 16, further comprising:
the at least one partial turn groove also includes a substantially longitudinal groove with an extent having at least one partial turn detent sized to receive and capture the at least one cooperative key upon receipt and a partial turn of the enteral cap.

18. The enteral feeding system according to claim 16, further comprising:
at least one haptic actuator carried by at least one of the enteral cap and the interconnect; and
wherein the at least one haptic actuator emits perceptible feedback as the interconnect and the enteral cap translate into the received position.

19. An enteral connection system adapted to communicate fluid between a receptacle and an enteral feeding set, the receptacle including at least one side wall defining an interior volume and having a finish that forms a fluid communication port defining a receptacle seal plane, the system comprising:
an end cap receivable about the fluid communication port and formed with at least one cap wall defining an interior lumen for communicating the fluid between the receptacle and the feeding set;
the cap wall having an interior face carrying at least one spike barrier substantially spanning the interior lumen to establish an interstice therein between the barrier and the receptacle seal plane when the end cap is received about the receptacle;
at least one barrier port formed in the spike barrier and in fluid communication with the interior lumen;
a periphery circumscribing the at least one barrier port and having a barrier geometry that establishes at least two barrier keyways;
wherein the interstice and at least one spike barrier establish a distance exceeding a length of at least one incompatible spike to prevent the at least one incompatible spike from extending to the seal plane; and
an interconnect having at least one keyed tine carried from the interconnect and configured with a cross-sectional geometry substantially similar to the barrier geometry to be receivable through at least one of the barrier keyways.

20. The enteral connection system according to claim 19, further comprising:
wherein the at least one piercing tine extends beyond the seal plane to enable fluid communication between the interior volume and the enteral feeding set; and
wherein the at least one keyed tine obstructs receipt of the interconnect in at least one incompatible connector.

* * * * *